(12) United States Patent
Jurk et al.

(10) Patent No.: US 8,466,124 B2
(45) Date of Patent: *Jun. 18, 2013

(54) RNA SEQUENCE MOTIFS IN THE CONTEXT OF DEFINED INTERNUCLEOTIDE LINKAGES INDUCING SPECIFIC IMMUNE MODULATORY PROFILES

(75) Inventors: Marion Jurk, Dormagen (DE); Jorg Vollmer, Dusseldorf (DE)

(73) Assignee: Coley Pharmaceutical GmbH, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,216

(22) Filed: Jun. 12, 2012

(65) Prior Publication Data

US 2012/0258140 A1  Oct. 11, 2012

Related U.S. Application Data

(62) Division of application No. 13/360,894, filed on Jan. 30, 2010, now Pat. No. 8,227,447, which is a division of application No. 12/670,697, filed as application No. PCT/IB2008/002104 on Aug. 8, 2008, now Pat. No. 8,128,944.

(60) Provisional application No. 60/964,448, filed on Aug. 13, 2007.

(51) Int. Cl.
*A61K 48/00* (2006.01)
*C12Q 1/68* (2006.01)
*C07H 21/02* (2006.01)
*C12N 5/02* (2006.01)
*C12N 5/00* (2006.01)
*C07H 21/04* (2006.01)

(52) U.S. Cl.
USPC .......... 514/44 R; 435/6.1; 435/375; 435/325; 536/23.1; 536/24.5

(58) Field of Classification Search
None
See application file for complete search history.

(56) References Cited

U.S. PATENT DOCUMENTS

| 8,128,944 B2 | 3/2012 | Jurk et al. |
| 8,227,447 B2 | 7/2012 | Jurk et al. |
| 2003/0232074 A1 | 12/2003 | Lipford et al. |
| 2005/0239733 A1 | 10/2005 | Jurk et al. |
| 2005/0250723 A1 | 11/2005 | Hoerr et al. |
| 2006/0074040 A1 | 4/2006 | Kandimalla et al. |

FOREIGN PATENT DOCUMENTS

| WO | 03/015711 | 2/2003 |
| WO | 03/086820 | 10/2003 |
| WO | 2004/004743 | 1/2004 |
| WO | 2004/053104 | 6/2004 |
| WO | 2005/097993 | 10/2005 |
| WO | 2006/135434 | 12/2006 |
| WO | 2007/031322 | 3/2007 |
| WO | 2007/062107 | 5/2007 |

OTHER PUBLICATIONS

PCT International Search Report, PCT/IB2008/002104, mailed Apr. 3, 2009 (6 pages).
Hoffjan and Epplen, "Toll-like receptors and airway disease", Drug Discovery Today: Therapeutic Strategies, 3 (3):317-324, 2006.
Heil et al., "Species-Specific Recognition of Single-Stranded RNA via Toll-like Receptor 7 and 8", Science, 303:1526-1529, 2004.
PCT International Search Report, PCT/US2006/045183, mailed May 18, 2007 (8 pages).

*Primary Examiner* — Doug Schultz
(74) *Attorney, Agent, or Firm* — Paul M. Misiak; Vyacheslav V. Vasilyev

(57) ABSTRACT

Immunostimulatory polymers that contain certain sequence-dependent immunostimulatory RNA motifs and methods for the use of such immunostimulatory polymers and compositions containing such polymers are provided according to the invention. The sequence-dependent immunostimulatory RNA motifs and the polymers incorporating such motifs are potent and selective inducers of TLR7 and the TLR7-associated cytokine IFN-α.

5 Claims, 27 Drawing Sheets

SEQUENCE LISTING

<160> NUMBER OF SEQ ID NOS: 36

<210> SEQ ID NO 1
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 1
ccgucuguug ugugacuc                                                 18

<210> SEQ ID NO 2
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 2
aaacgcacag ccaaagcag                                                19

<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
aaacgcucag ccaaagcag                                                19

<210> SEQ ID NO 4
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 4
aaaaaaaaua aaaaaaaa                                                 18

<210> SEQ ID NO 5
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: phosphorothioate backbone

<400> SEQUENCE: 5
aaacgcucag ccaaagcag                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 6
aaacgcacag ccaaagcuc                                                19

```
<210> SEQ ID NO 7
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 7
acgcacagcc aaagcucag                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 8
aaacgcugag ccaaagcag                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 9
aaacgcuaag ccaaagcag                                                  19

<210> SEQ ID NO 10
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 10
aaacgcuuag ccaaagcag                                                  19

<210> SEQ ID NO 11
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 11
gccaccgagc ugaaggcacc                                                 20

<210> SEQ ID NO 12
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 12
gccaccgagc ucaaggcacc                                                 20

<210> SEQ ID NO 13
<211> LENGTH: 19
<212> TYPE: RNA
<213> ORGANISM: Artificial Sequence
<220> FEATURE:
<223> OTHER INFORMATION: Synthetic oligonucleotide
```

<400> SEQUENCE: 13
aaacgcuccg ccaaagcag                                                19

<210> SEQ ID NO 14
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 14
aaacgcucgg ccaaagcag                                                19

<210> SEQ ID NO 15
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 15
aaacgcucug ccaaagcag                                                19

<210> SEQ ID NO 16
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 16
aaacgcucaa ccaaagcag                                                19

<210> SEQ ID NO 17
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 17
aaacgcucac ccaaagcag                                                19

<210> SEQ ID NO 18
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 18
aaacgcucau ccaaagcag                                                19

<210> SEQ ID NO 19
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 19
aaacggucag ccaaagcag                                                19

<210> SEQ ID NO 20
<211> LENGTH: 19
<212> TYPE: RNA

```
<213> ORGANISM: Artificial Sequence
<220> FEATURE:
<223> OTHER INFORMATION: Synthetic oligonucleotide

<400> SEQUENCE: 20
aaacgaucag ccaaagcag                                                 19

<210> SEQ ID NO 21
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 21
aaacguucag ccaaagcag                                                 19

<210> SEQ ID NO 22
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 22
aaacacucag ccaaagcag                                                 19

<210> SEQ ID NO 23
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 23
aaacccucag ccaaagcag                                                 19

<210> SEQ ID NO 24
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 24
aaacucucag ccaaagcag                                                 19

<210> SEQ ID NO 25
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 25
gacacacaca cacacacaca caca                                           24

<210> SEQ ID NO 26
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 26
gacacacaca cacacacaca cuuu                                           24
```

```
<210> SEQ ID NO 27
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 27
gacacacaca cucacacaca caca                                           24

<210> SEQ ID NO 28
<211> LENGTH: 20
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: phosphorothioate backbone

<400> SEQUENCE: 28
uuguuguugu uguuguuguu                                                20

<210> SEQ ID NO 29
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 29
gacacacaca cacacacaca cacu                                           24

<210> SEQ ID NO 30
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 30
gacacacaca cacacacaca cauu                                           24

<210> SEQ ID NO 31
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 31
uuguuguugu uguuguuguu                                                20

<210> SEQ ID NO 32
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 32
uuauuauuau uauuauuauu                                                20

<210> SEQ ID NO 33
<211> LENGTH: 20
<212> TYPE: RNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: phosphorothioate backbone

<400> SEQUENCE: 33
uuauuauuau uauuauuauu                                              20

<210> SEQ ID NO 34
<211> LENGTH: 14
<212> TYPE: RNA
<213> ORGANISM: Artificial Sequence
<220> FEATURE:
<223> OTHER INFORMATION: Synthetic oligonucleotide

<400> SEQUENCE: 34
uuaucguamc ucac                                                    14

<210> SEQ ID NO 35
<211> LENGTH: 16
<212> TYPE: RNA
<213> ORGANISM: Artificial Sequence
<220> FEATURE:
<223> OTHER INFORMATION: Synthetic oligonucleotide

<400> SEQUENCE: 35
ccgagccgag cucacc                                                  16

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
tccatgacgt tcctgacgtt                                              20
```

US 8,466,124 B2

RNA SEQUENCE MOTIFS IN THE CONTEXT OF DEFINED INTERNUCLEOTIDE LINKAGES INDUCING SPECIFIC IMMUNE MODULATORY PROFILES

CROSS-REFERENCE TO RELATED APPLICATIONS

This application claims priority under 35 U.S.C. §119(e) to U.S. Provisional Application No. 60/964,448, entitled "Sequence Motifs in the Context of Defined Internucleotide Linkages Inducing Specific Immune Modulatory Profiles," filed on Aug. 13, 2007, which is herein incorporated by reference in its entirety.

BACKGROUND OF THE INVENTION

Toll-like receptors (TLRs) are a family of highly conserved pattern recognition receptor (PRR) polypeptides that recognize pathogen-associated molecular patterns (PAMPs) and play a critical role in innate immunity in mammals. Currently at least ten family members, designated TLR1-TLR10, have been identified. The cytoplasmic domains of the various TLRs are characterized by a Toll-interleukin 1 receptor (TIR) domain. Medzhitov R et al. (1998) *Mol Cell* 2:253-8. Recognition of microbial invasion by TLRs triggers activation of a signaling cascade that is evolutionarily conserved in *Drosophila* and mammals. The TIR domain-containing adapter protein MyD88 has been reported to associate with TLRs and to recruit interleukin 1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun $NH_2$ terminal kinase (Jnk) mitogen-activated protein kinases (MAPKs), critical steps in immune activation and production of inflammatory cytokines. For reviews, see Aderem A et al. (2000) *Nature* 406:782-87, and Akira S et al. (2004) *Nat Rev Immunol* 4:499-511.

A number of specific TLR ligands have been identified. Ligands for TLR2 include peptidoglycan and lipopeptides. Yoshimura A et al. (1999) *J Immunol* 163:1-5; Yoshimura A et al. (1999) *J Immunol* 163:1-5; Aliprantis A O et al. (1999) *Science* 285:736-9. Lipopolysaccharide (LPS) is a ligand for TLR4. Poltorak A et al. (1998) *Science* 282:2085-8; Hoshino K et al. (1999) *J Immunol* 162:3749-52. Bacterial flagellin is a ligand for TLR5. Hayashi F et al. (2001) *Nature* 410:1099-1103. Peptidoglycan has been reported to be a ligand not only for TLR2 but also for TLR6. Ozinsky A et al. (2000) *Proc Natl Acad Sci USA* 97:13766-71; Takeuchi O et al. (2001) *Int Immunol* 13:933-40. Recently certain low molecular weight synthetic compounds, the imidazoquinolines imiquimod (R-837) and resiquimod (R-848), were reported to be ligands of TLR7 and TLR8. Hemmi H et al. (2002) *Nat Immunol* 3:196-200; Jurk M et al. (2002) *Nat Immunol* 3:499.

Beginning with the discovery that unmethylated bacterial DNA and synthetic analogs thereof (CpG DNA) are ligands for TLR9 (Hemmi H et al. (2000) *Nature* 408:740-5; Bauer S et al. (2001) *Proc Natl Acad Sci USA* 98, 9237-42), it has been reported that ligands for certain TLRs include certain nucleic acid molecules. Recently it has beer reported that certain types of RNA are immunostimulatory in a sequence-independent or sequence-dependent manner. Further, it has been reported that these various immunostimulatory RNAs stimulate TLR3, TLR7, and TLR8.

SUMMARY OF THE INVENTION

The invention relates generally to immunostimulatory polymers that contain certain immunostimulatory sequence motifs, as well as to related immunostimulatory compositions containing such immunostimulatory polymers, and methods for the use of such immunostimulatory polymers and compositions. In some aspects of the invention the immunostimulatory polymers are immunostimulatory oligoribonucleotides (ORN).

The immunostimulatory polymers of the invention may be useful in any setting or application that calls for stimulating or augmenting an immune response. As disclosed below, the immunostimulatory polymers of the invention are of particular use in the preparation of pharmaceutical compositions, including adjuvants, vaccines, and other medicaments, for use in treating a variety of conditions, including infection, cancer, allergy, and asthma. The invention in certain aspects thus relates to compositions that include immunostimulatory polymers of the invention, as well as methods of their use.

As disclosed in greater detail below, the immunostimulatory polymers of the invention are characterized by their inclusion of at least one sequence-dependent immunostimulatory motif sequence. The sequence-dependent immunostimulatory motif sequences and the polymers incorporating such motifs are disclosed to be potent inducers of the TLR7-associated cytokine interferon alpha (IFN-α).

One aspect of the invention is a composition comprising a single-stranded polymer 4 to 100 units long comprising $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA. The composition in one embodiment further includes a delivery vehicle, wherein the delivery vehicle is a liposome, a noisome, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle (such as a nanosphere or a nanocapsule), or a polymeric microparticle (such as a microsphere or a microcapsule) and wherein the composition does not include lipofectin. In one embodiment $N_1$ includes at least one A. In another embodiment $N_1$ includes at least one C. In yet another embodiment $N_1$ includes at least one G. In still another embodiment, $N_1$ includes at least one T. In one embodiment $N_2$ includes at least one A. In another embodiment $N_2$ includes at least one C. In yet another embodiment $N_2$ includes at least one G. In still another embodiment $N_2$ includes at least one T.

Another aspect of the invention is a composition comprising a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUA$X_1$CUCAC (SEQ ID NO:34), wherein $X_1$ is A or C. The composition in one embodiment further includes a delivery vehicle, wherein the delivery vehicle is a liposome, a noisome, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle (such as a nanosphere or a nanocapsule), or a polymeric microparticle (such as a microsphere or a microcapsule) and wherein the composition does not include lipofectin. In one embodiment $X_2$ is A. In one embodiment $X_2$ is C. In another embodiment $X_2$ is G. In one embodiment $X_3$ is A. In another embodiment $X_3$ is C. In another embodiment $X_3$ is G. In one embodiment $N_3$ includes at least one A. In another embodiment $N_3$ includes at least one C. In yet another embodiment $N_3$ includes at least one G. In still another embodiment $N_3$ includes at least one U. In one embodiment $N_4$ includes at least one A. In another embodiment $N_4$ includes at least one C. In another embodiment $N_4$ includes at least one G. In another embodiment $N_4$ includes at least one U.

The aforementioned compositions may comprise additional elements or modifications to the polymer. For example, in one embodiment the compositions further comprise an antigen. In one embodiment, the antigen is conjugated to the polymer. In one embodiment, the $rN_1$-rC-rU-rC-rA-$rN_2$ or $rN_3$-$rX_2$-rC-rU-rC-rA-$rX_3$-$rN_4$ motif comprises a modified nucleobase selected from the group consisting of hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), and any combination thereof. In another embodiment, the polymer comprises at least one modified nucleobase outside of the $rN_1$-rC-rU-rC-rA-$rN_2$ or $rN_3$-$rX_2$-rC-rU-rC-rA-$rX_3$-$rN_4$ motif, wherein the modified nucleobase is selected from the group consisting of hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-($C_2$-$C_6$)-alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), and any combination thereof. In another embodiment, the polymer further comprises a lipophilic moiety covalently linked to the polymer. In one embodiment the lipophilic moiety is selected from the group consisting of cholesteryl, palmityl, and fatty acyl. In another embodiment the polymer does not include a CpG motif. In yet another embodiment the polymer does not include CCGAGCCGAGCUCACC (SEQ ID NO:35). In one embodiment the polymer is 4 to 20 units long. In another embodiment the polymer is 10 to 25 units long. In another embodiment the polymer 15 to 19 units long. In one embodiment each unit of the polymer is a ribonucleotide. In another embodiment the polymer units are a mixture of ribonucleotides and deoxyribonucleotides. In another embodiment the deoxyribonucleotides include a TCG motif on the 5' end of the polymer. In still another embodiment at least one unit of the polymer is an amino acid. In one embodiment the polymer is linked to a TLR9 agonist. In one embodiment the TLR9 agonist is a small molecule. In another embodiment the polymer is linked to a TLR7 agonist. In yet another embodiment the polymer is linked to a TLR8 agonist.

Another aspect of the invention is a method, comprising contacting an immune cell capable of producing IFN-α with a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUA$X_1$CUCAC (SEQ ID NO:34), wherein $X_1$ is A or C, wherein the polymer is not formulated with lipofectin, in an amount effective to induce therapeutically substantial IFN-alpha production. In one embodiment the polymer comprises at least one stabilized linkage outside of the immunostimulatory motif. In another embodiment the polymer comprises 1-5 stablized linkages outside of the immunostimulatory motif. In one embodiment the stabilized linkage(s) is/are at the 5' and/or 3' terminus.

Another aspect of the invention is a method, comprising contacting an immune cell capable of producing IFN-α with a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUA$X_1$CUCAC (SEQ ID NO:34), wherein $X_1$ is A or C, wherein the polymer is not formulated with lipofectin in an amount effective to induce therapeutically substantial IFN-alpha production.

In one embodiment the aforementioned methods do not result in the immune cells producing substantial amounts of tumor necrosis facotr alpha (TNF-α), interferon gamma (IFN-γ), or interleukin 12 (IL-12) in response to the polymer. In some embodiments the methods are performed in vivo. In some embodiments the polymer is administered in the form of any of the compositions described above.

Another aspect of the invention is a method for treating asthma, comprising administering to a subject having asthma an effective amount for treating asthma of a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUA$X_1$CUCAC (SEQ ID NO:34), wherein $X_1$ is A or C.

Another aspect of the invention is a method for treating asthma, comprising administering to a subject having asthma an effective amount for treating asthma of a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUA$X_1$CUCAC (SEQ ID NO:34), wherein $X_1$ is A or C.

In one embodiment either of the methods for treating asthma described above may further comprise administering to the subject an allergen. In one embodiment, the polymer is conjugated to the allergen. In some embodiments the polymer is administered in the form of any of the compositions described above.

Another aspect of the invention is a method for treating an allergic condition, comprising administering to a subject having an allergic condition an effective amount for treating the allergic condition of a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUAX$_1$CUCAC (SEQ ID NO:34), wherein $X_1$ is A or C.

Another aspect of the invention is a method for treating an allergic condition, comprising administering to a subject having an allergic condition an effective amount for treating the allergic condition of a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUAX$_1$CUCAC (SEQ ID NO:34), wherein $X_1$ is A or C.

In one embodiment either of the methods for treating an allergic condition described above may further comprise administering to the subject an allergen. In one embodiment the polymer is conjugated to the allergen. In some embodiments the polymer is administered in the form of any of the compositions described above.

Another aspect of the invention is a method for treating cancer, comprising administering to a subject having cancer an effective amount for treating cancer of a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUAX$_1$CUCAC (SEQ ID NO:34), wherein $X_1$ is A or C.

Another aspect of the invention is a method for treating cancer, comprising administering to a subject having cancer an effective amount for treating cancer of a single-stranded polymer 4 to 100 units long comprising an immunostimulatory RNA motif $rN_3$-$rX_2$-rC-rU-rC-rA-$X_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUAX$_1$CUCAC (SEQ ID NO:34), wherein $X_1$ is A or C.

In one embodiment either of the methods for treating cancer described above may further comprise administering to the subject a cancer antigen. In one embodiment the polymer is conjugated to the antigen. In other embodiments the methods further comprise administering to the subject a second cancer medicament. In one embodiment the cancer medicament is one or more of carboplatin, paclitaxel, cisplatin, 5-fluorouracil, doxorubicin, taxol and gemcitabine. In some embodiments the polymer is administered in the form of any of the compositions described above.

Another aspect of the invention is a method for treating an infectious disease, comprising administering to a subject having an infectious disease an effective amount for treating the infectious disease of a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUAX$_1$CUCAC (SEQ ID NO:34), wherein $X_1$ is A or C.

Another aspect of the invention is a method for treating an infectious disease, comprising administering to a subject having an infectious disease an effective amount for treating the infectious disease of a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUAX$_1$CUCAC (SEQ ID NO:34), wherein $X_1$ is A or C.

In one embodiment either of the methods for treating an infectious disease described above may further comprise administering to the subject a microbial antigen. In one embodiment the polymer is conjugated to the antigen. In some embodiments the polymer is administered in the form of any of the compositions described above.

Another aspect of the invention is a method for inducing a T helper type 1 (Th1)-like immune response in a subject, comprising administering to the subject an effective amount of a single-stranded polymer 4 to 100 units long comprising an immunostimulatory RNA motif $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ and wherein $rN_1$-rC-rU-rC-rA-$rN_2$ is not GCUCAA or UUAUCGUAX$_1$CUCAC (SEQ ID NO:34), wherein $X_1$ is A or C.

Another aspect of the invention is a method for inducing a T helper type 1 (Th1)-like immune response in a subject, comprising administering to the subject an effective amount of a single-stranded polymer 4 to 100 units long comprising an immunostimulatory RNA motif $rN_3$-$rX_2$-rC-rU-rC-rA-$rX_3$-$rN_4$, where $X_2$ and $X_3$, independent of each other, are absent or are nucleotides selected from the group of nucleotides consisting of C, G, and A and nucleotide analogs thereof, wherein $N_3$ and $N_4$, independent of each other, are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUAX$_1$CUCAC (SEQ ID NO:34), wherein $X_1$ is A or C.

In one embodiment either of the methods for inducing a Th1-like immune response described above may further comprise administering to the subject an antigen.

In one embodiment the polymer is conjugated to the antigen. In some embodiments the polymer is administered in the form of any of the compositions described above.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

DETAILED DESCRIPTION OF THE INVENTION

Immunostimulatory oligoribonucleotides (ORN) have been described which appear to stimulate the human immune system in a TLR7- and/or TLR8-dependent manner. For instance, ORN containing GU rich and CU rich motifs lacking poly-G ends appear to act on TLR7 and TLR8. ORN with AU rich motifs lacking poly-G ends appear to act on TLR8 only. ORN containing an immunostimulatory RNA motif flanked by poly G motif(s) appear to stimulate an immune response through TLR7 and not TLR8. These produce high amounts of IFN-α in the presence of cationic liposomal formulations such as e.g. DOTAP. This effect seems to be TLR7-mediated, as the IFN-α-producing plasmacytoid dendritic cells (pDC) express TLR7 and no TLR8. The observed stimulation of other cytokines, e.g., TNF-α, IL-12 and IFN-γ, appears to be TLR8-mediated. For example, activation of monocytes is most likely a direct TLR8-mediated effect because monocytes are shown to express TLR8 but not TLR7, and secrete TNF-α upon ssRNA stimulation. Recently ORN with different immune profiles and having a defined a motif for the activation of RNA-mediated responses have been identified. Some of these ORN do not induce IFN-α production by human PBMC, but do induce significant amounts of TNF-α, IL-12 and IFN-γ, pointing to a stimulation of TLR8 but not TLR7.

The instant invention involves the finding of a class of polymers containing specific RNA motifs that can induce RNA-mediated immune responses referred to as TLR7-mediated (such as IFN-α production from pDC) without inducing substantial amounts of TLR8-mediated (i.e., production of cytokines produced by TLR8-expressing cells such as TNF-α from monocytes) immune activation. As used herein, a "substantial amount" shall mean an amount that is different from amounts produced by other immunostimulatory ORN. "Without inducing substantial amounts of TLR8-mediated immune activation" refers to immune activation such that levels of factors associated with TLR activation that are induced are minimal when compared with levels induced by ORN such as those containing GU rich and CU rich motifs lacking poly-G ends mentioned above, or other ORN that appear to stimulate TLR8. Thus, the ORN of the instant invention induce less of the cytokines typical for an RNA TLR8 or TLR7/8 ligand, e.g., pro-inflammatory cytokines TNF-alpha, IL-6. In some embodiments a substantial amount is a "significant amount." The class of polymers described herein are single-stranded, have a phosphodiester backbone, and have an immunostimulatory RNA motif containing a CUCA sequence.

Figure 4A:
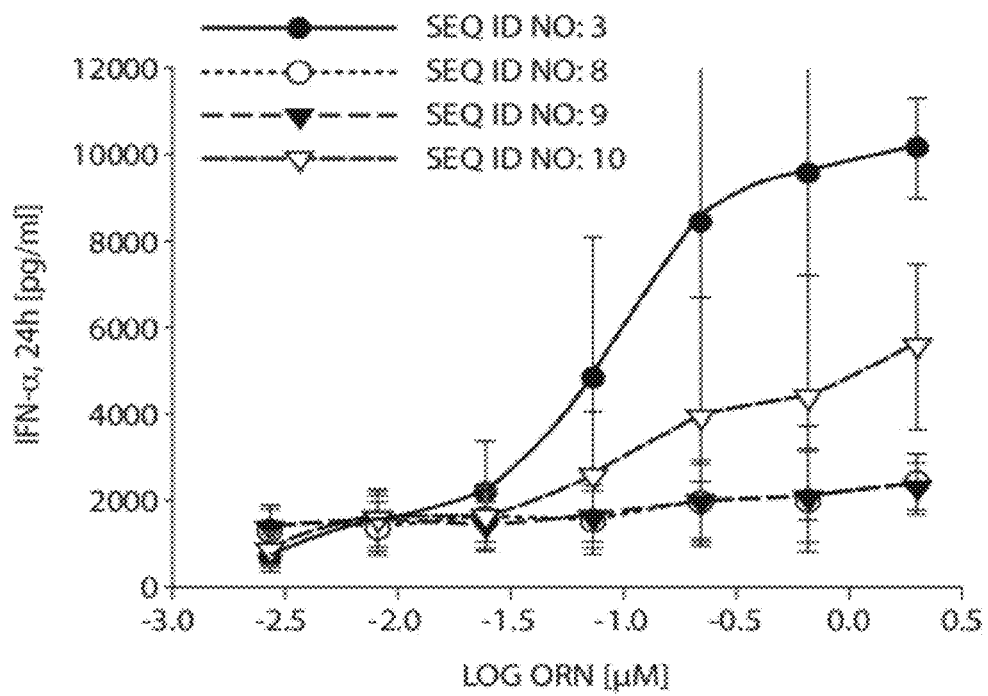
FIG. 4 is two graphs showing induction of IFN-α (FIG. 4A) and IL-12p40 (FIG. 4B) by ORN. Shown are SEQ ID NO:3 and three other ORN with slight sequence variations (SEQ ID NO:8-10, see Table 3). Human PBMC were incubated with ORN in the presence of DOTAP (2 M ORN and 25 μg/ml DOTAP) and supernatants were assayed for IFN-α and IL-12p40 24 hours later by ELISA. Mean—SEM of 3 donors is shown. The y-axes are IFN-α (FIG. 4A) and IL-12p40 (FIG. 4B) concentration in pg/ml and the x-axis shows log ORN concentration in μM.
Figure 4B:
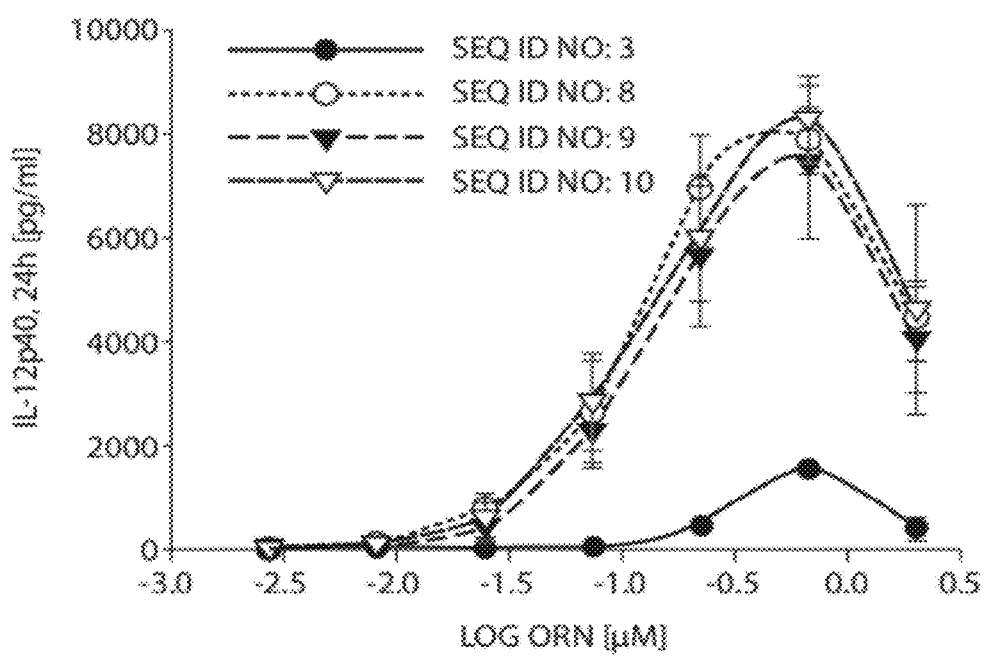

This class is associated with an immune profile that is characteristic for the almost exclusive activation of a TLR7-like immune response. For example, as shown in FIG. 4, a polymer of the invention, SEQ ID NO:3, induces very high amounts of IFN-α when formulated with DOTAP with no significant induction of IL-12p40. In contrast, polymers with similar sequence but lacking the immunostimulatory CUCA motif, SEQ ID NOs 8-10, induced high amounts of IL-12p40.

The new immunostimulatory motif that has been discovered that is immunostimulatory when in the context of a phosphodiester backbone only. Interestingly the immunostimulatory polymers of the invention which contain this motif have been found to produce a strong IFN-α response but do not stimulate other typical cytokines, for instance those induced in response to TLR8 stimulation. Thus, an aspect of the invention is an immunostimulatory polymer containing an immunostimulatory motif that induces predominantly TLR7 associated cytokines and has a phosphodiester backbone.

In one aspect of the invention the immunostimulatory RNA motif is $rN_1$-rC-rU-rC-rA-$rN_2$, wherein the polymer is free of U outside of the motif rC-rU-rC-rA, wherein the polymer comprises a phosphodiester backbone wherein at least one of $N_1$ and $N_2$ is not $A_7$ (rA-rA-rA-rA-rA-rA-rA) and wherein $rN_1$-rC-rU-rC-rA-$rN_2$ is not GCUCAA or UUAUCGUA$X_1$CUCAC (SEQ ID NO:34), wherein $X_1$ is A or C. In some embodiments $N_1$ includes at least one A, one C, or one G. In other embodiments $N_1$ includes at least one T, for example, in an RNA:DNA chimera. In some embodiments $N_2$ includes at least one A, one C, one G, or one T.

In another aspect of the invention the immunostimulatory RNA motif is $rN_3$-$rX_2$-rC-rU-rC-rA-$rX_3$-$rN_4$, where $X_2$ and $X_3$ are absent or are nucleotides selected from the group of nucleosides and nucleoside analogs consisting of C, G, and A, wherein $N_3$ and $N_4$ are absent or are one or more nucleotides, wherein the polymer comprises a phosphodiester backbone and does not include two $A_7$ motifs and wherein $rN_3$-$rX_2$-rC-rU-rC-rA-$rX_3$-$rN_4$ is not GCUCAA or UUAUCGUA$X_1$CUCAC (SEQ ID NO:34), wherein $X_1$ is A or C. In some embodiments the polymer does not contain CCGAGCCGAGCUCACC (SEQ ID NO:35). In some embodiments of the invention $N_3$ and $N_4$ each independently include at least one A, C, G, or U.

In some embodiments the immunostimulatory polymers are between 4 and 100 units long. In other embodiments the immunostimulatory polymers are 4 to 20 units long. In other embodiments the immunostimulatory polymers are 10 to 25 units long. In still other embodiments the immunostimulatory polymers are 15 to 19 units long.

As discussed in more detail in the Examples below, the CUCA of the immunostimulatory motif was found to be important for the TLR7-like immune response. Surprisingly, the immune stimulatory effects were specific to phosphodiester rather than a phosphorothioate backbone. In some embodiments the immunostimulatory polymers of the invention have more than one immunostimulatory motif.

The immunostimulatory polymers of the invention are single-stranded. According to the methods of the invention, the polymers are not designed to comprise a sequence complementary to that of a coding sequence in a human cell, and are therefore not considered to be antisense ORN or silencing RNA (siRNA). A polymer which is "not complementary" is one that does not comprise a sequence capable of hybridizing strongly with one particular coding region in the target cell, for instance, it does not hybridize under stringent conditions. Therefore, administration of a polymer which is not complementary will not result in gene silencing, especially as the polymers described in this invention are single-stranded compared to the double-stranded molecules used for gene silencing.

The polymers of the invention have the ability to induce an immune response inducing significant amounts of IFN-α or IFN-α-related molecules relative to background. An IFN-α-related molecule is a cytokine or factor that is related to the expression of IFN-α. These molecules include but are not limited to MIP1-β, IP-10 and MIP1-α.

The invention relates generally to immunostimulatory polymers that include an immunostimulatory RNA motif, immunostimulatory compositions containing one or more immunostimulatory polymers of the invention, and methods for use of the immunostimulatory polymers and immunostimulatory compositions of the invention. As used herein, the term "RNA" shall refer to two or more ribonucleotides (i.e., molecules each comprising a ribose sugar linked to a phosphate group and to a purine or pyrimidine nucleobase (e.g., guanine, adenine, cytosine, or uracil)) covalently linked together by 3'-5' phosphodiester linkage(s).

As mentioned above, RNA is a polymer of ribonucleotides joined through 3'-5' phosphodiester linkages. In certain embodiments the immunostimulatory polymers of the invention are RNA. In other embodiments the invention provides an immunostimulatory composition that includes a chimeric DNA:RNA molecule that includes an immunostimulatory RNA motif of the invention. In one embodiment of the invention the deoxyribonucleotide residues of the DNA:RNA molecule include a TCG motif at the 5' end of the polymer. In one embodiment a DNA component of the chimeric DNA:RNA molecule includes a CpG nucleic acid, i.e., a TLR9 agonist. In one embodiment the DNA and RNA portions of the chimeric DNA:RNA molecule are covalently linked through an internucleotide phosphate bond. In another embodiment the DNA and RNA portions of the chimeric DNA:RNA molecule are covalently linked through a linker, e.g., a non-nucleotidic linker.

In another embodiment, at least one unit of the polymer is an amino acid.

In some embodiments the immunostimulatory polymers of the invention are linked to a TLR9 agonist that is not a CpG nucleic acid. In some embodiments the immunostimulatory polymers of the invention are linked to a TLR7 agonist or a TLR8 agonist. The agonist can be a deoxynucleotide or ribonucleotide, or it may be a peptide or a small molecule. The immunostimulatory polymers may be linked directly to the agonist or they may be connected via a linker.

The immunostimulatory polymers of the instant invention can encompass various chemical modifications and substitutions, in comparison to natural RNA and DNA, involving a phosphodiester internucleotide linkage, a β-D-ribose unit and/or a natural nucleotide base (adenine, guanine, cytosine, thymine, uracil). Examples of chemical modifications are known to the skilled person and are described, for example, in Uhlmann E et al. (1990) Chem Rev 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) Annu Rev Pharmacol Toxicol 36:107-129; and Hunziker J et al. (1995) Mod Synth Methods 7:331-417. An oligonucleotide according to the invention may have one or more modifications, wherein each modification is located at a particular phosphodiester internucleotide linkage and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:
a) the replacement of a phosphodiester internucleotide linkage located at the 3' and/or the 5' end of a nucleotide by a modified internucleotide linkage,
b) the replacement of phosphodiester linkage located at the 3' and/or the 5' end of a nucleotide by a dephospho linkage,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

In one embodiment the ORN may have at least one stabilized internucleotide linkage. Typically the linkage would be at or near either the 5' or 3' terminus and not within the immunostimulatory motif. A phosphodiester internucleotide linkage located at the 3' and/or the 5' end of a nucleotide can be replaced by at least one modified internucleotide linkage, wherein the modified internucleotide linkage is for example selected from phosphorothioate, phosphorodithioate, $NR^1R^2$-phosphoramidate, boranophosphate, α-hydroxybenzyl phosphonate, phosphate-($C_1$-$C_{21}$)-O-alkyl ester, phosphate-[($C_6$-$C_{12}$)aryl-($C_1$-$C_{21}$)-O-alkyl]ester, ($C_1$-$C_8$)alkylphosphonate and/or ($C_6$-$C_{12}$)arylphosphonate linkages, ($C_7$-$C_{12}$)-α-hydroxymethyl-aryl (e.g., disclosed in WO 95/01363), wherein $(C_6\text{-}C_{12})$aryl, $(C_6\text{-}C_{20})$aryl and $(C_6\text{-}C_{14})$ aryl are optionally substituted by halogen, alkyl, alkoxy, nitro, cyano, and where $R^1$ and $R^2$ are, independently of each other, hydrogen, $(C_1\text{-}C_{18})$-alkyl, $(C_6\text{-}C_{20})$-aryl, $(C_6\text{-}C_{14})$-aryl-$(C_1\text{-}C_8)$-alkyl, preferably hydrogen, $(C_1\text{-}C_8)$-alkyl, preferably $(C_1\text{-}C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N. In one embodiment the ORN has 1-5 stabilized linkages.

The replacement of a phosphodiester linkage located at the 3' and/or the 5' end of a nucleotide by a dephospho linkage (dephospho linkages are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho linkage is for example selected from the dephospho linkages formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide linkage together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is, for example, 3-D-ribose, α-D-2'-deoxyribose, L-2'-deoxyribose, 2'-F-2'-deoxyribose, 2'-F-arabinose, 2'-O-$(C_1\text{-}C_6)$alkyl-ribose, preferably 2'-O-$(C_1\text{-}C_6)$alkyl-ribose is 2'-O-methylribose, 2'-O-$(C_2\text{-}C_6)$alkenyl-ribose, 2'-[O-$(C_1\text{-}C_6)$alkyl-O-$(C_1\text{-}C_6)$alkyl]-ribose, 2'-NH$_2$-2'-deoxyribose, β-D-xylo-furanose, α-arabinofuranose, 2,4-dideoxy-(3-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclo-sugar analogs (described, fior example, in Tarkov M et al. (1993) *Helv Chim Acta* 76:481).

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

An immunostimulatory polymer of the invention can in one embodiment include one or more modified nucleobases outside the immunostimulatory motif, i.e., derivatives of A, C, G, T, and U. Specific embodiments of these modified nucleobases include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil), thymine derivatives (e.g. 2-thiothymine, 4-thiothymine, 6-substituted thymines), guanosine derivatives (7-deazaguanine, 7-deaza-7-substituted guanine (such as 7-deaza-7-$(C_2\text{-}C_6)$-alkynylguanine), 7-deaza-8-substituted guanine, hypoxanthine, N2-substituted guanines (e.g. N2-methyl-guanine), 8-substituted guanine (e.g. 8-hydroxyguanine and 8-bromoguanine), and 6-thioguanine), or adenosine derivatives (5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine)). The base can also be substituted by a universal base (e.g. 4-methyl-indole, 5-nitro-indole, 3-nitropyrrole, P-base, and K-base), an aromatic ring system (e.g. benzimidazole or dichloro-benzimidazole, 1-methyl-1H-[1,2,4]triazole-3-carboxylic acid amide) an aromatic ring system (e.g. fluorobenzene or difluorobenzene) or a hydrogen atom (dSpacer). Modified U nucleobases are uracil derivatives such as dihydrouracil, pseudouracil, 2-thiouracil, 4-thiouracil, 5-aminouracil, 5-$(C_2\text{-}C_6)$-alkyluracil, 5-methyluracil, 5-$(C_2\text{-}C_6)$-alkenyluracil, 5-$(C_2\text{-}C_6)$-alkynyluracil, 5-(hydroxymethyl)uracil, 5-chlorouracil, 5-fluorouracil, or 5-bromouracil. The foregoing modified nucleobases and their corresponding nucleosides are available from commercial suppliers. This list is meant to be exemplary and is not to be interpreted to be limiting.

The compositions of the invention encompass polymers with and without secondary or higher order structure. For example, the polymer in one embodiment includes a sequence of nucleosides, nucleoside analogs, or a combination of nucleosides and nucleoside analogs capable of forming secondary structure provided by at least two adjacent hydrogen-bonded base pairs. In one embodiment the at least two adjacent hydrogen-bonded base pairs involve two sets of at least 3 consecutive bases. The consecutive nature of involved bases is thermodynamically advantageous for forming a so-called clamp. However, consecutive bases may not be required, particularly where there is high GC content and/or extended sequence. Typically there will be 3, 4, 5, 6, 7, 8, 9, 10, 11, 12, 13, 14, 15, or 16 base pairs. A hydrogen-bonded base pair in one embodiment can be classical Watson-Crick base pair, i.e., G-C, A-U, or A-T. In other embodiments a hydrogen-bonded base pair can be a non-classical base pair, such as G-U, G-G, G-A, or U-U. In yet other embodiments a hydrogen-bonded base pair can be a Hoogsteen or other base pair.

In one embodiment the secondary structure is a stem-loop secondary structure. A stem-loop or hairpin secondary structure can arise through intramolecular hydrogen-bonded base pairing between complementary or at least partially complementary sequences. The complementary or at least partially complementary sequences represent perfect or interrupted inverted repeat sequences, respectively. For example, a polymer having a base sequence provided by 5'-$X_1$-$X_2$-$X_3$ . . . $X_3$'-$X_2$'-$X_1$'-3', wherein each of $X_1$ and $X_1$', $X_2$ and $X_2$', and $X_3$ and $X_3$' can form a hydrogen-bonded base pair, may include a perfect or interrupted inverted repeat and has the potential to fold on itself and form a stem-loop secondary structure. It will be appreciated that a polymer having a base sequence provided by 5'-$X_1$-$X_2$-$X_3$ . . . $X_3$'-$X_2$'-$X_1$'-3', wherein each of $X_1$ and $X_1$', $X_2$ and $X_2$', and $X_3$ and $X_3$' can form a hydrogen-bonded base pair, also has the potential to form intermolecular complexes through intermolecular hydrogen-bonded base pairs. Where there are two or more inverted repeats, individual polymers can also interact to form not only dimeric intermolecular complexes but also higher-order intermolecular complexes or structures. Persons skilled in the art will recognize that conditions and/or sequences can be selected so as to favor formation of one type of secondary structure over another.

In one aspect the invention provides a conjugate of an immunostimulatory polymer of the invention and a lipophilic moiety. In certain embodiments the immunostimulatory polymer is covalently linked to a lipophilic moiety. The lipophilic moiety generally will occur at one or more ends of an immunostimulatory ORN having free ends, although in certain embodiments the lipophilic moiety can occur elsewhere along the immunostimulatory polymer and thus does not require the immunostimulatory ORN have a free end. In one embodiment the immunostimulatory polymer has a 3' end and the lipophilic moiety is covalently linked to the 3' end. The lipophilic group in general can be a cholesteryl, a modified cholesteryl, a cholesterol derivative, a reduced cholesterol, a substituted cholesterol, cholestan, C16 alkyl chain, a bile acid, cholic acid, taurocholic acid, deoxycholate, oleyl litocholic acid, oleoyl cholenic acid, a glycolipid, a phospholipid, a sphingolipid, an isoprenoid, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. In certain embodiments the lipophilic moiety is chosen from cholesteryl, palmityl, and fatty acyl. It is believed that inclusion of one or more of such lipophilic moieties in the immunostimulatory ORN of the invention confers upon them yet additional stability against degradation by nucleases. Where there are two or more lipophilic moieties in a single immunostimulatory polymers of the invention, each lipophilic moiety can be selected independently of any other.

In one embodiment the lipophilic group is attached to a 2'-position of a nucleotide of the immunostimulatory polymers. A lipophilic group can alternatively or in addition be linked to the heterocyclic nucleobase of a nucleotide of an immunostimulatory polymer. The lipophilic moiety can be covalently linked to the immunostimulatory polymer via any suitable direct or indirect linkage. In one embodiment the linkage is direct and is an ester or an amide. In one embodiment the linkage is indirect and includes a spacer moiety, for example one or more abasic nucleotide residues, oligoethyleneglycol, such as triethyleneglycol (spacer 9) or hexaethylenegylcol (spacer 18), or an alkane-diol, such as butanediol.

In one embodiment the immunostimulatory polymers of the invention are combined with a cationic lipid. In one embodiment the cationic lipid is DOTAP (N-[1-(2,3-dioleoyloxy)propy-1]-N,N,N-trimethylammonium methyl-sulfate). DOTAP is believed to transport polymers into cells and specifically traffic to the endosomal compartment, where it can release the polymer in a pH-dependent fashion. Once in the endosomal compartment, the polymers can interact with certain intracellular TLRs, triggering TLR-mediated signal transduction pathways involved in generating an immune response. Other agents with similar properties including trafficking to the endosomal compartment can be used in place of or in addition to DOTAP. Other lipid formulations include, for example, EFFECTENE® (a non-liposomal lipid with a special DNA condensing enhancer) and SUPERFECT® (a novel acting dendrimeric technology), SMARTICLES® (charge reversible particles that become positively charged when they cross cell membranes) and Stable Nucleic Acid Lipid Particles (SNALPs) which employ a lipid bilayer. Liposomes are commercially available from Gibco BRL, for example, as LIPOFECTIN® and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241. In other embodiments the immunostimulatory polymers of the invention are combined with microparticles, cyclodextrins, nanoparticles, noisomes, dendrimers, polycationic peptides, virosomes and virus-like particles, or ISCOM®'s.

In one embodiment the immunostimulatory polymers of the invention are in the form of covalently closed, dumbbell-shaped molecules with both primary and secondary structure. As described below, in one embodiment such cyclic oligoribonucleotides include two single-stranded loops connected by an intervening double-stranded segment. In one embodiment at least one single-stranded loop includes an immunostimulatory RNA motif of the invention. Other covalently closed, dumbbell-shaped molecules of the invention include chimeric DNA:RNA molecules in which, for example, the double-stranded segment is at least partially DNA (e.g., either homodimeric dsDNA or heterodimeric DNA:RNA) and at least one single-stranded loop includes an immunostimulatory RNA motif of the invention. Alternatively, the double-stranded segment of the chimeric molecule is RNA.

In certain embodiments the immunostimulatory polymers are isolated. An isolated molecule is a molecule that is substantially pure and is free of other substances with which it is ordinarily found in nature or in in vivo systems to an extent practical and appropriate for its intended use. In particular, the immunostimulatory polymers are sufficiently pure and are sufficiently free from other biological constituents of cells so as to be useful in, for example, producing pharmaceutical preparations. Because an isolated immunostimulatory polymer of the invention may be admixed with a pharmaceutically acceptable carrier in a pharmaceutical preparation, the immunostimulatory polymer may comprise only a small percentage by weight of the preparation. The immunostimulatory polymer is nonetheless substantially pure in that it has been substantially separated from the substances with which it may be associated in living systems.

For use in the instant invention the immunostimulatory polymers of the invention can be synthesized de novo using or adapted from any of a number of procedures well known in the art. For example, the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed by a variety of automated nucleic acid synthesizers available in the market. Additional synthesis methods useful according to the instant invention are disclosed in Uhlmann E et al. (1990) *Chem Rev* 90:544-84, and Goodchild J (1990) *Bioconjugate Chem* 1:165.

Oligoribonucleotide synthesis can be performed either in solution or on a solid-phase support. In solution, block coupling reactions (dimers, trimers, tetramers, etc.) are preferred, while solid-phase synthesis is preferably performed in a stepwise process using monomeric building blocks. Different chemistries, such as the phosphotriester method, H-phosphonate method, and phosphoramidite method, have been described (Eckstein F (1991) *Oligonucleotides and Ana-* logues, *A Practical Approach,* IRL Press, Oxford). While in the phosphotriester method the reactive phosphorus group is in the oxidation state +V, the more reactive Phosphor +III derivatives are used in the coupling reactions according to the phosphoramidite and H-phosphonate approaches. In the latter two approaches, phosphorus is oxidized after the coupling step to yield the stable P(V) derivatives. If the oxidizer is iodine/water/base, then phosphodiesters are obtained after deprotection. In contrast, if the oxidizer is a sulfurizing agent, such as Beaucage's Reagent, then phosphorothioates are obtained after deprotection.

An efficient method for oligoribonucleotide synthesis is the combination of solid-support synthesis using phosphoramidite chemistry as originally described for oligodeoxynucleotides by Matteucci and Caruthers. Matteucci M D et al. (1981) *J Am Chem Soc* 103:3185.

Synthesis of oligoribonucleotides is similar to oligodeoxynucleotides, with the difference that the 2'-hydroxy group present in oligoribonucleotides must be protected by a suitable hydroxy protecting group. The monomers can be protected e.g. by 2'-O-t-butyldimethylsilyl (TBDMS) group in the RNA monomeric building blocks. However, RNA synthesis using monomers containing the 2'-O-TriisopropylsilylOxyMethyl (TOM) group (TOM-Protecting-Group™) has been reported to yield higher coupling efficiency, because the TOM-Protecting-Group exhibits lower steric hindrance than the TBDMS group. While the TBDMS protecting group is removed using fluoride, fast deprotection is achieved for the TOM group using methylamine in ethanol/water at room temperature. In oligo(ribo)nucleotide synthesis, chain elongation from 3'- to 5'-end is preferred, which is achieved by coupling of a ribonucleotide unit having a 3'-phosphor (III) group or its activated derivative to a free 5'-hydroxy group of another nucleotide unit.

Synthesis can be conveniently performed using an automated DNA/RNA synthesizer. Thereby, synthesis cycles as recommended by the suppliers of the synthesizers can be used. For ribonucleoside phosphoramidite monomers, coupling times are longer (e.g., 400 sec) as compared to deoxynucleoside monomers. As solid support, 500 to 1000 Å controlled pore glass (CPG) support or organic polymer support, such as primer support PS200 (Amersham), can be used. The solid support usually contains the first nucleoside, such as 5'-O-Dimethoxytrityl-N-6-benzoyladenosine, attached via its 3'-end. After cleavage of the 5'-O-Dimethoxytrityl-group with trichloroacetic acid, chain elongation is achieved using e.g. 5'-O-Dimethoxytrityl-N-protected-2'-O-tert butyldimethylsilyl-nucleoside-3'-O-phosphoramidites. After successive repetitive cycles, the completed oligoribonucleotide is cleaved from the support and deprotected by treatment with concentrated ammonia/ethanol (3:1, v:v) for 24 hours at 30° C. The TBDMS blocking group is finally cleaved off using triethylamine/HF. The crude oligoribonucleotides can be purified by ion exchange high pressure liquid chromatography (HPLC), ion-pair reverse phase HPLC, or polyacrylamide gel electrophoresis (PAGE) and characterized by mass spectrometry.

Synthesis of 5'-conjugates is straightforward by coupling a phosphoramidite of the molecule to be ligated to the 5'-hydroxy group of the terminal nucleotide in solid-phase synthesis. A variety of phosphoramidite derivatives of such ligands, such as cholesterol, acridine, biotin, psoralene, ethyleneglycol, or aminoalkyl residues are commercially available. Alternatively, aminoalkyl functions can be introduced during solid-phase synthesis which allow post-synthesis derivatization by activated conjugate molecules, such as active esters, isothiocynates, or iodo-acetamides.

Synthesis of 3'-end conjugates is usually achieved by using the correspondingly modified solid supports, such as e.g. commercially available cholesterol-derivatized solid supports. Conjugation can however also be done at internucleotide linkages, nucleobases or at the ribose residues, such as at the 2'-position of ribose.

For cyclic oligoribonucleotides, the elongation of the oligonucleotide chain can be carried out on Nucleotide PS solid support (Glen Research) using standard phosphoramidite chemistry. The cyclization reaction is then carried out on the solid support using a phosphotriester coupling procedure (Alazzouzi et al. (1997) *Nucleosides Nucleotides* 16:1513-14). On final deprotection with ammonium hydroxide, virtually the only product which comes into solution is the desired cyclic oligonucleotide.

Cyclic oligoribonucleotides of the invention include closed circular forms of RNA and can include single-stranded RNA with or without double-stranded RNA. For example, in one embodiment the cyclic oligoribonucleotide includes double-stranded RNA and takes on a dumbbell conformation with two single-stranded loops connected by an intervening double-stranded segment. Covalently closed, dumbbell-shaped CpG oligodeoxynucleotides have been described in U.S. Pat. No. 6,849,725. In another embodiment the cyclic oligoribonucleotide includes double-stranded RNA and takes on a conformation with three or more single-stranded loops connected by intervening double-stranded segments. In one embodiment an immunostimulatory RNA motif is located in one or more single-stranded segments.

The immunostimulatory polymers of the invention are useful, alone or in combination with other agents, such as adjuvants. An adjuvant as used herein refers to a substance other than an antigen that enhances immune cell activation in response to an antigen, e.g., a humoral and/or cellular immune response. Adjuvants promote the accumulation and/or activation of accessory cells to enhance antigen-specific immune responses. Adjuvants are used to enhance the efficacy of vaccines, i.e., antigen-containing compositions used to induce protective immunity against the antigen.

Adjuvants can work through two general mechanisms and a given adjuvant or adjuvant formulation may act by one or both mechanisms. The first mechanism is to physically influence the distribution of the antigen to cells or sites where antigen-specific immune responses develop, and this can be a delivery vehicle that changes the biodistribution of the antigen, including targeting to specific areas or cell types, or creates a depot effect such that the antigen is slowly released in the body, thus prolonging the exposure of immune cells to the antigen.

This class of adjuvants includes but is not limited to alum (e.g., aluminum hydroxide, aluminum phosphate); emulsion-based formulations including water-in-oil or oil-in-water-in emulsions made from either mineral or non-mineral oil. These may be oil-in-water emulsions such as Montanide ISA 720 (Seppic, AirLiquide, Paris, France); MF-59 (a squalene-in-water emulsion stabilized with Span 85 and Tween 80; Chiron Corporation, Emeryville, Calif.); and PROVAX (stabilizing detergent and a micelle-forming agent; IDEC Pharmaceuticals Corporation, San Diego, Calif.). These may also be water-in-oil emulsions such as Montanide ISA 50 (oily composition of mannide oleate and mineral oil, Seppic) or Montanide ISA 206 (oily composition of mannide oleate and mineral oil, Seppic).

The second adjuvant mechanism is as an immune response modifier or immune stimulatory agent. These result in activation of immune cells to better present, recognize or respond to antigens, and thus the antigen specific responses are enhanced for kinetics, magnitude, phenotype or memory. Immune response modifiers typically act through specific receptors such as Toll-like receptors or one of several other non-TLR pathways (e.g., RIG-I), however the pathways for some are yet unknown. This class of adjuvants includes but is not limited to saponins purified from the bark of the *Q. saponaria* tree, such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand and *Leishmania* elongation factor (a purified *Leishmania* protein; Corixa Corporation, Seattle, Wash.).

There are many adjuvants that act through TLRs. Adjuvants that act through TLR4 include derivatives of lipopolysaccharides such as monophosphoryl lipid A (MPL; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Flagellin is an adjuvant that acts through TLR5. Double-stranded RNA acts through TLR3. Adjuvants acting through TLR7 and/or TLR8 include single-stranded RNA or oligoribonucleotides (ORN) and synthetic low molecular weight compounds that recognize and activate the TLR including imidazoquinolinamines (e.g., imiquimod, resiquimod; 3M). Adjuvants acting through TLR9 include DNA of viral or bacterial origin, or synthetic oligodeoxynucleotides (ODN), such as CpG ODN.

Adjuvants that have both a physical effect and an immune stimulatory effect are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia), Pam3Cys, SB-AS2 (SmithKline Beecham adjuvant system #2 which is an oil-in-water emulsion containing MPL and QS21: SmithKline Beecham Biologicals [SBB], Rixensart, Belgium), SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Syntex Adjuvant Formulation (SAF, an oil-in-water emulsion containing Tween 80 and a nonionic block copolymer; Syntex Chemicals, Inc., Boulder, Colo.), Montanide IMS (e.g., IMS 1312, water-based nanoparticles combined with a soluble immunostimulant, Seppic) as well as many of the delivery vehicles described below.

Also provided is a composition that includes an immunostimulatory polymer of the invention plus another adjuvant, wherein the other adjuvant is a cationic polysaccharide such as chitosan, or a cationic peptide such as protamine, a polyester, a poly(lactic acid), a poly(glycolic acid), or a copolymer of one or more of the above.

Also provided is a composition that includes an immunostimulatory polymer of the invention plus another adjuvant, wherein the other adjuvant is a cytokine. In one embodiment the composition is a conjugate of the immunostimulatory polymer of the invention and the cytokine.

Cytokines are soluble proteins and glycoproteins produced by many types of cells that mediate inflammatory and immune reactions. Cytokines mediate communication between cells of the immune system, acting locally as well as systemically to recruit cells and to regulate their function and proliferation. Categories of cytokines include mediators and regulators of innate immunity, mediators and regulators of adaptive immunity, and stimulators of hematopoiesis. Included among cytokines are interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, and interleukins 19-32 (IL-19-IL-32), among others), chemokines (e.g., IP-10, RANTES, MIP-1α, MIP-1β, MIP-3a, MCP-1, MCP-2, MCP-3, MCP-4, eotaxin, I-TAC, and BCA-1, among others), as well as other cytokines including type 1 interferons (e.g., IFN-α and IFN-β), type 2 interferon (e.g., IFN-γ), tumor necrosis factor-alpha (TNF-α), transforming growth factor-beta (TGF-β), and various colony stimulating factors (CSFs), including GM-CSF, G-CSF, and M-CSF.

Also provided is a composition that includes an immunostimulatory polymer of the invention plus an immunostimulatory CpG nucleic acid. In one embodiment the composition is a conjugate of the immunostimulatory polymer of the invention and the CpG nucleic acid, e.g. a RNA:DNA conjugate.

An immunostimulatory CpG nucleic acid as used herein refers to a natural or synthetic DNA sequence that includes a CpG motif and that stimulates activation or proliferation of cells of the immune system. Immunostimulatory CpG nucleic acids have been described in a number of issued patents, published patent applications, and other publications, including U.S. Pat. Nos. 6,194,388; 6,207,646; 6,214,806; 6,218,371; 6,239,116; and 6,339,068. In one embodiment the immunostimulatory CpG nucleic acid is a CpG oligodeoxynucleotide (CpG ODN) 6-100 nucleotides long. In one embodiment the immunostimulatory CpG nucleic acid is a CpG oligodeoxynucleotide (CpG ODN) 8-nucleotides long.

In some embodiments the polymer includes a CG dinucleotide. In other embodiments the polymer is free of a CG dinucleotide.

Immunostimulatory CpG nucleic acids include different classes of CpG nucleic acids. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The A class CpG nucleic acids typically have a palindromic phosphodiester CpG dinucleotide-containing sequence of at least 6 nucleotides and stabilized poly-G sequences at either or both the 5' and 3' ends. See, for example, published international patent application WO 01/22990. Yet another class of CpG nucleic acids activates B cells and NK cells and induces IFN-α; this class has been termed the C class. The C class CpG nucleic acids, as first characterized, typically are fully stabilized, include a B class-type sequence and a GC-rich palindrome or near-palindrome. This class has been described in published U.S. patent application 2003/0148976, the entire contents of which are incorporated herein by reference.

Immunostimulatory CpG nucleic acids also include so-called soft and semi-soft CpG nucleic acids, as disclosed in published U.S. patent application 2003/0148976, the entire contents of which is incorporated herein by reference. Such soft and semi-soft immunostimulatory CpG nucleic acids incorporate a combination of nuclease-resistant and nuclease-sensitive internucleotide linkages, wherein the different types of linkages are positioned according to certain rules.

The invention in one aspect provides a vaccine that includes an immunostimulatory polymer of the invention and an antigen. An "antigen" as used herein refers to any molecule capable of being recognized by a T-cell antigen receptor or B-cell antigen receptor. The term broadly includes any type of molecule which is recognized by a host immune system as being foreign. Antigens generally include but are not limited to, cells, cell extracts, proteins, polypeptides, peptides, polysaccharides, polysaccharide conjugates, peptide and non-peptide mimics of polysaccharides and other molecules, small molecules, lipids, glycolipids, polysaccharides, carbohydrates, viruses and viral extracts, and multicellular organisms such as parasites, and allergens. With respect to antigens that are proteins, polypeptides, or peptides, such antigens can include nucleic acid molecules encoding such antigens. Antigens more specifically include, but are not limited to, cancer antigens, which include cancer cells and molecules expressed in or on cancer cells; microbial antigens, which include microbes and molecules expressed in or on microbes; allergens, and other disease-associated molecules such as autoreactive T cells. Accordingly, the invention in certain embodiments provides vaccines for cancers, infectious diseases, allergy, addition, diseases caused by abnormally folded proteins, autoimmune disease, and cholesterol management.

A vaccine against infectious disease can be prophylactic or therapeutic. The antigen in the vaccine can be whole live (attenuated), whole killed/inactivated, recombinant live attenuated, subunit purified, subunit recombinant, or a peptide. The vaccine can further comprise additional adjuvants or combinations of adjuvants. The additional adjuvants can be those that have a depot effect (e.g. alum), and immune modifier (e.g. either another TLR agonist or one that works through a non-TLR pathway), or an adjuvant that has both these effects such as an immune stimulating complex (ISCOM®). Adjuvants are described in more detail below.

A vaccine against cancer can also be prophylactic or therapeutic. The cancer antigen can be whole cell (individual DC vaccine), or one or more polypeptides or peptides. These are typically attached to carrier molecule. The vaccine can further comprise additional adjuvants or combinations of adjuvants such as those described above. Cancer antigens are discussed in more detail below.

For a vaccine for treating allergy the antigen is the allergen or part of the allergen. The allergen may be either contained within or attached to the delivery vehicle. The allergen may be linked to the immune stimulatory polymer. Allergens are discussed in more detail below.

Vaccines for treating addiction may be useful for treating e.g. nicotine addiction, cocaine addiction, methamphetamine, or heroin addiction. The addictive molecule in these cases is the native molecule or a hapten. "Antigens" for inclusion in vaccines against addiction are typically small molecules and may be conjugated to a carrier protein or other carrier particle, or they may be incorporated into a virus-like particle.

Vaccines to treat diseases caused by abnormally folded proteins may be useful for treating diseases such as transmissible spongiform encephalopathy (a variant of Creutzfeld-Jakob disease). The "antigen" in this case would be the scrapie prion, which could be attached to a carrier protein or a live attenuated vector. One example of a vaccine against Alzheimer's disease would be, for example, a vaccine targeted to the beta-amyloid peptide or protein.

Vaccines to treat autoimmune diseases are also provided. These vaccines could be useful for treating autoimmune diseases in which the molecule that the autoimmune cells recognize has been identified. For example, a vaccine against autoreactive T cells that respond to myelin would be used to treat multiple sclerosis.

Vaccines useful for treating cardiovascular diseases and conditions are also provided. The vaccine may target a molecule known to contribute to the etiology of the disease, such as lipoproteins, cholesterol, and molecules involved in cholesterol metabolism. A vaccine for managing cholesterol would comprise, for example, cholesteryl ester transfer protein (CETP) as an antigen. CETP facilitates the exchange of cholesterol from anti-atherogenic apo A-I-containing HDL particles to the atherogenic apo B-containing VLDL and LDL. Such a vaccine could be used to treat high cholesterol or slow the progression of atherosclerosis. The vaccine may be used to treat other cardiovascular diseases and conditions in which a target molecule is known.

The invention in one aspect provides a use of an immunostimulatory polymer of the invention for the preparation of a medicament for vaccinating a subject.

The invention in one aspect provides a method for preparing a vaccine. The method includes the step of placing an immunostimulatory polymer of the invention in intimate association with an antigen and, optionally, a pharmaceutically acceptable carrier.

In some embodiments the immunostimulatory polymer and the antigen or allergen are conjugated. The antigen and the immunostimulatory polymer may be conjugated directly, or they may be conjugated indirectly by means of a linker.

A "microbial antigen" as used herein is an antigen of a microorganism and includes but is not limited to viruses, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. In some aspects, the invention also intends to treat diseases in which prions are implicated in disease progression such as for example bovine spongiform encephalopathy (i.e., mad cow disease, BSE) or scrapie infection in animals, or Creutzfeldt-Jakob disease in humans.

Viruses include, but are not limited to, enteroviruses (including, but not limited to, viruses that the family picornaviridae, such as polio virus, Coxsackie virus, echo virus), rotaviruses, adenovirus, and hepatitis virus, such as hepatitis A, B, C, D and E. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and other viruses acute laryngotracheobronchitis virus, Alphavirus, Kaposi's sarcoma-associated herpesvirus, Newcastle disease virus, Nipah virus, Norwalk virus, papillomavirus, parainfluenza virus, avian influenza, SARs virus, West Nile virus.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (coccus), straight-rod (bacillus) and curved or spiral rod (vibrio, campylobacter, spirillum, and spirochaete). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counter-stain and thus appear pink.

Infectious bacteria include, but are not limited to, gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borrelia burgdorferi, Legionella pneumophilia, Mycobacteria* sps (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Rickettsia*, and *Actinomyces israelii*.

Parasites are organisms which depend upon other organisms in order to survive and thus must enter, or infect, another organism to continue their life cycle. The infected organism, i.e., the host, provides both nutrition and habitat to the parasite. Although in its broadest sense the term parasite can include all infectious agents (i.e., bacteria, viruses, fungi, protozoa and helminths), generally speaking, the term is used to refer solely to protozoa, helminths, and ectoparasitic arthropods (e.g., ticks, mites, etc.). Protozoa are single-celled organisms which can replicate both intracellularly and extracellularly, particularly in the blood, intestinal tract or the extracellular matrix of tissues. Helminths are multicellular organisms which almost always are extracellular (an exception being *Trichinella* spp.). Helminths normally require exit from a primary host and transmission into a secondary host in order to replicate. In contrast to these aforementioned classes, ectoparasitic arthropods form a parasitic relationship with the external surface of the host body.

Parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense* and *Schistosoma mansoni*. Fungi are eukaryotic organisms, only a few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory allergies following inhalation of fungal antigens, fungal intoxication due to ingestion of toxic substances, such as *Amanita phalloides* toxin and phallotoxin produced by poisonous mushrooms and aflatoxins, produced by *aspergillus* species, not all fungi cause infectious disease.

Infectious fungi can cause systemic or superficial infections. Primary systemic infection can occur in normal healthy subjects, and opportunistic infections are most frequently found in immunocompromised subjects. The most common fungal agents causing primary systemic infection include *Blastomyces, Coccidioides*, and *Histoplasma*. Common fungi causing opportunistic infection in immunocompromised or immunosuppressed subjects include, but are not limited to, *Candida albicans, Cryptococcus neoformans*, and various *Aspergillus* species. Systemic fungal infections are invasive infections of the internal organs. The organism usually enters the body through the lungs, gastrointestinal tract, or intravenous catheters. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, disseminated *Penicillium marneffei*, phaeohyphomycosis, rhinosporidioisis, sporotrichosis, and zygomycosis.

Other medically relevant microorganisms have been described extensively in the literature, e.g., see C. G. A. Thomas, *Medical Microbiology*, Bailliere Tindall, Great Britain 1983, the entire contents of which is hereby incorporated by reference. Each of the foregoing lists is illustrative and is not intended to be limiting.

As used herein, the terms "cancer antigen" and "tumor antigen" are used interchangeably to refer to a compound, such as a peptide, protein, or glycoprotein, which is associated with a tumor or cancer cell and which is capable of provoking an immune response when expressed on the surface of an antigen-presenting cell in the context of a major histocompatibility complex (MHC) molecule. Cancer antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation, and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Cancer antigens can be prepared from cancer cells either by preparing crude extracts of cancer cells, for example, as described in Cohen P A et al. (1994) Cancer Res 54:1055-8, by partially purifying the antigens, by recombinant technology, or by de novo synthesis of known antigens. Cancer antigens include but are not limited to antigens that are recombinantly expressed, an immunogenic portion of, or a whole tumor or cancer or to cell thereof. Such antigens can be isolated or prepared recombinantly or by any other means known in the art.

Examples of tumor antigens include MAGE, MART-1/Melan-A, gp00, dipeptidyl peptidase IV (DPPIV), adenosine deaminase-binding protein (ADAbp), cyclophilin b, colorectal associated antigen (CRC)—C017-1A/GA733, carcinoembryonic antigen (CEA) and its immunogenic epitopes CAP-1 and CAP-2, etv6, aml1, prostate specific antigen (PSA) and its immutiogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp00$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, Smad family of tumor antigens, imp-1, P A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2. This list is not meant to be limiting.

An "allergen" as used herein is a molecule capable of provoking an immune response characterized by production of IgE. An allergen is also a substance that can induce an allergic or asthmatic response in a susceptible subject. Thus, in the context of this invention, the term allergen means a specific type of antigen which can trigger an allergic response which is mediated by IgE antibody.

The list of allergens is enormous and can include pollens, insect venoms, animal dander dust, fungal spores and drugs (e.g., penicillin). Examples of natural animal and plant allergens include proteins specific to the following genuses: *Canis* (*Canis familiaris*); *Dermatophagoides* (e.g., *Dermatophagoides farinae*); *Felis* (*Felis domesticus*); *Ambrosia* (*Ambrosia artemisiifolia*); *Lolium* (e.g., *Loliumperenne* and *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea tropa*); *Artemisia* (*Artemisia vulgaris*); *Plantago* (e.g., *Plantago lanceolata*); *Parietaria* (e.g., *Parietaria officinalis* and *Parietaria judaica*); *Blattella* (e.g., *Blattella germanica*); *Apis* (e.g., *Apis multiflorum*); *Cupressus* (e.g., *Cupressus sempervirens, Cupressus arizofnica* and *Cupressus macrocarpa*); *Juniperus* (e.g., *Juniperus sabinoides, Juniperus virginiana, Juniperus communis*, and *Juniperus ashei*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* and *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*).

The invention in one aspect provides a conjugate of an immunostimulatory polymer of the invention and an antigen. In one embodiment the immunostimulatory polymer of the invention is covalently linked to the antigen. The covalent linkage between the immunostimulatory polymer and the antigen can be any suitable type of covalent linkage, provided the immunostimulatory polymer and the antigen when so joined retain measurable functional activity of each individual component. In one embodiment the covalent linkage is direct. In another embodiment the covalent linkage is indirect, e.g., through a linker moiety. The covalently linked immunostimulatory polymer and antigen may be processed within a cell to release one from the other. In this way delivery to a cell of either component may be enhanced compared to its delivery if administered as a separate preparation or separate component. In one embodiment the antigen is an antigen per se, i.e., it is a preformed antigen.

In one aspect the invention provides a pharmaceutical composition which includes a composition of the invention, in association with a delivery vehicle. In various embodiments the delivery vehicle can be chosen from a cationic lipid, a liposome, a cochleate, a virosome, an immune-stimulating complex (ISCOM®), a microparticle, a microsphere, a nanosphere, a unilamellar vesicle (LUV), a multilamellar vesicle, an emulsome, and a polycationic peptide, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle (such as a nanosphere or a nanocapsule), a polymeric microparticle (such as a microsphere or a microcapsule), a chitosan, a cyclodextrin, a niosome, or an ISCOM® and, optionally, a pharmaceutically acceptable carrier.

Pharmaceutically acceptable carriers are discussed below. The pharmaceutical composition of the invention optionally can further include an antigen. The composition of the invention, along with the antigen when present, is brought into physical association with the delivery vehicle using any suitable method. The immunostimulatory composition can be contained within the delivery vehicle, or it can be present on or in association with a solvent-exposed surface of the delivery vehicle. In one embodiment the immunostimulatory polymer is present on or in association with a solvent-exposed surface of the delivery vehicle, and the antigen, if present, is contained within the delivery vehicle. In another embodiment both the immunostimulatory polymer and the antigen are present on or in association with a solvent-exposed surface of the delivery vehicle. In yet another embodiment the antigen is present on or in association with a solvent-exposed surface of the delivery vehicle, and the immunostimulatory polymer is contained within the delivery vehicle. In yet another embodiment both the immunostimulatory polymer and the antigen, if antigen is included, are contained within the delivery vehicle.

The invention also provides methods for use of the immunostimulatory compositions of the invention. In one aspect the invention provides a method of activating an immune cell. The method according to this aspect of the invention includes the step of contacting an immune cell, in vitro or in vivo, with an effective amount of a composition of the invention, to activate the immune cell. The composition of the invention can optionally include an antigen. An "immune cell" as used herein refers to any bone marrow-derived cell that can participate in an innate or adaptive immune response. Cells of the immune system include, without limitation, dendritic cells (DC), natural killer (NK) cells, monocytes, macrophages, granulocytes, B lymphocytes, plasma cells, T lymphocytes, and precursor cells thereof. In one embodiment the immune cell is an immune cell capable of producing IFN-α, e.g., a plasmacytoid dendritic cell (pDC). In some embodiments the immune cell is a TLR7 expressing cell. In the context of this invention, the method does not include formulation with lipofectin in an amount effective to induce therapeutically significant IFN-α production. In one embodiment, the immune cells do not produce therapeutically significant amounts of TNF-α in response to the polymer.

As used herein, the term "effective amount" refers to that amount of a substance which is necessary or sufficient to bring about a desired biological effect. An effective amount can but need not be limited to an amount administered in a single administration. In one embodiment the compositions of the invention may be used to activate an immune cell by inducing an immune cell to enter an activated state that is associated with an immune response. Activating an immune cell refers both to inducing and augmenting an immune response. As used herein, the term "immune response" refers to any aspect of an innate or adaptive immune response that reflects activation of an immune cell to proliferate, to perform an effector immune function, or to produce a gene product involved in an immune response. Gene products involved in an immune response can include secreted products (e.g., antibodies, cytokines, and chemokines) as well as intracellular and cell surface molecules characteristic of immune function (e.g., certain cluster of differentiation (CD) antigens, transcription factors, and gene transcripts). The term "immune response" can be applied to a single cell or to a population of cells.

Production of cytokines can be assessed by any of several methods well known in the art, including biological response assays, enzyme-linked immunosorbent assay (ELISA), intracellular fluorescence-activated cell sorting (FACS) analysis, and reverse transcriptase/polymerase chain reaction (RT-PCR). In one embodiment the immune response involves production of IFN-α.

In one embodiment the immune response involves upregulation of cell surface markers of immune cell activation, such as CD25, CD80, CD86, and CD154. Methods for measuring cell surface expression of such markers are well known in the art and include FACS analysis.

For measurement of immune response in a cell or population of cells, in one embodiment the cell or population of cells expresses TLR7. The cell can express the TLR naturally, or it can be manipulated to express the TLR though introduction into the cell of a suitable expression vector for the TLR. In one embodiment the cell or population of cells is obtained as peripheral blood mononuclear cells (PBMC). In one embodiment the cell or population of cells is obtained as a cell line expressing the TLR. In one embodiment the cell or population of cells is obtained as a transient transfectant expressing the TLR. In one embodiment the cell or population of cells is obtained as a stable transfectant expressing the TLR.

Also for use in measuring an immune response in a cell or population of cells, it may be convenient to introduce into the cell or population of cells a reporter construct that is responsive to intracellular signaling by a TLR. In one embodiment such a reporter is a gene placed under the control of an NF-κB promoter. In one embodiment the gene placed under control of the promoter is luciferase. Under suitable conditions of activation, the luciferase reporter construct is expressed and emits a detectable light signal that may be measured quantitatively using a luminometer. Such reporter constructs and other suitable reporter constructs are commercially available.

The invention also contemplates the use of cell-free methods of detecting TLR activation.

The invention in certain aspects relates to compositions and methods for use in therapy. The immunostimulatory compositions of the invention can be used alone or combined with other therapeutic agents. The immunostimulatory composition and other therapeutic agent may be administered simultaneously or sequentially. When the immunostimulatory composition of the invention and the other therapeutic agent are administered simultaneously, they can be administered in the same or separate formulations, but they are administered at the same time. In addition, when the immunostimulatory composition of the invention and the other therapeutic agent are administered simultaneously, they can be administered via the same or separate routes of administration, but they are administered at the same time. The immunostimulatory composition of the invention and another therapeutic agent are administered sequentially when administration of the immunostimulatory composition of the invention is temporally separated from administration of the other therapeutic agent. The separation in time between the administration of these compounds may be a matter of minutes or it may be longer. In one embodiment the immunostimulatory composition of the invention is administered before administration of the other therapeutic agent. In one embodiment the immunostimulatory composition of the invention is administered after administration of the other therapeutic agent. In addition, when the immunostimulatory composition of the invention and the other therapeutic agent are administered sequentially, they can be administered via the same or separate routes of administration. Other therapeutic agents include but are not limited to adjuvants, antigens, vaccines, and medicaments useful for the treatment of infection, cancer, allergy, and asthma.

In one aspect the invention provides a method of vaccinating a subject. The method according to this aspect of the invention includes the step of administering to the subject an antigen and a composition of the invention. In one embodiment the administering the antigen includes administering a nucleic acid encoding the antigen.

A "subject" as used herein refers to a vertebrate animal. In various embodiments the subject is a human, a non-human primate, or other mammal. In certain embodiments the subject is a mouse, rat, guinea pig, rabbit, cat, dog, pig, sheep, goat, cow, or horse.

For use in vaccinating a subject, the composition of the invention in one embodiment includes an antigen. The antigen can be separate from or covalently linked to a polymer of the invention. In one embodiment the composition of the invention does not itself include the antigen. In this embodiment the antigen can be administered to the subject either separately from the composition of the invention, or together with the composition of the invention. Administration that is separate includes separate in time, separate in location or route of administration, or separate both in time and in location or route of administration. When the composition of the invention and the antigen are administered separate in time, the antigen can be administered before or after the composition of the invention. In one embodiment the antigen is administered 48 hours to 4 weeks after administration of the composition of the invention. The method also contemplates the administration of one or more booster doses of antigen alone, composition alone, or antigen and composition, following an initial administration of antigen and composition.

It is also contemplated by the invention that a subject can be prepared for a future encounter with an unknown antigen by administering to the subject a composition of the invention, wherein the composition does not include an antigen. According to this embodiment the immune system of the subject is prepared to mount a more vigorous response to an antigen that is later encountered by the subject, for example through environmental or occupational exposure. Such method can be used, for example, for travellers, medical workers, and soldiers likely to be exposed to microbial agents.

In one aspect the invention provides a method of treating a subject having an infection. The method according to this aspect of the invention includes the step of administering to a subject having an infection an effective amount of the composition of the invention and an infection medicament to treat the subject.

In one aspect the invention provides a use of an immunostimulatory polymer of the invention for the preparation of a medicament for treating an infection in a subject. In one aspect the invention provides a composition useful for the treatment of infection. The composition according to this aspect includes an immunostimulatory polymer of the invention and an infection medicament.

As used herein, the term "treat" as used in reference to a subject having a disease or condition shall mean to prevent, ameliorate, or eliminate at least one sign or symptom of the disease or condition in the subject.

A subject having an infectious disease is a subject that has a disorder arising from the invasion of the subject, superficially, locally, or systemically, by an infectious microorganism. The infectious microorganism can be a virus, bacterium, fungus, or parasite, as described above.

Infection medicaments include but are not limited to antibacterial agents, anti-viral agents, anti-fungal agents and anti-parasitic agents. Phrases such as "anti-infective agent", "antibiotic", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites. Many antibiotics are low molecular weight molecules which are produced as secondary metabolites by cells, such as microorganisms. In general, antibiotics interfere with one or more functions or structures which are specific for the microorganism and which are not present in host cells.

One of the problems with anti-infective therapies is the side effects occurring in the host that is treated with the anti-infective agent. For instance, many anti-infectious agents can kill or inhibit a broad spectrum of microorganisms and are not specific for a particular type of species. Treatment with these types of anti-infectious agents results in the killing of the normal microbial flora living in the host, as well as the infectious microorganism. The loss of the microbial flora can lead to disease complications and predispose the host to infection by other pathogens, since the microbial flora compete with and function as barriers to infectious pathogens. Other side effects may arise as a result of specific or non-specific effects of these chemical entities on non-microbial cells or tissues of the host.

Another problem with widespread use of anti-infectants is the development of antibiotic-resistant strains of microorganisms. Already, vancomycin-resistant *enterococci*, penicillin-resistant *pneumococci*, multi-resistant *S. aureus*, and multi-resistant *tuberculosis* strains have developed and are becoming major clinical problems. Widespread use of anti-infectants will likely produce many antibiotic-resistant strains of bacteria. As a result, new anti-infective strategies will be required to combat these microorganisms.

Antibacterial antibiotics which are effective for killing or inhibiting a wide range of bacteria are referred to as broad-spectrum antibiotics. Other types of antibacterial antibiotics are predominantly effective against the bacteria of the class gram-positive or gram-negative. These types of antibiotics are referred to as narrow-spectrum antibiotics. Other antibiotics which are effective against a single organism or disease and not against other types of bacteria, are referred to as limited-spectrum antibiotics.

Anti-bacterial agents are sometimes classified based on their primary mode of action. In general, anti-bacterial agents are cell wall synthesis inhibitors, cell membrane inhibitors, protein synthesis inhibitors, nucleic acid synthesis or functional inhibitors, and competitive inhibitors. Cell wall synthesis inhibitors inhibit a step in the process of cell wall synthesis, and in general in the synthesis of bacterial peptidoglycan. Cell wall synthesis inhibitors include β-lactam antibiotics, natural penicillins, semi-synthetic penicillins, ampicillin, clavulanic acid, cephalolsporins, and bacitracin.

The β-lactams are antibiotics containing a four-membered β-lactam ring which inhibits the last step of peptidoglycan synthesis. β-lactam antibiotics can be synthesized or natural. The β-lactam antibiotics produced by *penicillium* are the natural penicillins, such as penicillin G or penicillin V. These are produced by fermentation of *Penicillium chrysogenum*. The natural penicillins have a narrow spectrum of activity and are generally effective against *Streptococcus, Gonococcus,* and *Staphylococcus*. Other types of natural penicillins, which are also effective against gram-positive bacteria, include penicillins F, X, K, and O.

Semi-synthetic penicillins are generally modifications of the molecule 6-aminopenicillanic acid produced by a mold. The 6-aminopenicillanic acid can be modified by addition of side chains which produce penicillins having broader spectrums of activity than natural penicillins or various other advantageous properties. Some types of semi-synthetic penicillins have broad spectrums against gram-positive and gram-negative bacteria, but are inactivated by penicillinase. These semi-synthetic penicillins include ampicillin, carbenicillin, oxacillin, azlocillin, mezlocillin, and piperacillin. Other types of semi-synthetic penicillins have narrower activities against gram-positive bacteria, but have developed properties such that they are not inactivated by penicillinase. These include, for instance, methicillin, dicloxacillin, and nafcillin. Some of the broad spectrum semi-synthetic penicillins can be used in combination with β-lactamase inhibitors, such as clavulanic acids and sulbactam. The β-lactamase inhibitors do not have anti-microbial action but they function to inhibit penicillinase, thus protecting the semi-synthetic penicillin from degradation.

Another type of β-lactam antibiotic is the cephalolsporins. They are sensitive to degradation by bacterial β-lactamases, and thus, are not always effective alone. Cephalolsporins, however, are resistant to penicillinase. They are effective against a variety of gram-positive and gram-negative bacteria. Cephalolsporins include, but are not limited to, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, and moxalactam.

Bacitracin is another class of antibiotics which inhibit cell wall synthesis, by inhibiting the release of muropeptide subunits or peptidoglycan from the molecule that delivers the subunit to the outside of the membrane. Although bacitracin is effective against gram-positive bacteria, its use is limited in general to topical administration because of its high toxicity.

Carbapenems are another broad-spectrum β-lactam antibiotic, which is capable of inhibiting cell wall synthesis. Examples of carbapenems include, but are not limited to, imipenems. Monobactams are also broad-spectrum β-lactam antibiotics, and include, euztreonam. An antibiotic produced by *Streptomyces*, vancomycin, is also effective against gram-positive bacteria by inhibiting cell membrane synthesis.

Another class of anti-bacterial agents is the anti-bacterial agents that are cell membrane inhibitors. These compounds disorganize the structure or inhibit the function of bacterial membranes. One problem with anti-bacterial agents that are cell membrane inhibitors is that they can produce effects in eukaryotic cells as well as bacteria because of the similarities in phospholipids in bacterial and eukaryotic membranes. Thus these compounds are rarely specific enough to permit these compounds to be used systemically and prevent the use of high doses for local administration.

One clinically useful cell membrane inhibitor is Polymyxin. Polymyxins interfere with membrane function by binding to membrane phospholipids. Polymyxin is effective mainly against Gram-negative bacteria and is generally used in severe *Pseudomonas* infections or *Pseudomonas* infections that are resistant to less toxic antibiotics. The severe side effects associated with systemic administration of this compound include damage to the kidney and other organs.

Other cell membrane inhibitors include Amphotericin B and Nystatin which are anti-fungal agents used predominantly in the treatment of systemic fungal infections and *Candida* yeast infections. Imidazoles are another class of antibiotic that is a cell membrane inhibitor. Imidazoles are used as anti-bacterial agents as well as anti-fungal agents, e.g., used for treatment of yeast infections, dermatophytic infections, and systemic fungal infections. Imidazoles include but are not limited to clotrimazole, miconazole, ketoconazole, itraconazole, and fluconazole.

Many anti-bacterial agents are protein synthesis inhibitors. These compounds prevent bacteria from synthesizing structural proteins and enzymes and thus cause inhibition of bacterial cell growth or function or cell death. In general these compounds interfere with the processes of transcription or translation. Anti-bacterial agents that block transcription include but are not limited to Rifampins and Ethambutol. Rifampins, which inhibit the enzyme RNA polymerase, have a broad spectrum activity and are effective against gram-positive and gram-negative bacteria as well as *Mycobacterium tuberculosis*. Ethambutol is effective against *Mycobacterium tuberculosis*.

Anti-bacterial agents which block translation interfere with bacterial ribosomes to prevent mRNA from being translated into proteins. In general this class of compounds includes but is not limited to tetracyclines, chloramphenicol, the macrolides (e.g., erythromycin) and the aminoglycosides (e.g., streptomycin).

The aminoglycosides are a class of antibiotics which are produced by the bacterium *Streptomyces*, such as, for instance streptomycin, kanamycin, tobramycin, amikacin, and gentamicin. Aminoglycosides have been used against a wide variety of bacterial infections caused by Gram-positive and Gram-negative bacteria. Streptomycin has been used extensively as a primary drug in the treatment of tuberculosis. Gentamicin is used against many strains of Gram-positive and Gram-negative bacteria, including *Pseudomonas* infections, especially in combination with Tobramycin. Kanamycin is used against many Gram-positive bacteria, including penicillin-resistant *Staphylococci*. One side effect of aminoglycosides that has limited their use clinically is that at dosages which are essential for efficacy, prolonged use has been shown to impair kidney function and cause damage to the auditory nerves leading to deafness.

Another type of translation inhibitor anti-bacterial agent is the tetracyclines. The tetracyclines are a class of antibiotics that are broad-spectrum and are effective against a variety of gram-positive and gram-negative bacteria. Examples of tetracyclines include tetracycline, minocycline, doxycycline, and chlortetracycline. They are important for the treatment of many types of bacteria but are particularly important in the treatment of Lyme disease. As a result of their low toxicity and minimal direct side effects, the tetracyclines have been overused and misused by the medical community, leading to problems. For instance, their overuse has led to widespread development of resistance.

Anti-bacterial agents such as the macrolides bind reversibly to the 50 S ribosomal subunit and inhibit elongation of the protein by peptidyl transferase or prevent the release of uncharged tRNA from the bacterial ribosome or both. These compounds include erythromycin, roxithromycin, clarithromycin, oleandomycin, and azithromycin. Erythromycin is active against most Gram-positive bacteria, *Neisseria, Legionella* and *Haemophilus*, but not against the Enterobacteriaceae. Lincomycin and clindamycin, which block peptide bond formation during protein synthesis, are used against gram-positive bacteria.

Another type of translation inhibitor is chloramphenicol. Chloramphenicol binds the 70 S ribosome inhibiting the bacterial enzyme peptidyl transferase thereby preventing the growth of the polypeptide chain during protein synthesis. One serious side effect associated with chloramphenicol is aplastic anemia. Aplastic anemia develops at doses of chloramphenicol which are effective for treating bacteria in a small proportion (1/50,000) of patients. Chloramphenicol which was once a highly prescribed antibiotic is now seldom uses as a result of the deaths from anemia. Because of its effectiveness it is still used in life-threatening situations (e.g., typhoid fever).

Some anti-bacterial agents disrupt nucleic acid synthesis or function, e.g., bind to DNA or RNA so that their messages cannot be read. These include but are not limited to quinolones and co-trimoxazole, both synthetic chemicals and rifamycins, a natural or semi-synthetic chemical. The quinolones block bacterial DNA replication by inhibiting the DNA gyrase, the enzyme needed by bacteria to produce their circular DNA. They are broad spectrum and examples include norfloxacin, ciprofloxacin, enoxacin, nalidixic acid and temafloxacin. Nalidixic acid is a bactericidal agent that binds to the DNA gyrase enzyme (topoisomerase) which is essential for DNA replication and allows supercoils to be relaxed and reformed, inhibiting DNA gyrase activity. The main use of nalidixic acid is in treatment of lower urinary tract infections (UTI) because it is effective against several types of Gram-negative bacteria such as *E. coli, Enterobacter aerogenes, K. pneumoniae* and *Proteus* species which are common causes of UTI. Co-trimoxazole is a combination of sulfamethoxazole and trimethoprim, which blocks the bacterial synthesis of folic acid needed to make DNA nucleotides. Rifampicin is a derivative of rifamycin that is active against Gram-positive bacteria (including *Mycobacterium tuberculosis* and meningitis caused by *Neisseria meningitidis*) and some Gram-negative bacteria. Rifampicin binds to the beta subunit of the polymerase and blocks the addition of the first nucleotide which is necessary to activate the polymerase, thereby blocking mRNA synthesis.

Another class of anti-bacterial agents is compounds that function as competitive inhibitors of bacterial enzymes. The competitive inhibitors are mostly all structurally similar to a bacterial growth factor and compete for binding but do not perform the metabolic function in the cell. These compounds include sulfonamides and chemically modified forms of sulfanilamide which have even higher and broader antibacterial activity. The sulfonamides (e.g., gantrisin and trimethoprim) are useful for the treatment of *Streptococcus pneumoniae*, beta-hemolytic *streptococci* and *E. coli*, and have been used in the treatment of uncomplicated urinary tract infection (UTI) caused by *E. coli*, and in the treatment of meningococcal meningitis.

Anti-viral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Another category of anti-viral agents are nucleoside analogues. Nucleoside analogues are synthetic compounds which are similar to nucleosides, but which have an incomplete or abnormal deoxyribose or ribose group. Once the nucleoside analogues are in the cell, they are phosphorylated, producing the triphosphate form which competes with normal nucleotides for incorporation into the viral DNA or RNA. Once the triphosphate form of the nucleoside analogue is incorporated into the growing nucleic acid chain, it causes irreversible association with the viral polymerase and thus chain termination. Nucleoside analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

Another class of anti-viral agents includes cytokines such as interferons. The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for antiviral therapy, interferons have severe side effects such as fever, malaise and weight loss.

Immunoglobulin therapy is used for the prevention of viral infection. Immunoglobulin therapy for viral infections is different from bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immune globulin therapy and hyper-immune globulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immunocompromised children and neonates), human rabies immune globulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

Parasiticides are agents that kill parasites directly. Such compounds are known in the art and are generally commercially available. Examples of parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflomithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, timidazole, trimethroprim-sulfamethoxazole, and tryparsamide.

The polymers are also useful for suppressing a Th2-like immune response in a subject. A Th2-type of immune response is characterized at least in part by Th2 cytokines IL-4 and IL-5, as well as antibody isotype switching to IgE. Therefore, suppressing a Th2-like response refers to reduction of the production of Th2 cytokines and other Th2 effects. The polymers can also be used to induce a Th1-like immune response. Th1 and Th2 immune responses are mutually counter-regulatory, so that skewing of the immune response toward a Th1-type of immune response can prevent or ameliorate a Th2-type of immune response.

The polymers can be used for treating and preventing autoimmune disease. Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, prolifeative glomerulonephritis), bullous pemphigoid, Sjögren's syndrome, insulin resistance, and autoimmune diabetes mellitus.

A self-antigen refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the polymer be administered with self antigens, particularly those that are the targets of the autoimmune disorder.

In other instances, the polymer may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

The compositions and methods of the invention can be used alone or in conjunction with other agents and methods useful for the treatment of cancer. In one aspect the invention provides a method of treating a subject having a cancer. The method according to this aspect of the invention includes the step of administering to a subject having a cancer an effective amount of a composition of the invention to treat the subject.

In one aspect the invention provides a method of treating a subject having a cancer. The method according to this aspect of the invention includes the step of administering to a subject having a cancer an effective amount of the composition of the invention and an anti-cancer therapy to treat the subject.

In one aspect the invention provides a use of an immunostimulatory polymer of the invention for the preparation of a medicament for treating cancer in a subject.

In one aspect the invention provides a composition useful for the treatment of cancer. The composition according to this aspect includes an immunostimulatory polymer of the invention and a cancer medicament.

A subject having a cancer is a subject that has detectable cancerous cells. The cancer may be a malignant or non-malignant cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas, adenocarcinomas, and sarcomas.

The immunostimulatory composition of the invention may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCL (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of 3622W94, 4B5, ANA Ab, anti-FLK-2, anti-VEGF, ATRAGEN, AVASTIN (bevacizumab; Genentech), BABS, BEC2, BEXXAR (tositumomab; GlaxoSmithKline), C225, CAMPATH (alemtuzumab; Genzyme Corp.), CEACIDE, CMA 676, EMD-72000, ERBITUX (cetuximab; ImClone Systems, Inc.), Gliomab-H, GNI-250, HERCEPTIN (trastuzumab; Genentech), IDEC-Y2B8, ImmuRAIT-CEA, ior c5, ior egf.r3, ior t6, LDP-03, LymphoCide, MDX-11, MDX-22, MDX-210, MDX-220, MDX-260, MDX-447, MELIMMUNE-1, MELIMMUNE-2, Monopharm-C, NovoMAb-G2, Oncolym, OV103, Ovarex, Panorex, Pretarget, Quadramet, Ributaxin, RITUXAN (rituximab; Genentech), SMART 1D10 Ab, SMART ABL 364 Ab, SMART M195, TNT, and ZENAPAX (daclizumab; Roche), but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

The compositions and methods of the invention can be used alone or in conjunction with other agents and methods useful for the treatment of allergy. In one aspect the invention provides a method of treating a subject having an allergic condition.

The method according to this aspect of the invention includes the step of administering to a subject having an allergic condition an effective amount of a composition of the invention to treat the subject.

In one aspect the invention provides a method of treating a subject having an allergic condition. The method according to this aspect of the invention includes the step of administering to a subject having an allergic condition an effective amount of the composition of the invention and an anti-allergy therapy to treat the subject.

In one aspect the invention provides a use of an immunostimulatory polymer of the invention for the preparation of a medicament for treating an allergic condition in a subject.

In one aspect the invention provides a composition useful for the treatment of an allergic condition. The composition according to this aspect includes an immunostimulatory polymer of the invention and an allergy medicament.

A "subject having an allergic condition" shall refer to a subject that is currently experiencing or has previously experienced an allergic reaction in response to an allergen. An "allergic condition" or "allergy" refers to acquired hypersensitivity to a substance (allergen). Allergic conditions include but are not limited to eczema, allergic rhinitis or coryza, hay fever, allergic conjunctivitis, bronchial asthma, urticaria (hives) and food allergies, other atopic conditions including atopic dermatitis; anaphylaxis; drug allergy; and angioedema.

Allergy is typically an episodic condition associated with the production of antibodies from a particular class of immunoglobulin, IgE, against allergens. The development of an IgE-mediated response to common aeroallergens is also a factor which indicates predisposition towards the development of asthma. If an allergen encounters a specific IgE which is bound to an IgE Fc receptor (FcsR) on the surface of a basophil (circulating in the blood) or mast cell (dispersed throughout solid tissue), the cell becomes activated, resulting in the production and release of mediators such as histamine, serotonin, and lipid mediators.

An allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

Symptoms of an allergic reaction vary, depending on the location within the body where the IgE reacts with the antigen. If the reaction occurs along the respiratory epithelium, the symptoms generally are sneezing, coughing and asthmatic reactions. If the interaction occurs in the digestive tract, as in the case of food allergies, abdominal pain and diarrhea are common. Systemic allergic reactions, for example following a bee sting or administration of penicillin to an allergic subject, can be severe and often life-threatening.

Allergy is associated with a Th2-type of immune response, which is characterized at least in part by Th2 cytokines IL-4 and IL-5, as well as antibody isotype switching to IgE. The immunostimulatory polymers of the invention are useful by themselves to treat a subject having an allergic condition because the immunostimulatory polymers can skew the immune response toward a Th1-type of immune response. Alternatively or in addition, the immunostimulatory polymers of the invention can be used in combination with an allergen to treat a subject having an allergic condition.

The immunostimulatory composition of the invention may also be administered in conjunction with an anti-allergy therapy. Conventional methods for treating or preventing allergy have involved the use of allergy medicaments or desensitization therapies. Some evolving therapies for treating or preventing allergy include the use of neutralizing anti-IgE antibodies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Allergy medicaments include, but are not limited to, antihistamines, corticosteroids, and prostaglandin inducers. Antihistamines are compounds which counteract histamine released by mast cells or basophils. These compounds are well known in the art and commonly used for the treatment of allergy. Anti-histamines include, but are not limited to, acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Corticosteroids include, but are not limited to, methylprednisolone, prednisolone, prednisone, beclomethasone, budesonide, dexamethasone, flunisolide, fluticasone propionate, and triamcinolone. Although dexamethasone is a corticosteroid having anti-inflammatory action, it is not regularly used for the treatment of allergy or asthma in an inhaled form because it is highly absorbed and it has long-term suppressive side effects at an effective dose. Dexamethasone, however, can be used according to the invention for treating allergy or asthma because when administered in combination with a composition of the invention it can be administered at a low dose to reduce the side effects. Some of the side effects associated with corticosteroid use include cough, dysphonia, oral thrush (candidiasis), and in higher doses, systemic effects, such as adrenal suppression, glucose intolerance, osteoporosis, aseptic necrosis of bone, cataract formation, growth suppression, hypertension, muscle weakness, skin thinning, and easy bruising. Barnes & Peterson (1993) *Am Rev Respir Dis* 148:S1-S26; and Kamada A K et al. (1996) *Am J Respir Crit. Care Med* 153:1739-48.

The compositions and methods of the invention can be used alone or in conjunction with other agents and methods useful for the treatment of asthma. In one aspect the invention provides a method of treating a subject having asthma. The method according to this aspect of the invention includes the step of administering to a subject having asthma an effective amount of a composition of the invention to treat the subject. In one aspect the invention provides a method of treating a subject having asthma. The method according to this aspect of the invention includes the step of administering to a subject having asthma an effective amount of the composition of the invention and an anti-asthma therapy to treat the subject.

In one aspect the invention provides a use of an immunostimulatory polymer of the invention for the preparation of a medicament for treating asthma in a subject. In one aspect the invention provides a composition useful for the treatment of asthma. The composition according to this aspect includes an immunostimulatory polymer of the invention and an asthma medicament.

"Asthma" as used herein refers to a disorder of the respiratory system characterized by inflammation and narrowing of the airways, and increased reactivity of the airways to inhaled agents. Asthma is frequently, although not exclusively, associated with an atopic or allergic condition. Symptoms of asthma include recurrent episodes of wheezing, breathlessness, chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, sub-basement membrane fibrosis may occur, leading to persistent abnormalities in lung function.

Research over the past several years has revealed that asthma likely results from complex interactions among inflammatory cells, mediators, and other cells and tissues resident in the airways. Mast cells, eosinophils, epithelial cells, macrophage, and activated T cells all play an important role in the inflammatory process associated with asthma. Djukanovic R et al. (1990) *Am Rev Respir Dis* 142:434-457. It is believed that these cells can influence airway function through secretion of preformed and newly synthesized mediators which can act directly or indirectly on the local tissue. It has also been recognized that subpopulations of T lymphocytes (Th2) play an important role in regulating allergic inflammation in the airway by releasing selective cytokines and establishing disease chronicity. Robinson D S et al. (1992) *N Engl J Med* 326:298-304.

Asthma is a complex disorder which arises at different stages in development and can be classified based on the degree of symptoms as acute, subacute, or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway. A "subject having asthma" is a subject that has a disorder of the respiratory system characterized by inflammation and narrowing of the airways and increased reactivity of the airways to inhaled agents. Factors associated with initiation of asthma include, but are not limited to, allergens, cold temperature, exercise, viral infections, and $SO_2$.

As mentioned above, asthma may be associated with a Th2-type of immune response, which is characterized at least in part by Th2 cytokines IL-4 and IL-5, as well as antibody isotype switching to IgE. Th1 and Th2 immune responses are mutually counter-regulatory, so that skewing of the immune response toward a Th1-type of immune response can prevent or ameliorate a Th2-type of immune response, including allergy. The modified oligoribonucleotide analogs of the invention are therefore useful by themselves to treat a subject having asthma because the analogs can skew the immune response toward a Th1-type of immune response. Alternatively or in addition, the modified oligoribonucleotide analogs of the invention can be used in combination with an allergen to treat a subject having asthma.

The immunostimulatory composition of the invention may also be administered in conjunction with an asthma therapy. Conventional methods for treating or preventing asthma have involved the use of anti-allergy therapies (described above) and a number of other agents, including inhaled agents.

Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and nedocromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. There are many side effects associated with each of these drugs and none of the drugs alone or in combination is capable of preventing or completely treating asthma.

Asthma medicaments include, but are not limited, PDE-4 inhibitors, bronchodilator/beta-2 agonists, K$^+$ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors.

Bronchodilator/$\beta_2$ agonists are a class of compounds which cause bronchodilation or smooth muscle relaxation. Bronchodilator/$\beta_2$ agonists include, but are not limited to, salmeterol, salbutamol, albuterol, terbutaline, D2522/formoterol, fenoterol, bitolterol, pirbuerol methylxanthines and orciprenaline. Long-acting $\beta_2$ agonists and bronchodilators are compounds which are used for long-term prevention of symptoms in addition to the anti-inflammatory therapies. Long-acting $\beta_2$ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. Dose-related acute toxicities are a particular problem with these types of compounds. As a result, routine serum concentration must be monitored in order to account for the toxicity and narrow therapeutic range arising from individual differences in metabolic clearance. Side effects include tachycardia, tachyarrhythmias, nausea and vomiting, central nervous system stimulation, headache, seizures, hematemesis, hyperglycemia and hypokalemia. Short-acting $\beta_2$ agonists include, but are not limited to, albuterol, bitolterol, pirbuterol, and terbutaline. Some of the adverse effects associated with the administration of short-acting $\beta_2$ agonists include tachycardia, skeletal muscle tremor, hypokalemia, increased lactic acid, headache, and hyperglycemia.

Chromolyn sodium and nedocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from inosineophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratropium bromide. These compounds reverse only cholinerigically-mediated bronchospasm and do not modify any reaction to antigen. Side effects include drying of the mouth and respiratory secretions, increased wheezing in some individuals, and blurred vision if sprayed in the eyes.

The immunostimulatory polymers of the invention may also be useful for treating airway remodeling. Airway remodeling results from smooth muscle cell proliferation and/or submucosal thickening in the airways, and ultimately causes narrowing of the airways leading to restricted airflow. The immunostimulatory polymers of the invention may prevent further remodeling and possibly even reduce tissue build-up resulting from the remodeling process.

The immunostimulatory polymers of the invention are also useful for improving survival, differentiation, activation and maturation of dendritic cells. The immunostimulatory oligoribonucleotides have the unique capability to promote cell survival, differentiation, activation and maturation of dendritic cells.

Immunostimulatory polymers of the invention also increase natural killer cell lytic activity and antibody-dependent cellular cytotoxicity (ADCC). ADCC can be performed using an immunostimulatory polymers in combination with an antibody specific for a cellular target, such as a cancer cell. When the immunostimulatory polymer is administered to a subject in conjunction with the antibody, the subject's immune system is induced to kill the tumor cell. The antibodies useful in the ADCC procedure include antibodies which interact with a cell in the body. Many such antibodies specific for cellular targets have been described in the art and many are commercially available. In one embodiment the antibody is an IgG antibody.

In certain aspects the invention provides a method for enhancing epitope spreading. "Epitope spreading" as used herein refers to the diversification of epitope specificity from an initial focused, dominant epitope-specific immune response, directed against a self or foreign protein, to sub-dominant and/or cryptic epitopes on that protein (intramolecular spreading) or other proteins (intermolecular spreading). Epitope spreading results in multiple epitope-specific immune responses.

The immune response consists of an initial magnification phase, which can either be deleterious, as in autoimmune disease, or beneficial, as in vaccinations, and a later down-regulatory phase to return the immune system to homeostasis and generate memory. Epitope spreading may be an important component of both phases. The enhancement of epitope spreading in the setting of a tumor allows the subject's immune system to determine additional target epitopes, not initially recognized by the immune system in response to an original therapeutic protocol, while reducing the possibility of escape variants in the tumor population and thus affect progression of disease.

The oligoribonucleotides of the invention may be useful for promoting epitope spreading in therapeutically beneficial indications such as cancer, viral and bacterial infections, and allergy. The method in one embodiment includes the steps of administering a vaccine that includes an antigen and an adjuvant to a subject and subsequently administering to the subject at least two doses of immunostimulatory polymers of the invention in an amount effective to induce multiple epitope-specific immune responses. The method in one embodiment includes the steps of administering a vaccine that includes a tumor antigen and an adjuvant to a subject and subsequently administering to the subject at least two doses of immunostimulatory polymers of the invention in an amount effective to induce multiple epitope-specific immune responses. The method in one embodiment involves applying a therapeutic protocol which results in immune system antigen exposure in a subject, followed by at least two administrations of an immunostimulatory oligoribonucleotide of the invention, to induce multiple epitope-specific immune responses, i.e., to promote epitope spreading. In various embodiments the therapeutic protocol is surgery, radiation, chemotherapy, other cancer medicaments, a vaccine, or a cancer vaccine.

The therapeutic protocol may be implemented in conjunction with an immunostimulant, in addition to the subsequent immunostimulant therapy. For instance, when the therapeutic protocol is a vaccine, it may be administered in conjunction with an adjuvant. The combination of the vaccine and the adjuvant may be a mixture or separate administrations, i.e., injections (i.e., same drainage field). Administration is not necessarily simultaneous. If non-simultaneous injection is used, the timing may involve pre-injection of the adjuvant followed by the vaccine formulation.

After the therapeutic protocol is implemented, immunostimulant monotherapy begins. The optimized frequency, duration, and site of administration will depend on the target and other factors, but may for example be a monthly to bi-monthly administration for a period of six months to two years. Alternatively the administration may be on a daily, weekly, or biweekly basis, or the administration may be multiple times during a day, week or month. In some instances, the duration of administration may depend on the length of therapy, e.g., it may end after one week, one month, after one year, or after multiple years. In other instances the monotherapy may be continuous as with an intravenous drip. The immunostimulant may be administered to a drainage field common to the target.

For use in therapy, different doses may be necessary for treatment of a subject, depending on activity of the compound, manner of administration, purpose of the immunization (i.e., prophylactic or therapeutic), nature and severity of the disorder, age and body weight of the subject. The administration of a given dose can be carried out both by single administration in the form of an individual dose unit or else several smaller dose units. Multiple administration of doses at specific intervals of weeks or months apart is usual for boosting antigen-specific immune responses.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day.

The pharmaceutical compositions containing nucleic acids and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed herein. For use in therapy, an effective amount of the nucleic acid and/or other therapeutic agent can be administered to a subject by any mode that delivers the agent to the desired surface, e.g., mucosal, systemic.

Administering the pharmaceutical composition of the present invention may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal.

For the treatment or prevention of asthma or allergy, such compounds are preferably inhaled, ingested or administered by systemic routes. Systemic routes include oral and parenteral. Inhaled medications are preferred in some embodiments because of the direct delivery to the lung, the site of inflammation, primarily in asthmatic patients. Several types of devices are regularly used for administration by inhalation. These types of devices include metered dose inhalers (MDI), breath-actuated MDI, dry powder inhaler (DPI), spacer/holding chambers in combination with MDI, and nebulizers.

The therapeutic agents of the invention may be delivered to a particular tissue, cell type, or to the immune system, or both, with the aid of a vector. In its broadest sense, a "vector" is any vehicle capable of facilitating the transfer of the compositions to the target cells. The vector generally transports the immunostimulatory nucleic acid, antibody, antigen, and/or disorder-specific medicament to the target cells with reduced degradation relative to the extent of degradation that would result in the absence of the vector.

In general, the vectors useful in the invention are divided into two classes: biological vectors and chemical/physical vectors. Biological vectors and chemical/physical vectors are useful in the delivery and/or uptake of therapeutic agents of the invention.

Most biological vectors are used for delivery of nucleic acids and this would be most appropriate in the delivery of therapeutic agents that are or that include immunostimulatory nucleic acids.

In addition to the biological vectors discussed herein, chemical/physical vectors may be used to deliver therapeutic agents including immunostimulatory nucleic acids, antibodies, antigens, and disorder-specific medicaments. As used herein, a "chemical/physical vector" refers to a natural or synthetic molecule, other than those derived from bacteriological or viral sources, capable of delivering the nucleic acid and/or other medicament.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules. RNA, DNA and intact virions can be encapsulated within the aqueous interior and be delivered to cells in a biologically active form. Fraley et al. (1981) *Trends Biochem Sci* 6:77.

Liposomes may be targeted to a particular tissue by coupling the liposome to a specific ligand such as a monoclonal antibody, sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. In still other embodiments, the liposome may be targeted to the cancer by coupling it to a one of the immunotherapeutic antibodies discussed earlier. Additionally, the vector may be coupled to a nuclear targeting peptide, which will direct the vector to the nucleus of the host cell.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

Certain cationic lipids, including in particular N-[1-(2,3 dioleoyloxy)-propyl]-N,N,N-trimethylammonium methylsulfate (DOTAP), appear to be especially advantageous when combined with the modified oligoribonucleotide analogs of the invention.

In one embodiment, the vehicle is a biocompatible microparticle or implant that is suitable for implantation or administration to the mammalian recipient. Exemplary bioerodible implants that are useful in accordance with this method are described in PCT International application no. PCT/US/03307 (Publication No. WO95/24929, entitled "Polymeric Gene Delivery System". PCT/US/0307 describes a biocompatible, preferably biodegradable polymeric matrix for containing an exogenous gene under the control of an appropriate promoter. The polymeric matrix can be used to achieve sustained release of the therapeutic agent in the subject.

The polymeric matrix preferably is in the form of a microparticle such as a microsphere (wherein the nucleic acid and/or the other therapeutic agent is dispersed throughout a solid polymeric matrix) or a microcapsule (wherein the nucleic acid and/or the other therapeutic agent is stored in the core of a polymeric shell). Other forms of the polymeric matrix for containing the therapeutic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nucleic acid and/or the other therapeutic agent are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some preferred embodiments, the nucleic acid are administered to the subject via an implant while the other therapeutic agent is administered acutely. Biocompatible microspheres that are suitable for delivery, such as oral or mucosal delivery, are disclosed in Chickering et al. (1996) *Biotech Bioeng* 52:96-101 and Mathiowitz E et al. (1997) Nature 386:410-414 and PCT Pat. Application WO97/03702.

Both non-biodegradable and biodegradable polymeric matrices can be used to deliver the nucleic acid and/or the other therapeutic agent to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable, particularly for the nucleic acid agents. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

If the therapeutic agent is a nucleic acid, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver a nucleic acid in a form that is more efficiently taken up by the cell or, more preferably, in combination with one or more of the above-described vectors.

Other exemplary compositions that can be used to facilitate uptake of a nucleic acid include calcium phosphate and other chemical mediators of intracellular transport, microinjection compositions, electroporation and homologous recombination compositions (e.g., for integrating a nucleic acid into a preselected location within the target cell chromosome).

As discussed above, the polymers of the invention are formulated with a delivery vehicle. For instance the following delivery vehicles have been described: cochleates; Emulsomes®; ISCOM®s; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex; nucleic acid vaccines; microspheres; polymers (e.g. carboxymethylcellulose, chitosan); polymer rings; proteosomes; sodium fluoride; transgenic plants. In some embodiments of the invention the delivery vehicle is a liposome, a niosome, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle, as a nanosphere or a nanocapsule, a polymeric microparticle, as a microsphere or a microcapsule.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. In some embodiments the composition is sterile.

The term "pharmaceutically-acceptable carrier" means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

For oral administration, the compounds (i.e., nucleic acids, antigens, antibodies, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art.

They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

TLR7 and TLR8 recognize single-stranded RNA or short oligoribonucleotides (ORN). Incubation of immune cells expressing one or both of the TLRs results in the induction of cytokine production. Due to the different expression patterns of the two receptors, TLR7-mediated signaling is thought to stimulate IFN-α production by human pDC whereas activation of TLR8 results in the activation of mainly mDCs and monocytes producing IL-12, TNF-α and IFN-γ. The existence of RNA motifs specifically inducing TLR8 and TLR7/8 activity has been demonstrated. The following Examples show the identification of an additional motif which is backbone-specific. A significant finding is that polymers containing this RNA motif induce mostly IFN-α arguing for a potent immunostimulatory motif that does not stimulate substantial levels of pro-inflammatory cytokines.

Methods:

ELISA Assays:

Human PBMC were incubated with serially diluted ORN in the presence of DOTAP (starting with 2 µM ORN and 25 µg/ml DOTAP) and supernatants were assayed by ELISA for IFN-α and IL-12p40 after 24 hours. Mean±SEM of 3 donors is shown.

Cytokine Detection:

Human PBMC were resuspended at a concentration of $5 \times 10^6$ cells/ml and added to 96-well round-bottomed plates (250l/well). PBMC were incubated with serially diluted ORN in the presence of DOTAP (starting with 2 µM ORN and 25 µg/ml DOTAP) and culture supernatants (SN) were collected 24 h later. If not used immediately, SN were stored at −20° C. until required.

Amounts of cytokines in the SN were assessed using a commercially available ELISA Kit for IL-12p40 (from BD Biosciences, Heidelberg, Germany), or an in-house ELISA for IFN-α developed using commercially available antibodies (PBL, New Brunswick, N.J., USA).

For analysis of a broad set of cytokines and chemokines, multiplex analysis with a luminex system from Bio-Rad (Munich, Germany) and Multiplex kits from Biosource (Solingen, Germany) was performed.

Example 1

Figure 1:
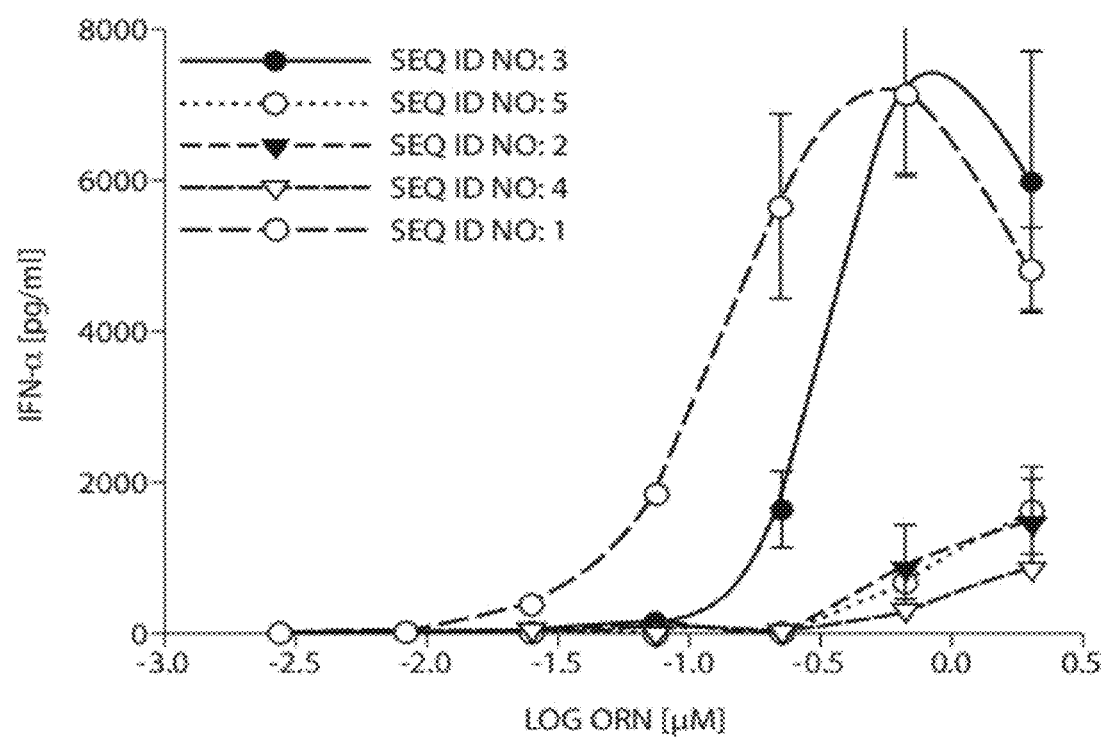
FIG. 1 is a graph showing induction of IFN-α production in human peripheral blood mononuclear cells (PBMC) after contacting the cell with oligoribonucleotides (ORN). ORN (starting concentration: 2 μM+50 μg/ml DOTAP (N-[1-(2,3-dioleoyloxy)propy-1]-N,N,N-trimethylammonium methylsulfate)) were incubated with human PBMC and supernatants were assayed 24 hours later for IFN-α by enzyme-linked immunosorbent assay (ELISA). Shown are a positive control (CCGUCUGUUGUGUGACUC; SEQ ID NO: 1) and four test sequences (SEQ ID NO:2-5, see Table 1). Mean±SEM of 3 donors is shown. The y-axis shows IFN-α concentration in pg/ml and the x-axis shows log ORN concentration in μM.

Identification of an Immune Stimulatory Polymer that Induces TLR7-but not TLR8-mediated Cytokines Four ORN and a positive control were tested for their ability to induce IFN-α (see Table 1 for sequences). ORN were incubated with human PBMC and supernatants were assayed for IFN-α by ELISA. ORNs SEQ ID NO:3 and SEQ ID NO:5 have the same base sequence, but SEQ ID NO:5 has a phosphorothioate (PS) backbone whereas ORN SEQ ID NO:3 has a phosphodiester (PO) backbone. Surprisingly, SEQ ID NO:5 induced only background levels of IFN-α whereas SEQ ID NO:3 induced maximal IFN-α levels comparable to the positive control ODN SEQ ID NO: 1, which has an optimized GU-rich motif within the phosphorothioate backbone (FIG. 1). These data suggested that for the ORN sequence of SEQ ID NO:3 and SEQ ID NO:5a PO backbone produced significant induction of IFN-α.

Two other ORN with a PO backbone, SEQ ID NO:2 and SEQ ID NO:4, were also tested for the ability to induce IFN-α and were shown to induce only very low levels of IFN-α. As shown by the comparison of the sequences of SEQ ID NO:2 and SEQ ID NO:3, presence of one uridine (U) dramatically enhanced induction of IFN-α. The uridine nucleotide was embedded in a certain sequence motif. The presence of one U not in this motif significantly reduced IFN-α production, as shown by the comparison of SEQ ID NO:3 and SEQ ID NO:4.

Figure 2A:
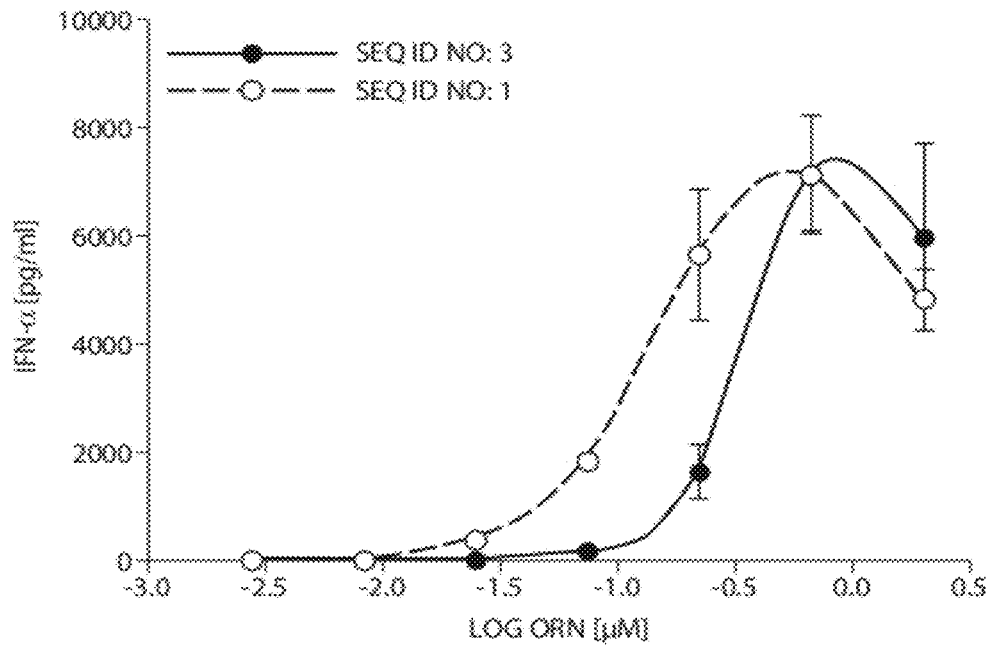
FIG. 2 is two graphs showing induction of IFN-α (FIG. 2A) and IL-12p40 (FIG. 2B) by ORN. Shown are an ORN known to induce both TLR 7/8-associated cytokines (SEQ ID NO: 1) and an ORN that induced more TLR7-associated cytokines (SEQ ID NO:3) than TLR8-associated cytokines. Human PBMC were incubated with ORN in the presence of DOTAP (2 μM ORN and 50 μg/ml DOTAP) and supernatants were assayed by ELISA 24 hours later for IFN-α and IL-12p40. Mean±SEM of 3 donors is shown. The y-axes are IFN-α (FIG. 2A) and IL-12p40 (FIG. 2B) concentration in pg/ml and the x-axis shows log ORN concentration in μM.
Figure 2B:
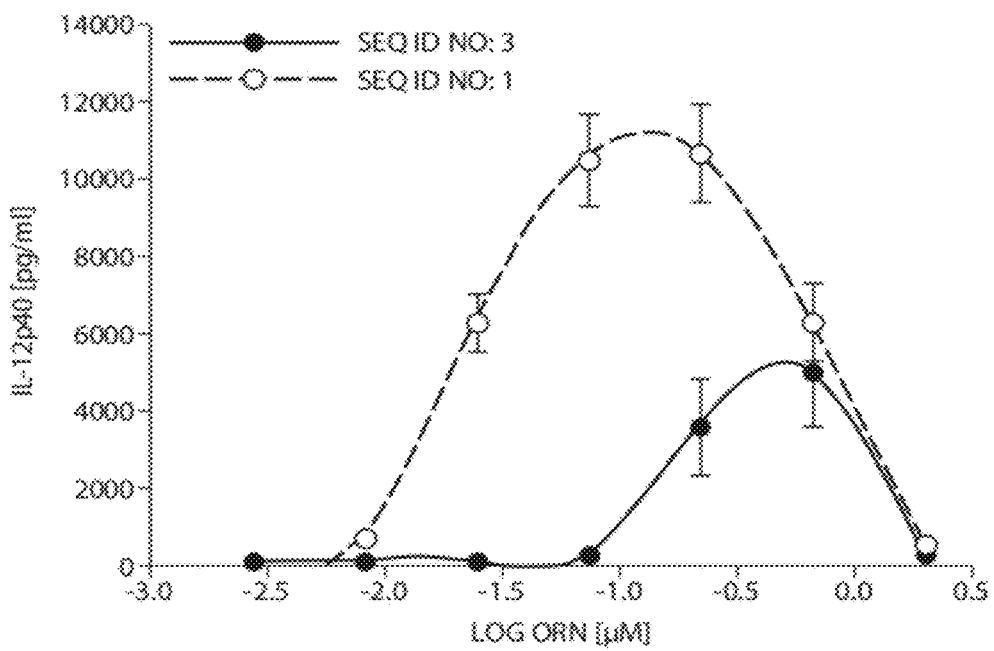

ORN SEQ ID NO:3 induced mainly IFN-α production (see also FIG. 2A), most likely TLR7-mediated, but induced very little other (TLR8-mediated) cytokines such as IL-12 (FIG. 2B), TNF-α (not shown) or IFN-γ (not shown).

Example 2

Identification of a New Immunostimulatory RNA Motif: CUCA

Figure 3:
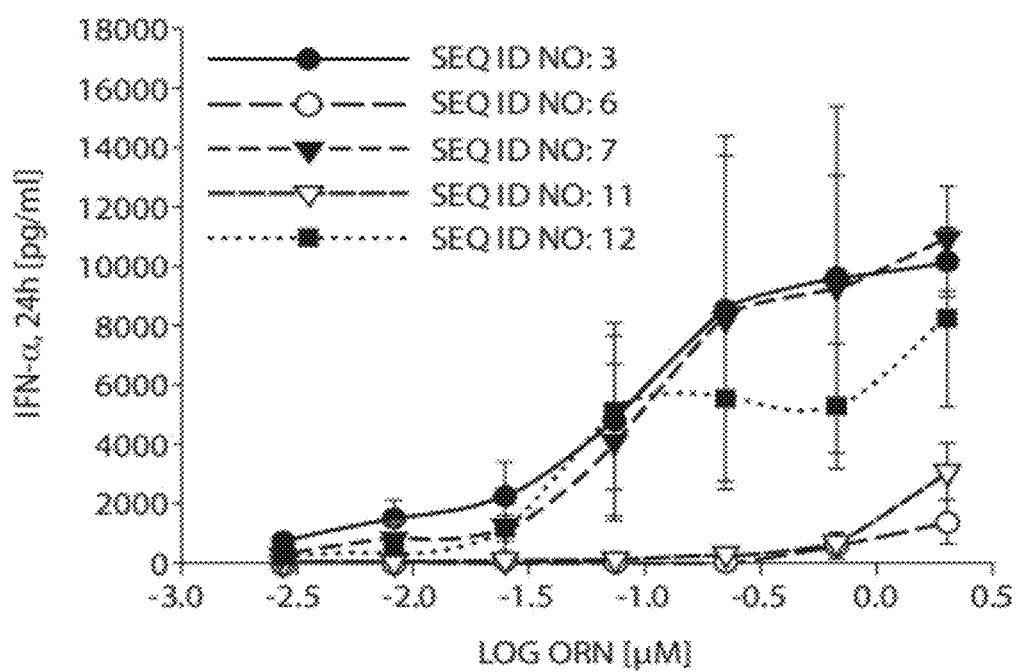
FIG. 3 is a graph showing induction of IFN-α production in human PBMC after contacting the cell with oligoribonucleotides (ORN). ORN (starting concentration: 2 μM+25 μg/ml DOTAP) were incubated with human PBMC and supernatants were assayed 24 hours later for IFN-α by ELISA. Shown are SEQ ID NO:3 and four ORN with slight sequence variations (SEQ ID NO:6, 7, 11, and 12, see Table 2). Mean±SEM of 3 donors is shown. The y-axis shows IFN-α concentration in pg/ml and the x-axis shows log ORN concentration in μM.

In order to determine the optimum backbone-specific immunostimulatory motif, ORN were designed and tested for the ability to induce IFN-α. In contrast to the previously identified RNA motifs, a new motif was defined that was unique and specific for ORN with phosphodiester backbones (FIG. 3). Human PBMC were incubated with ORN and supernatants were assayed by ELISA for IFN-α. A surprisingly short motif, UCA, was defined. The importance of the presence of an adenine base within this sequence was demonstrated. Comparison of SEQ ID NO:7 and SEQ ID NO:6 (see Table 2) demonstrated that the optimal motif included a base 3' to the UC. Comparison of SEQ ID NO: 11 and SEQ ID NO:12 confirmed the importance of the cytidine at the 3'-side of the uridine.

TABLE 2

| | |
|---|---|
| SEQ ID NO: 3 | rA-rA-rA-rC-rG-rC-rU-rC-rA-rG-rC-rC-rA-rA-rA-rG-rC-rA-rG |
| SEQ ID NO: 6 | rA-rA-rA-rC-rG-rC-rA-rC-rA-rG-rC-rC-rA-rA-rA-rG-rC-rU-rC |
| SEQ ID NO: 7 | rA-rC-rG-rC-rA-rC-rA-rG-rC-rC-rA-rA-rA-rG-rC-rU-rC-rA-rG |
| SEQ ID NO: 11 | rG-rC-rC-rA-rC-rC-rG-rA-rG-rC-rU-rG-rA-rA-rG-rG-rC-rA-rC-rC |
| SEQ ID NO: 12 | rG-rC-rC-rA-rC-rC-rG-rA-rG-rC-rU-rC-rA-rA-rG-rG-rC-rA-rC-rC |

Exchanging the central C of the proposed minimal motif resulted in a loss of IFN-α-inducing activity in the case of UGA (SEQ ID NO:8) and UAA (SEQ ID NO:9) and in a reduction of IFN-α response in the case of UUA (SEQ ID NO:10) (see FIG. 4) in the context of these ORN. The low IFN-α induction of SEQ ID NO:10 was most likely due to the presence of the motif GCUU containing two U.

These ORN also demonstrated that the newly defined minimal motif was very specific for the induction of an IFN-α biased immune response as all 3 PO ORN without the C in the motif (SEQ ID NO:8, SEQ ID NO:9, SEQ ID NO:10) induced much higher levels of IL-12 than the parent ORN SEQ ID NO:3 containing the UCA motif (see Table 3).

TABLE 1

| | |
|---|---|
| SEQ ID NO: 1 | rC*rC*rG*rU*rC*rU*rG*rU*rU*rG*rU*rG*rU*rG*rA*rC*rU*rC |
| SEQ ID NO: 2 | rA-rA-rA-rC-rG-rC-rA-rC-rA-rG-rC-rC-rA-rA-rA-rG-rC-rA-rG |
| SEQ ID NO: 3 | rA-rA-rA-rC-rG-rC-rU-rC-rA-rG-rC-rC-rA-rA-rA-rG-rC-rA-rG |
| SEQ ID NO: 4 | rA-rA-rA-rA-rA-rA-rA-rU-rA-rA-rA-rA-rA-rA-rA-rA |
| SEQ ID NO: 5 | rA*rA*rA*rC*rG*rC*rU*rC*rA*rG*rC*rC*rA*rA*rA*rG*rC*rA*rG |

ORN Backbones: "-" depicts phosphodiester, "*" depicts phosphorothioate.

TABLE 3

| SEQ ID NO: 3 | rA-rA-rA-rC-rG-rC-rU-rC-rA-rG-rC-rC-rA-rA-rA-rG-rC-rA-rG |
| --- | --- |
| SEQ ID NO: 8 | rA-rA-rA-rC-rG-rC-rU-rG-rA-rG-rC-rC-rA-rA-rA-rG-rC-rA-rG |
| SEQ ID NO: 9 | rA-rA-rA-rC-rG-rC-rU-rA-rA-rG-rC-rC-rA-rA-rA-rG-rC-rA-rG |
| SEQ ID NO: 10 | rA-rA-rA-rC-rG-rC-rU-rU-rA-rG-rC-rC-rA-rA-rA-rG-rC-rA-rG |

Figure 5A:
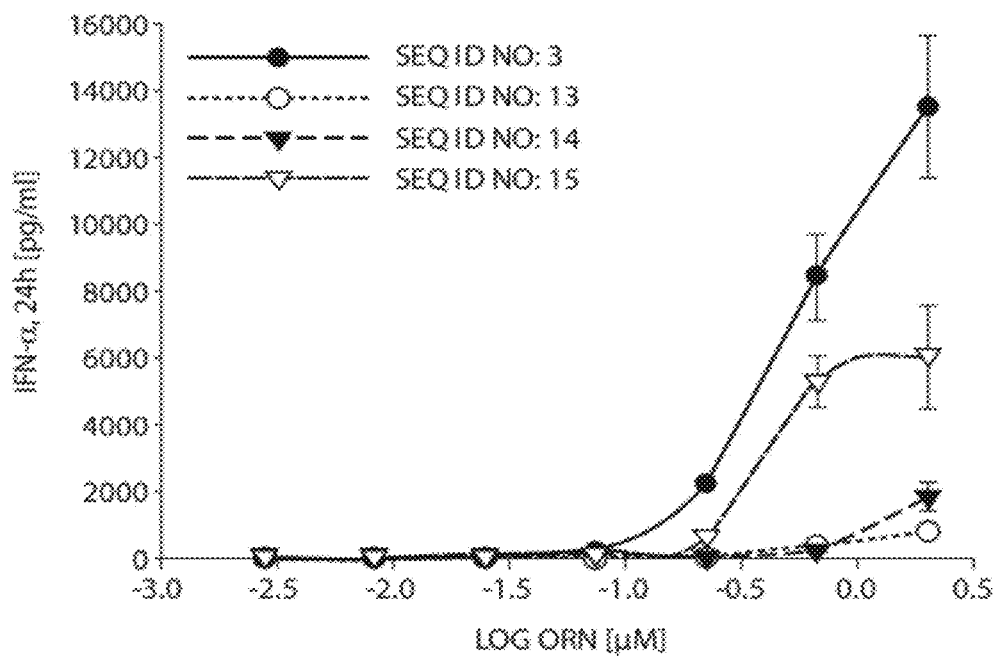
FIG. 5 is two graphs showing induction of IFN-α (FIG. 5A) and IL-12p40 (FIG. 5B) by ORN. Shown are SEQ ID NO:3 and three other ORN with slight sequence variations (SEQ ID NO:13-15, see Table 4). Human PBMC were incubated with ORN in the presence of DOTAP (2 μM ORN and 25 μg/ml DOTAP) and supernatants were assayed for IFN-α and IL-12p40 24 hours later by ELISA. Mean±SEM of 3 donors is shown. The y-axes are IFN-α (FIG. 5A) and IL-12p40 (FIG. 5B) concentration in pg/ml and the x-axis shows log ORN concentration in μM.
Figure 5B:
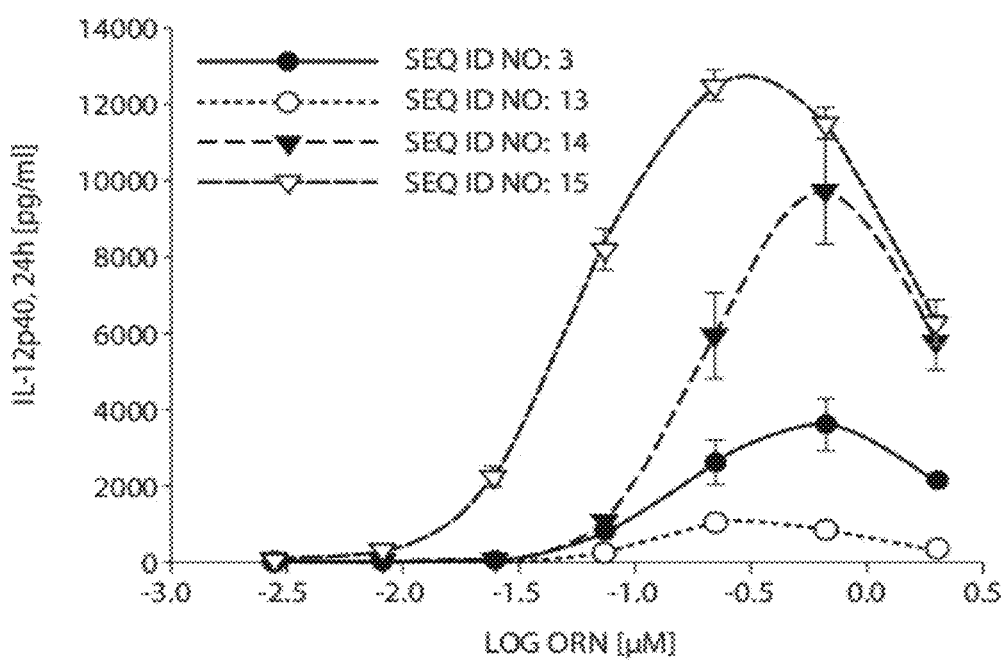

Further testing of sequence variations resulted in data demonstrating that the adenosine moiety of the UCA motif is important for the IFN-α activity (FIG. 5, sequences in Table 4). Human PBMC were incubated with ORN and supernatants were assayed by ELISA for IFN-α and IL-12p40. Replacement of the adenosine within the UCA motif with either C or G (SEQ ID NO:13, SEQ ID NO:14) yielded ORN which induced only background levels of IFN-α. SEQ ID NO:15 (UCU) induced moderate amounts of IFN-α but less than SEQ ID NO:3. The induction was most likely due to the generation of an additional sequence UCUG. Again, induction of IL-12 by SEQ ID NO:3 was very low compared to ORN SEQ ID NO:14 and SEQ ID NO:15.

observed only when a uridine was not present at this position, as the UUCA motif led to both high IFN-α and high IL-12 production.

TABLE 4

| SEQ ID NO: 3 | rA-rA-rA-rC-rG-rC-rU-rC-rA-rG-rC-rC-rA-rA-rA-rG-rC-rA-rG |
| --- | --- |
| SEQ ID NO: 13 | rA-rA-rA-rC-rG-rC-rU-rC-rC-rG-rC-rC-rA-rA-rA-rG-rC-rA-rG |
| SEQ ID NO: 14 | rA-rA-rA-rC-rG-rC-rU-rC-rG-rG-rC-rC-rA-rA-rA-rG-rC-rA-rG |
| SEQ ID NO: 15 | rA-rA-rA-rC-rG-rC-rU-rC-rU-rG-rC-rC-rA-rA-rA-rG-rC-rA-rG |

To further evaluate the need for additional nucleotides surrounding the minimal motif, nucleotide modifications 3' and 5' the UCA motif were tested for their IFN-α versus IL-12 inducing activities (sequences shown in Table 5). As shown in

TABLE 5

| SEQ ID NO: 3 | rA-rA-rA-rC-rG-rC-rU-rC-rA-rG-rC-rC-rA-rA-rA-rG-rC-rA-rG |
| --- | --- |
| SEQ ID NO: 19 | rA-rA-rA-rC-rG-rG-rU-rC-rA-rG-rC-rC-rA-rA-rA-rG-rC-rA-rG |
| SEQ ID NO: 20 | rA-rA-rA-rC-rG-rA-rU-rC-rA-rG-rC-rC-rA-rA-rA-rG-rC-rA-rG |
| SEQ ID NO: 21 | rA-rA-rA-rC-rG-rU-rU-rC-rA-rG-rC-rC-rA-rA-rA-rG-rC-rA-rG |

Figure 6A:
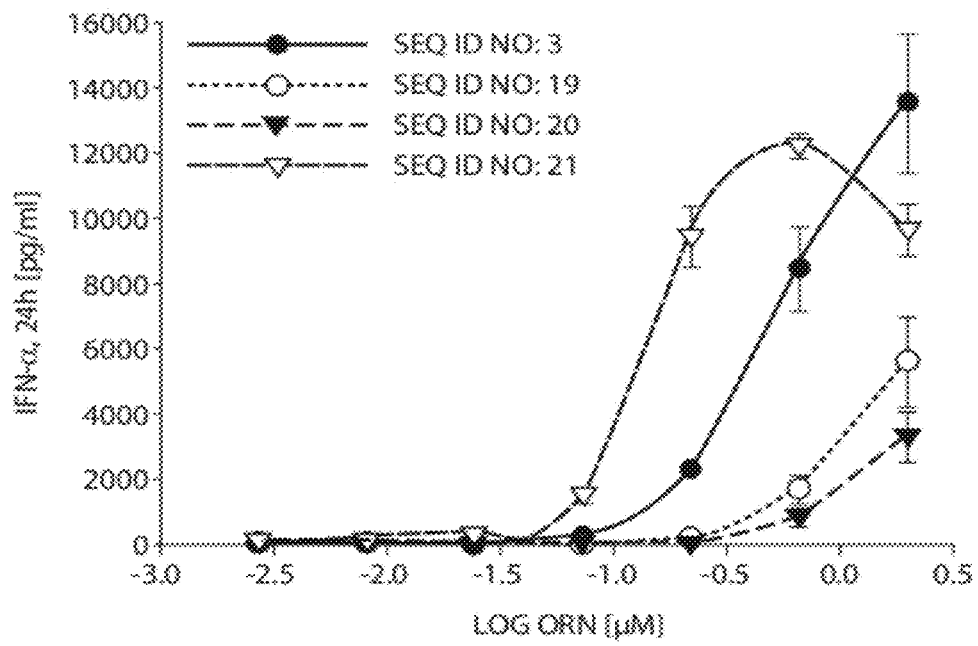
FIG. 6 is two graphs showing induction of IFN-α (FIG. 6A) and IL-12p40 (FIG. 6B) by ORN. Shown are SEQ ID NO:3 and three other ORN with slight sequence variations (SEQ ID NO:19-21, see Table 5). Human PBMC were incubated with ORN in the presence of DOTAP (2 μM ORN and 25 μg/ml DOTAP) and supernatants were assayed for IFN-α and IL-12p40 24 hours later by ELISA. Mean±SEM of 3 donors is shown. The y-axes are IFN-α (FIG. 6A) and IL-12p40 (FIG. 6B) concentration in pg/ml and the x-axis shows log ORN concentration in μM.
Figure 6B:
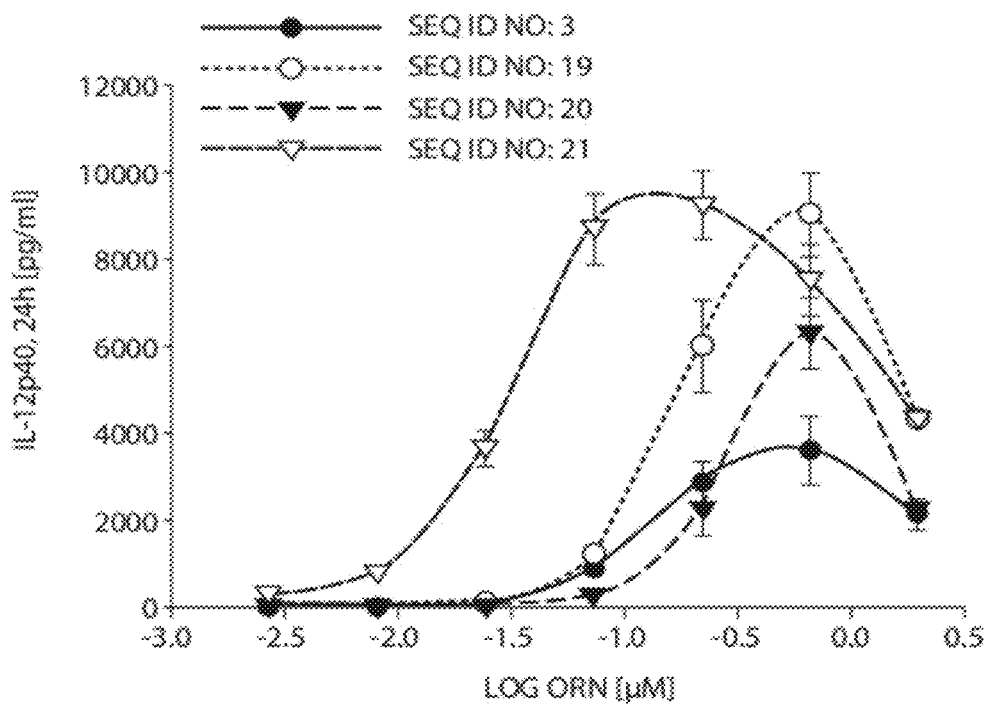
Figure 7A:
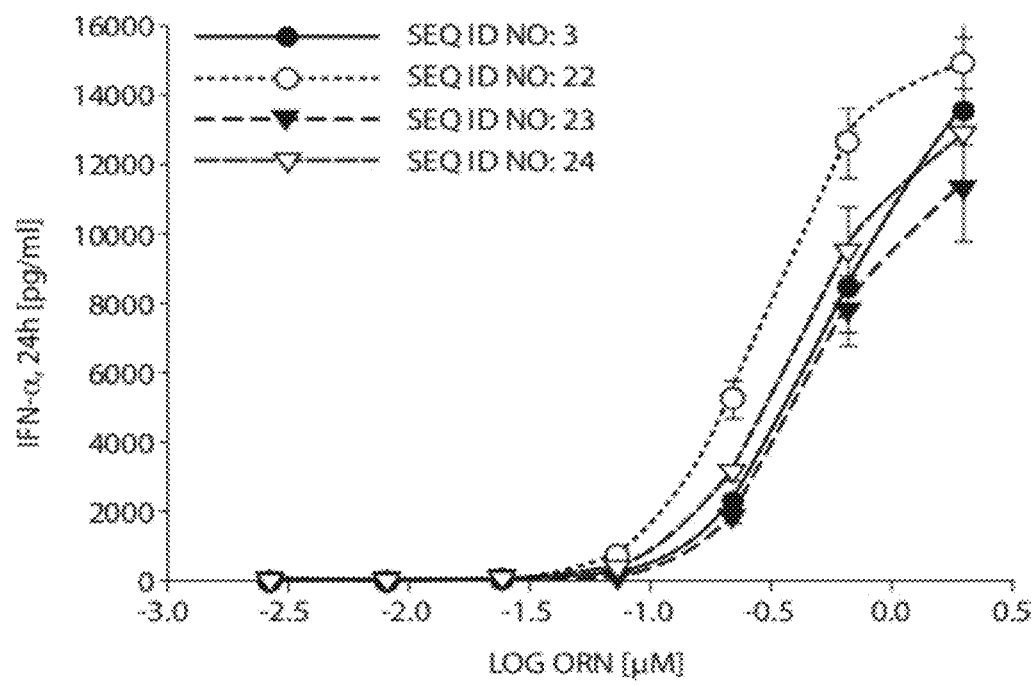
FIG. 7 is four graphs showing induction of IFN-α (FIGS. 7A and 7C) and IL-12p40 (FIGS. 7B and 7D) by ORN. Shown are SEQ ID NO:3 and six other ORN with slight sequence variations (SEQ ID NO:16-18 and 22-24, see Table 3). Human PBMC were incubated with ORN in the presence of DOTAP (2 μM ORN and 25 μg/ml DOTAP) and supernatants were assayed for IFN-α and IL-12p40 24 hours later by ELISA. Mean±SEM of 3 donors is shown. The y-axes are IFN-α (FIGS. 7A and 7B) and IL-12p40 (FIGS. 7C and 7C) concentration in pg/ml and the x-axis shows log ORN concentration in μM.
Figure 7B:
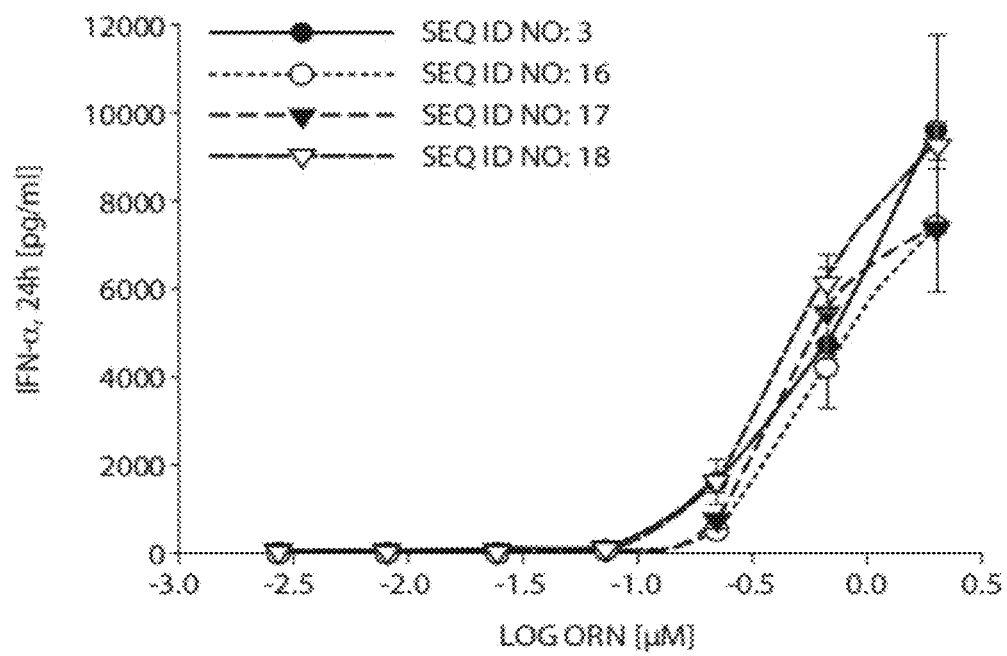
Figure 7C:
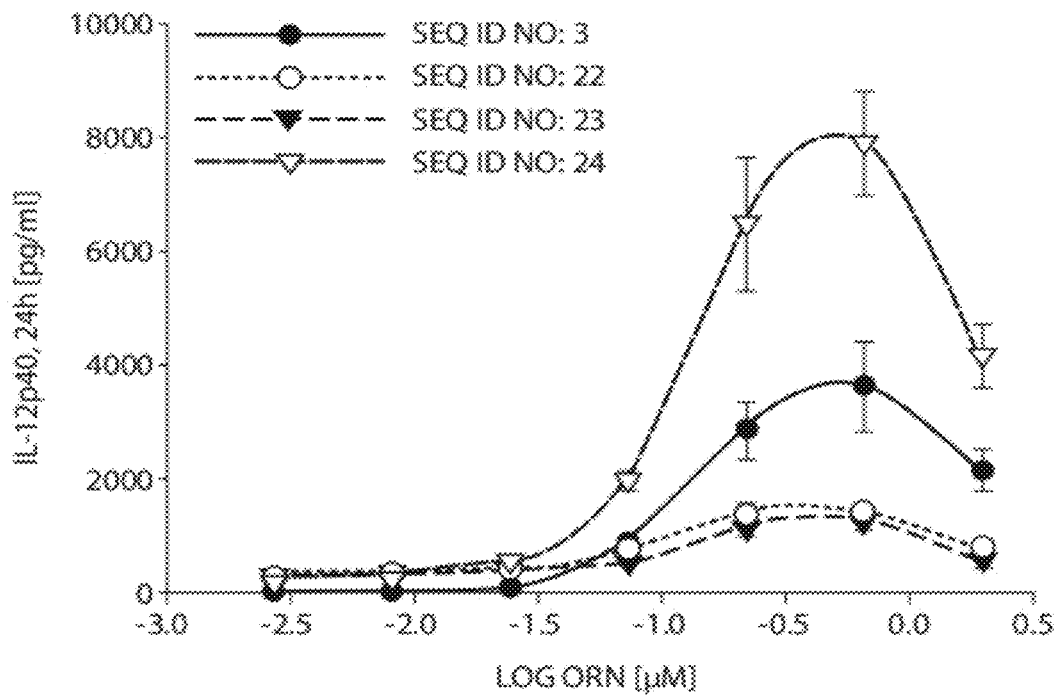
Figure 7D:
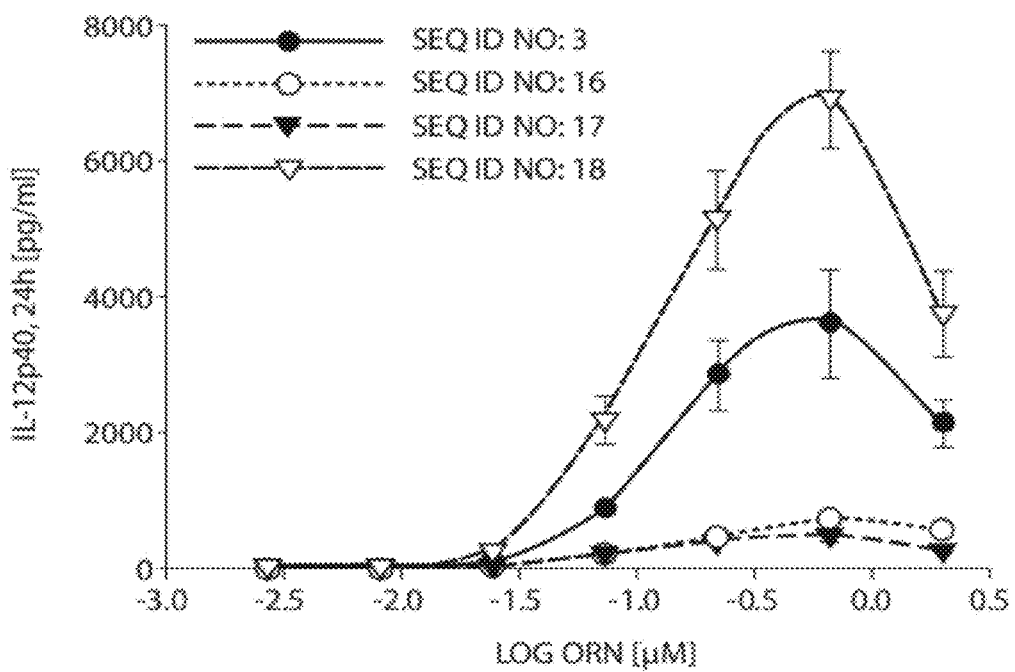
Figure 8A:
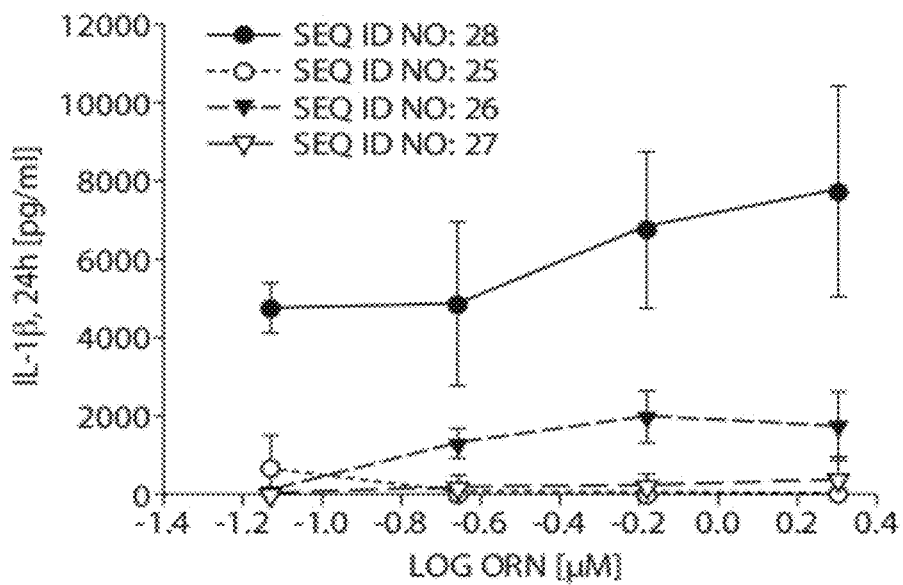
FIG. 8 is four graphs comparing in vitro cytokine induction by an ORN with the immunostimulatory UCA motif (GACACACACACUCACACACACACA; SEQ ID NO:27). SEQ ID NO:27 induces no substantial IL-12 (FIG. 8A), IL-6 (FIG. 8B), IL-2R (FIG. 8C), or IL-7 (FIG. 8D). Results are compared to a negative control (GACACACACACACACACA-CACACA; SEQ ID NO:25), a non-UCA ORN with a U-rich 3' end (GACACACACACACACACACACUUU; SEQ ID NO:26), and a positive control (UUGUUGUUGUUGUUG-UUGUU (all phosphorothioate); SEQ ID NO:28). Human PBMC of three healthy blood donors were incubated for 24 hours with up to 2 μM ORN in the presence of DOTAP. Supernatants were collected and cytokine or chemokine concentration measured by ELISA. The y-axes are cytokine or chemokine concentration in pg/ml and the x-axes show log ORN concentration in μM.
Figure 8B:
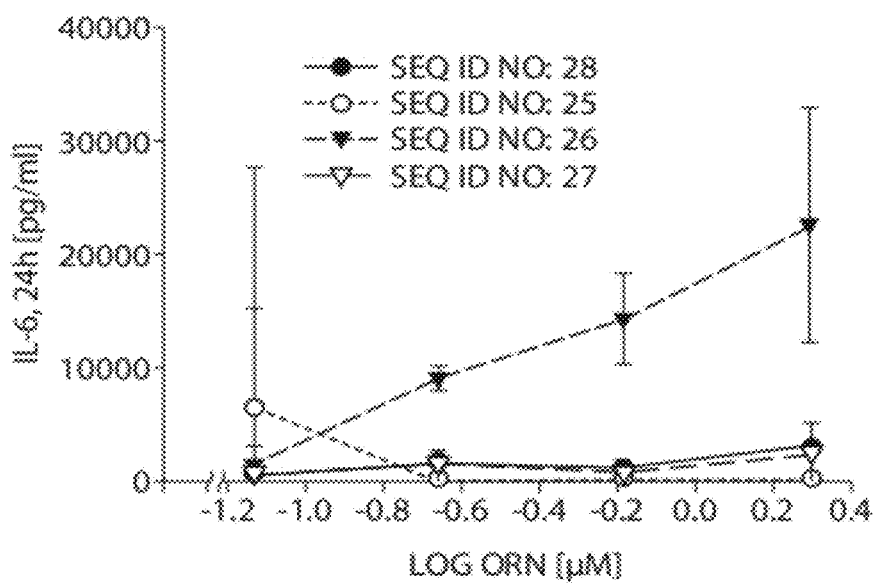
Figure 8C:
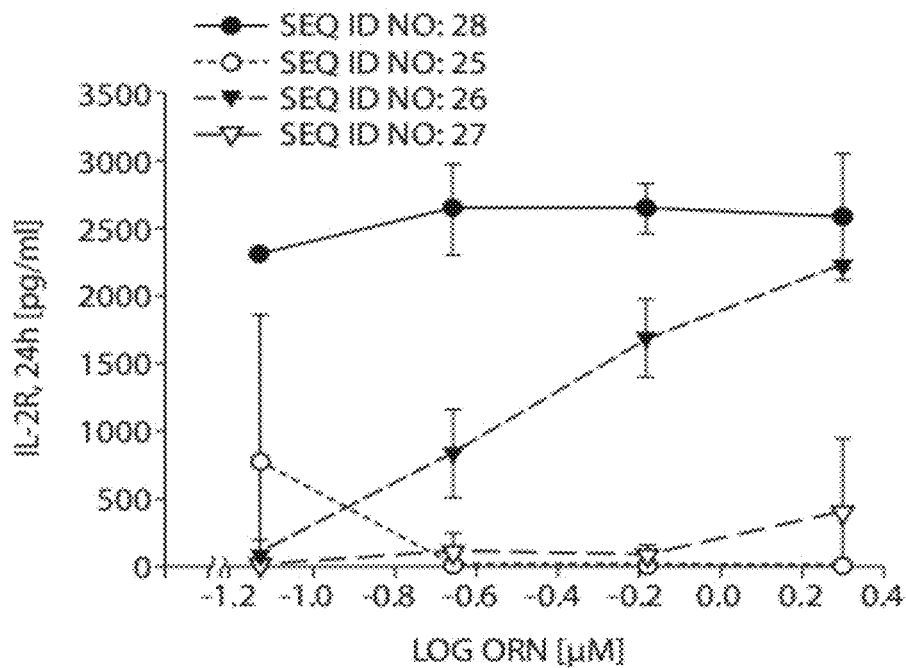
Figure 8D:
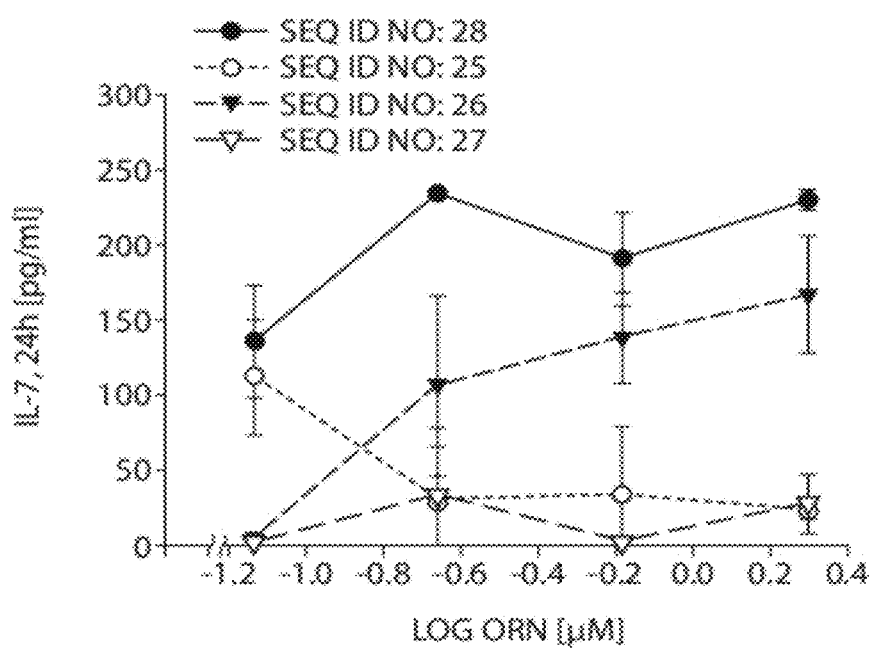
Figure 9A:
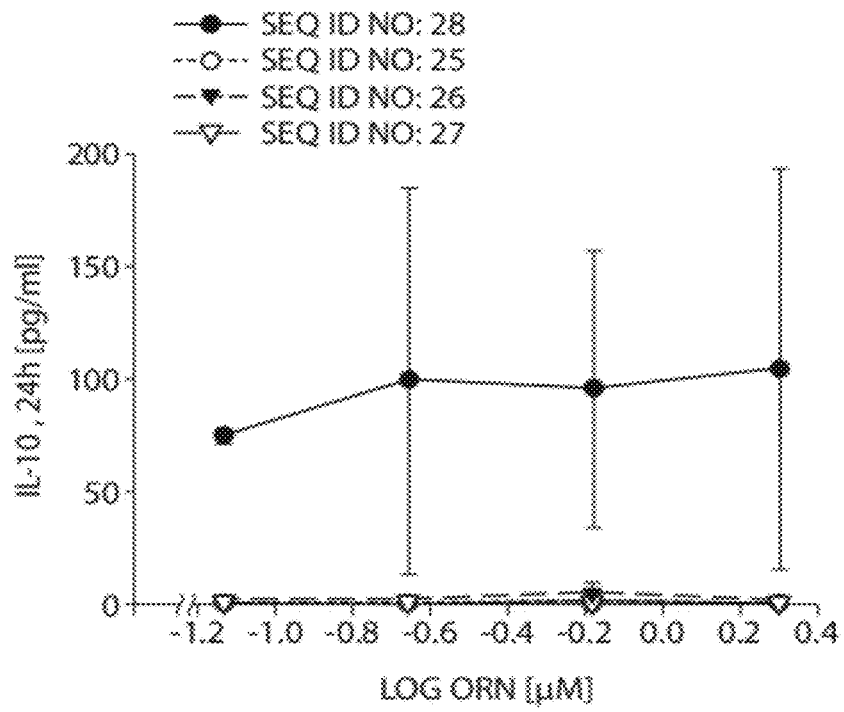
FIG. 9 is four graphs comparing in vitro cytokine induction by an ORN with the immunostimulatory UCA motif (SEQ ID NO:27). SEQ ID NO:27 induces no substantial IL-10 (FIG. 9A), IL-15 (FIG. 9B), IL-12p40 (FIG. 9C), or TNF-α (FIG. 9D). Results are compared to a negative control (SEQ ID NO:25), a non-UCA ORN with a U-rich 3' end (SEQ ID NO:26) and a positive control (SEQ ID NO:28). Human PBMC of three healthy blood donors were incubated for 24 hours with up to 2 μM ORN in the presence of DOTAP. Supernatants were collected and cytokine or chemokine concentration measured by ELISA. The y-axes are cytokine or chemokine concentration in pg/ml and the x-axes show log ORN concentration in μM.
Figure 9B:
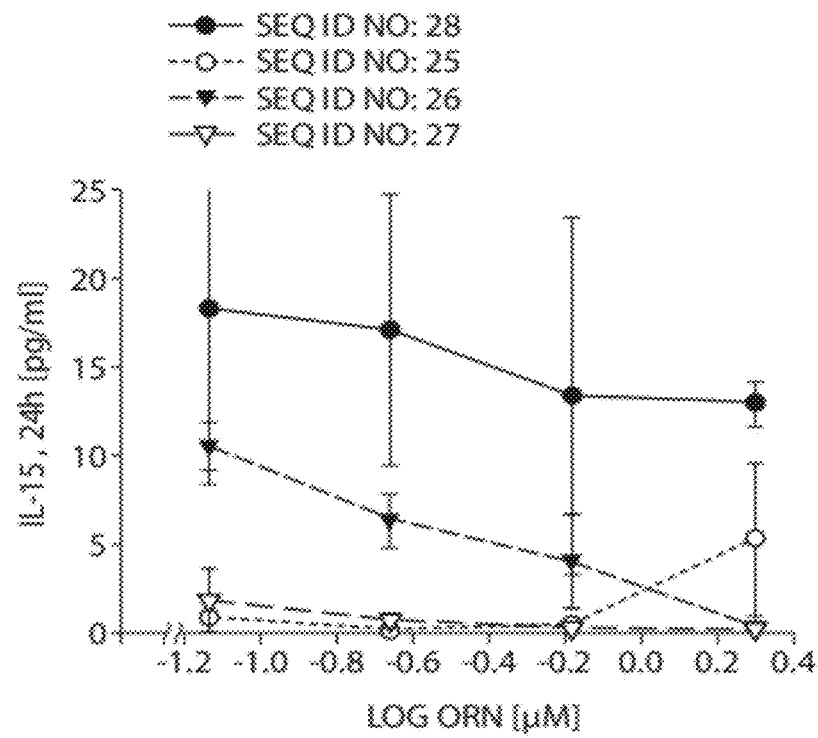
Figure 9C:
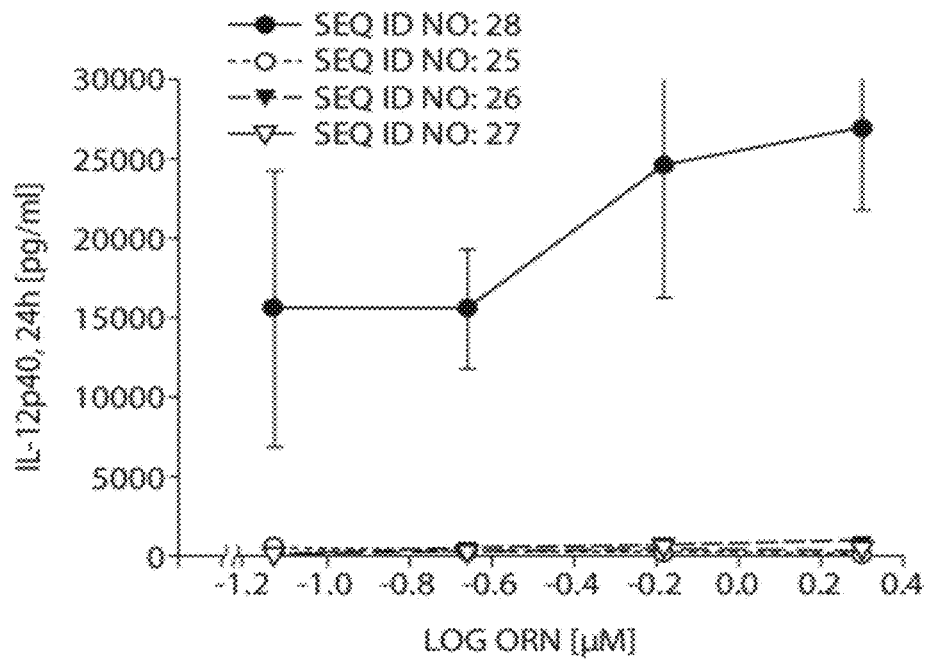
Figure 9D:
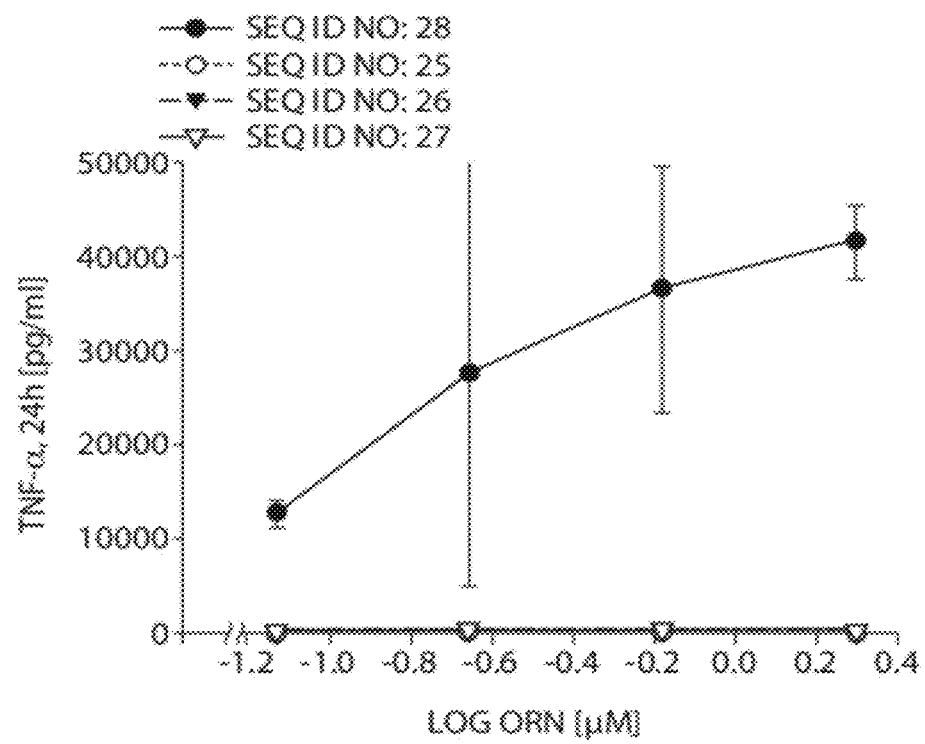
Figure 10A:
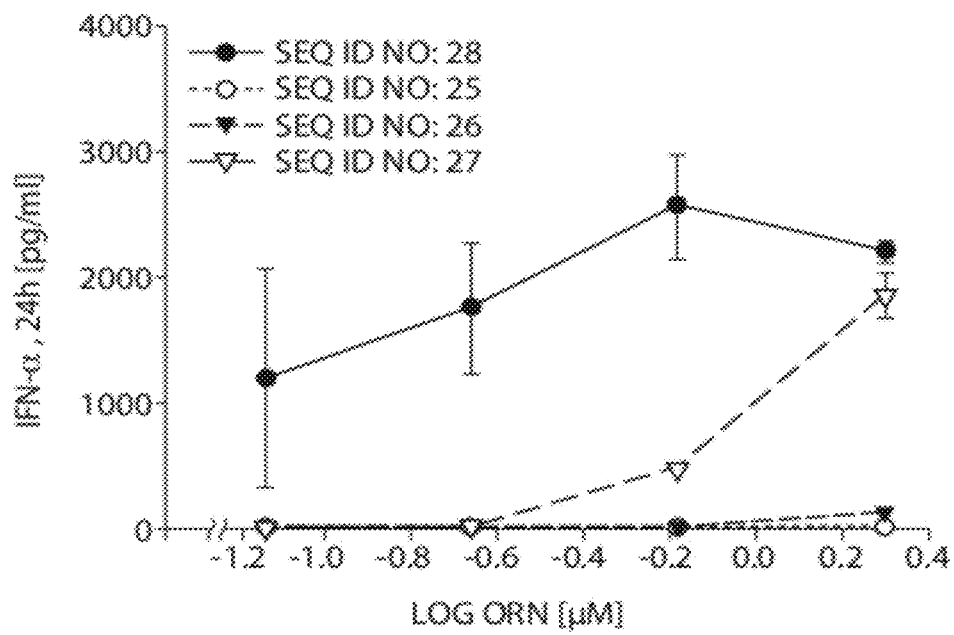
FIG. 10 is four graphs comparing in vitro cytokine induction by an ORN with the immunostimulatory UCA motif (SEQ ID NO:27). SEQ ID NO:27 induces no substantial MIP-1α (FIG. 10B), IFN-γ (FIG. 10C), or MIP-1β (FIG. 10D), but does induce IFN-α (FIG. 10A). Results are compared to a negative control (SEQ ID NO:25), a non-UCA ORN with a U-rich 3' end (SEQ ID NO:26) and a positive control (SEQ ID NO:28). Human PBMC of three healthy blood donors were incubated for 24 hours with up to 2 μM ORN in the presence of DOTAP. Supernatants were collected and cytokine or chemokine concentration measured by ELISA. The y-axes are cytokine or chemokine concentration in pg/ml and the x-axes show log ORN concentration in μM.
Figure 10B:
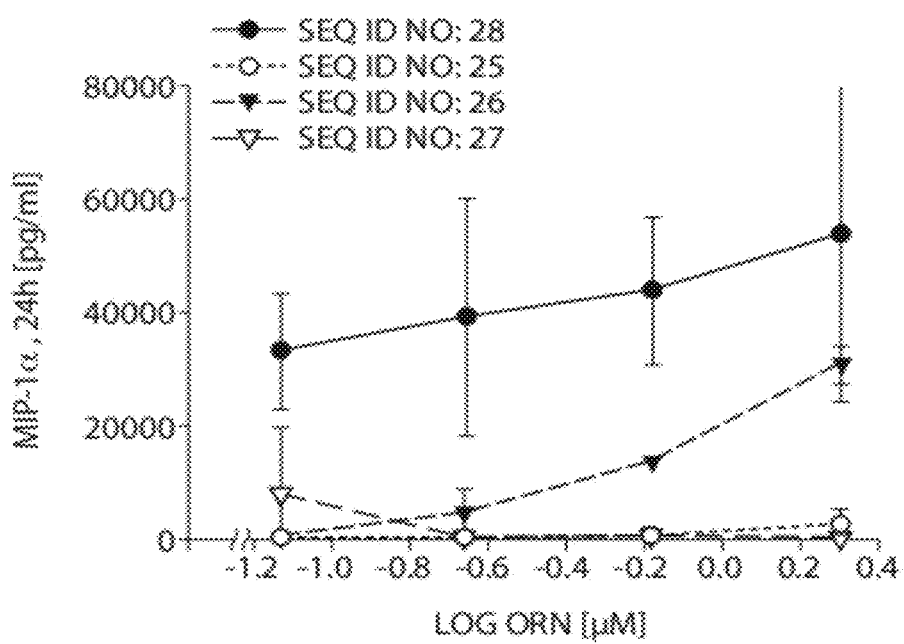
Figure 10C:
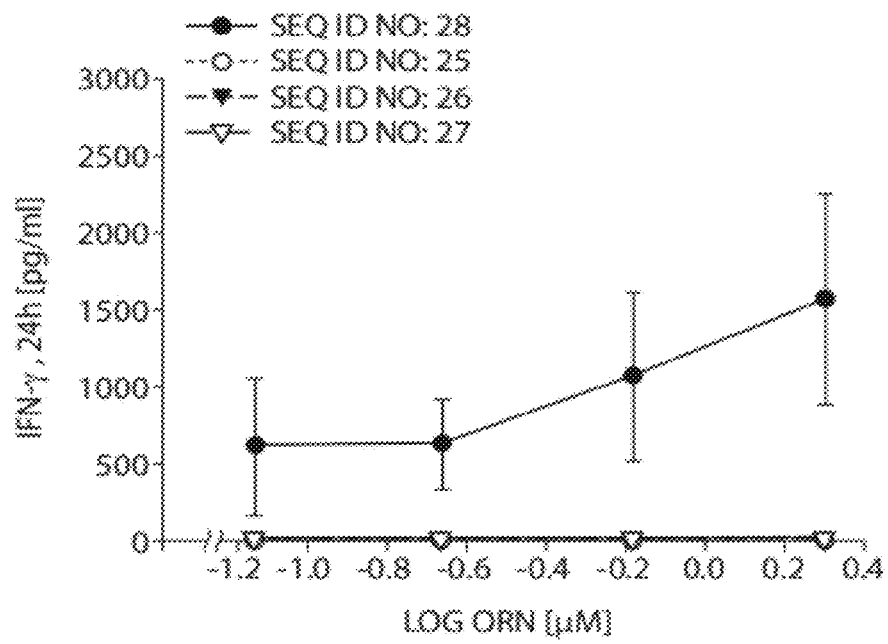
Figure 10D:
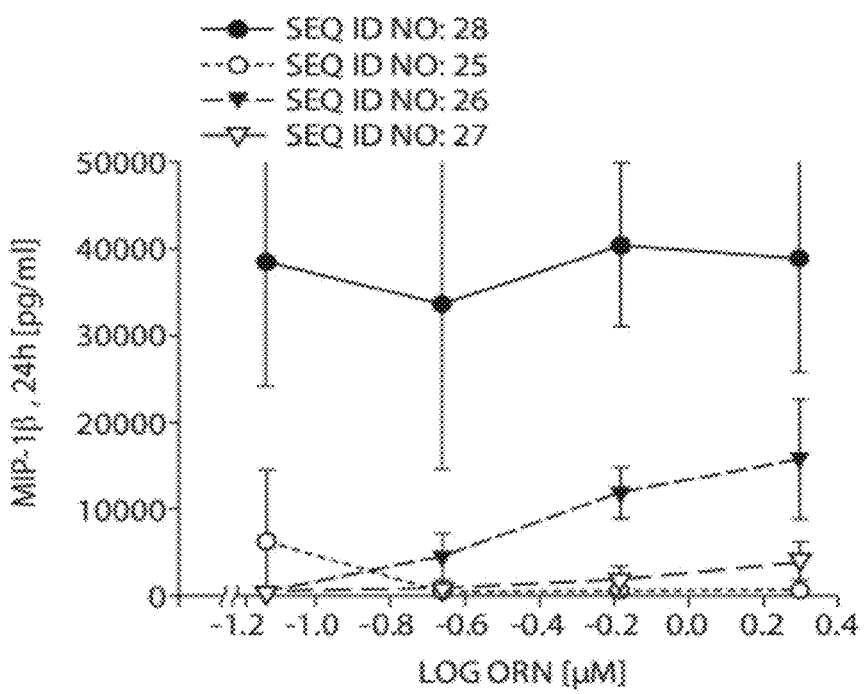
Figure 11A:
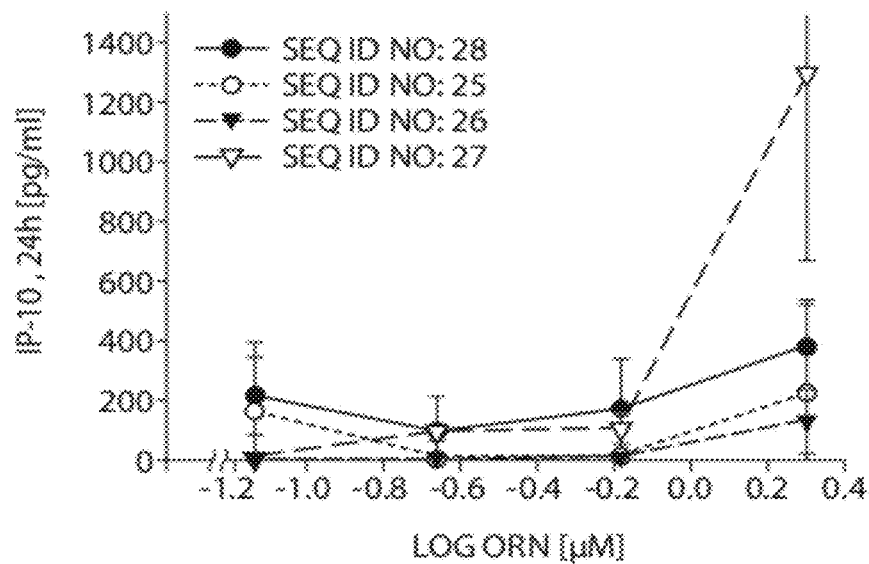
FIG. 11 is three graphs comparing in vitro cytokine induction by an ORN with the immunostimulatory UCA motif (SEQ ID NO:27). SEQ ID NO:27 induces no substantial MIG (FIG. 11C) but does induce IP-10 (FIG. 11A) and MCP-1
(FIG. 11B). Results are compared to a negative control (SEQ ID NO:25), a non-UCA ORN with a U-rich 3' end (SEQ ID NO:26) and a positive control (SEQ ID NO:28). Human PBMC of three healthy blood donors were incubated for 24 hours with up to 2 µM ORN in the presence of DOTAP. Supernatants were collected and cytokine or chemokine concentration measured by ELISA. The y-axes are cytokine or chemokine concentration in pg/ml and the x-axes show log ORN concentration in µM.
Figure 11B:
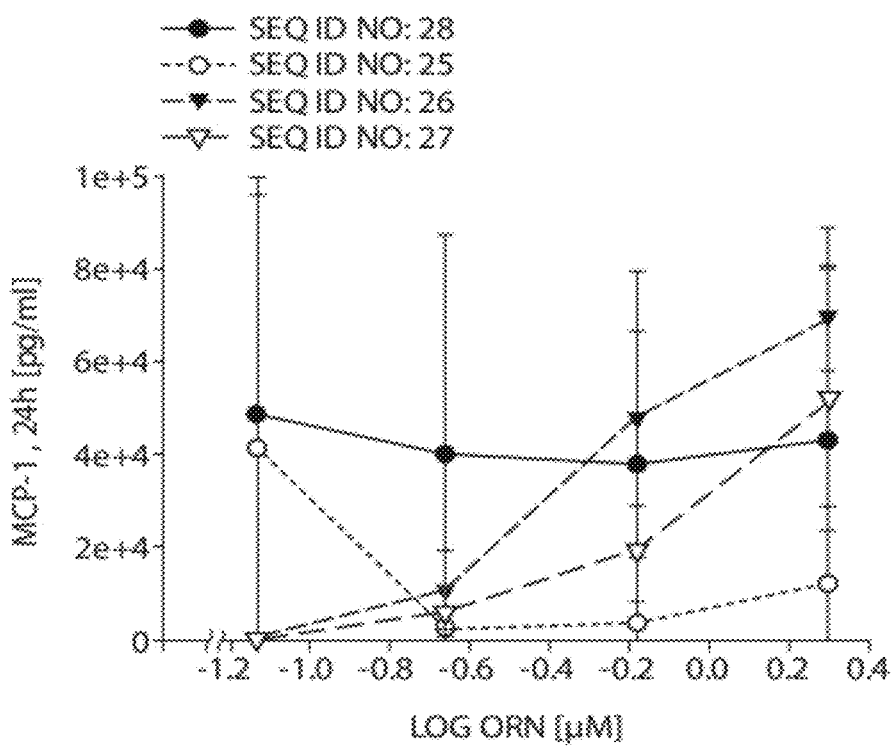
Figure 11C:
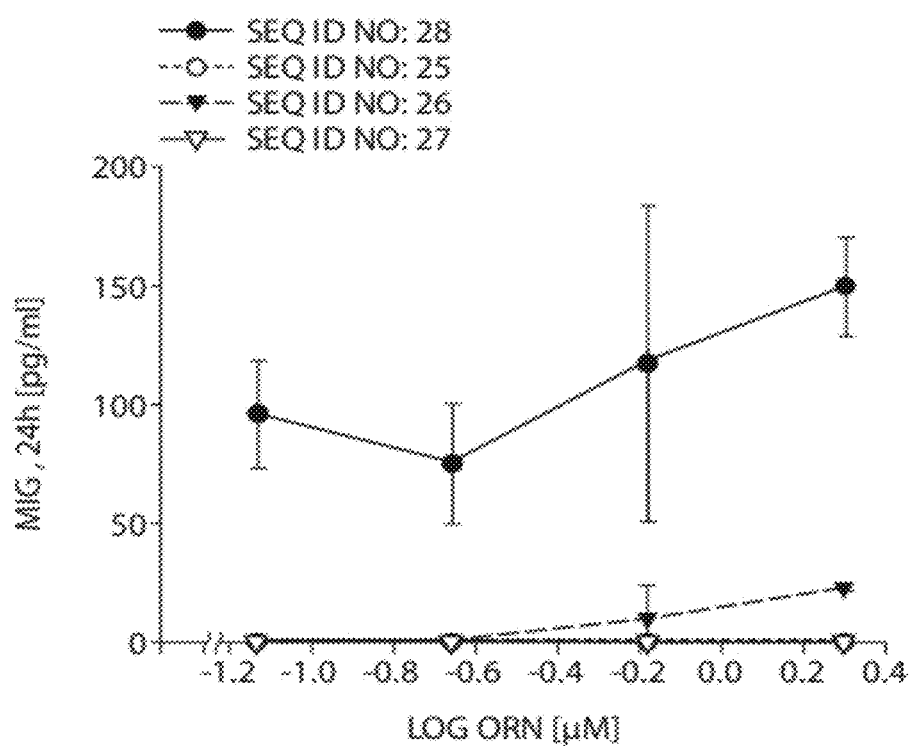

FIG. 6, in the region 5' of the minimal motif UCA only the presence of a cytidine (CUCA, SEQ ID NO:3) or uridine nucleotide (UUCA, SEQ ID NO:21) resulted in ORN with high IFN-α induction properties. However, the described unexpected activity of the ORN to induce a high amount of IFN-α without inducing a high amount of IL-12p40 was Further sequence analysis showed that the nucleotide positions next to the 4-mer motif CUCA did not appear to be as critical and did not influence the ability of the ORN to induce IFN-α production (Table 6). These nucleotides did influence IL-12 production, however, as shown in FIG. 7. Neither the nucleotide on the 5'-side (FIG. 7A, SEQ ID NO:22, 23, and 24) of the CUCA motif nor on the 3'-side (FIG. 7B, SEQ ID NO:16, 17, and 18) seemed to influence IFN-α-inducing activity. These nucleotides appeared to influence only IL-12 induction. Therefore, for an optimal TLR7-specific induction profile, these positions should be preferably not a uridine as in SEQ ID NO:24 and SEQ ID NO: 18, as these ORN showed relatively strong IL-12-inducing capacities (FIG. 7 C and FIG. 7 D).

TABLE 6

| SEQ ID NO: 3 | rA-rA-rA-rC-rG-rC-rU-rC-rA-rG-rC-rC-rA-rA-rA-rG-rC-rA-rG |
| SEQ ID NO: 16 | rA-rA-rA-rC-rG-rC-rU-rC-rA-rA-rC-rC-rA-rA-rA-rG-rC-rA-rG |
| SEQ ID NO: 17 | rA-rA-rA-rC-rG-rC-rU-rC-rA-rC-rC-rC-rA-rA-rA-rG-rC-rA-rG |
| SEQ ID NO: 18 | rA-rA-rA-rC-rG-rC-rU-rC-rA-rU-rC-rC-rA-rA-rA-rG-rC-rA-rG |
| SEQ ID NO: 22 | rA-rA-rA-rC-rA-rC-rU-rC-rA-rG-rC-rC-rA-rA-rA-rG-rC-rA-rG |
| SEQ ID NO: 23 | rA-rA-rA-rC-rC-rC-rU-rC-rA-rG-rC-rC-rA-rA-rA-rG-rC-rA-rG |
| SEQ ID NO: 24 | rA-rA-rA-rC-rU-rC-rU-rC-rA-rG-rC-rC-rA-rA-rA-rG-rC-rA-rG |

Example 3

Cytokine Profile of CUCA-motif ORN

The immunostimulatory CUCA motif ORN SEQ ID NO:27 (GACACACACACUCACACACACACA) was tested for its ability to induce a wide variety of cytokines. The cytokine induction of ORN SEQ ID NO:27 was compared a negative control (GACACACACACACACACACACACA; SEQ ID NO:25), a non-UCA ORN with a U-rich 3' end (GACACACACACACACACACACUUU; SEQ ID NO:26), and a positive control (GACACACACACUCACACACACA-CACA; SEQ ID NO:28). Human PBMC of three healthy blood donors were incubated for 24 h with serially diluted ORN in the presence of DOTAP (starting with 2 μM ORN and 25 μg/ml DOTAP). SN were collected and a cytokine or chemokine concentration of a variety of cytokines and chemokines was measured by ELISA. The results are shown in FIGS. 8-11. SEQ ID NO:27 induced IFN-α, and to a lesser extent the IFN-α-related molecules IP-10 and MCP-1.

For analysis of a larger set of cytokines and chemokines, multiplex analysis with a Luminex system Multiplex kits was performed. Two donors were used in this initial non-quantitative assessment of Luminex data. Results are summarized in Table 7 below. Again, SEQ ID NO:27 induced only IFN-α and IP-10 and to a lesser extent MIP-1

TABLE 7

| | SEQ ID NO: 25 | SEQ ID NO: 26 | SEQ ID NO: 28 | SEQ ID NO: 27 | DOTAP |
|---|---|---|---|---|---|
| IL-1B | − | + | +++ | − | − |
| IL-1Ra | − | − | − | − | − |
| IL-2 | − | − | − | − | − |
| IL-2R | − | + | +++ | − | − |
| IL-4 | n.d. | n.d. | n.d. | n.d. | n.d. |
| IL-5 | − | − | − | | |
| IL-6 | − | + | +++ | − | − |
| IL-7 | − | ++ | +++ | − | + |
| IL-8 | − | + | + | − | + |
| IL-10 | − | − | +++ | − | − |
| IL-12p40 | − | − | +++ | − | − |
| IL-13 | n.d. | n.d. | n.d. | n.d. | n.d. |
| IL-15 | − | + | +++ | − | − |
| IL-17 | n.d. | n.d. | n.d. | n.d. | n.d. |
| TNF-α | − | − | +++ | − | − |
| IFN-α | − | − | +++ | ++ | − |
| IFN-γ | − | − | +++ | − | − |
| GMCSF | n.d. | n.d. | n.d. | n.d. | n.d. |
| MIP-1a | − | + | +++ | − | − |
| MIP-1b | − | + | +++ | − | − |
| IP-10 | − | − | + | ++ | + |
| MIG | − | + | +++ | − | − |
| Eotaxin | n.d. | n.d. | n.d. | n.d. | n.d. |
| Rantes | − | − | + | − | + |
| MCP-1 | − | + | ++ | + | + | n.d. = not detected

Example 4

Substantial Induction of Th1 Cytokines and Chemokines by ORN with UCA Motif

Figure 12A:
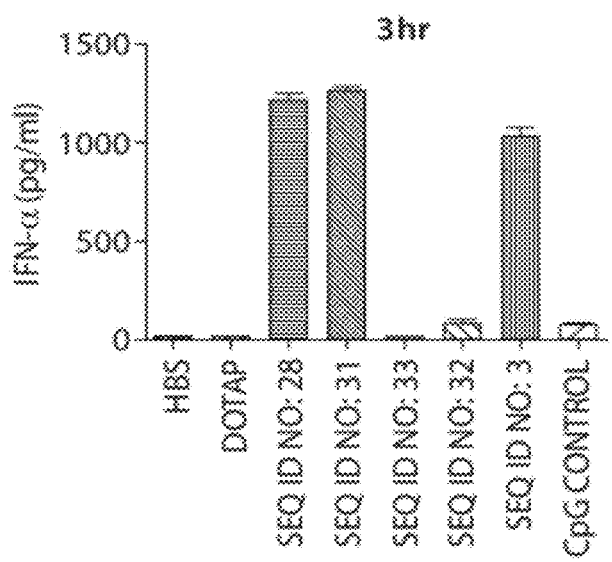
FIG. 12 is four graphs comparing in vivo cytokine induction by an ORN with the immunostimulatory UCA motif (SEQ ID NO:3). SEQ ID NO:3 induced IFN-α (FIGS. 12A and C) and IP-10 (FIGS. 12B and D) at both a 3 hour and a 24 hour time point. SEQ ID NO:3 activity was compared to that of two ORN (GACACACACACACACACACACAUU; SEQ ID NO:30; and UUAUUAUUAUUAUUAUUAUU (phosphorothioate backbone); SEQ ID NO:33) that induce both TLR7- and TLR8-associated cytokines and two ORN (UUG-UUGUUGUUGUUGUUGUU; SEQ ID NO:31; and UUA-UUAUUAUUAUUAUUAUU (phosphodiester backbone); SEQ ID NO:32) that induce mainly TLR8-associated cytokines. The x-axes show the ORN used (including saline and DOTAP as negative controls) and the y-axes show cytokine concentration in pg/ml. HBS, buffered saline.
Figure 12B:
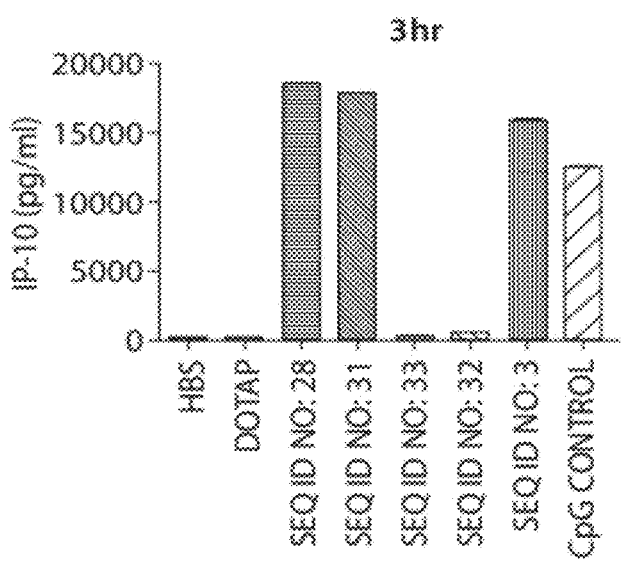
Figure 12C:
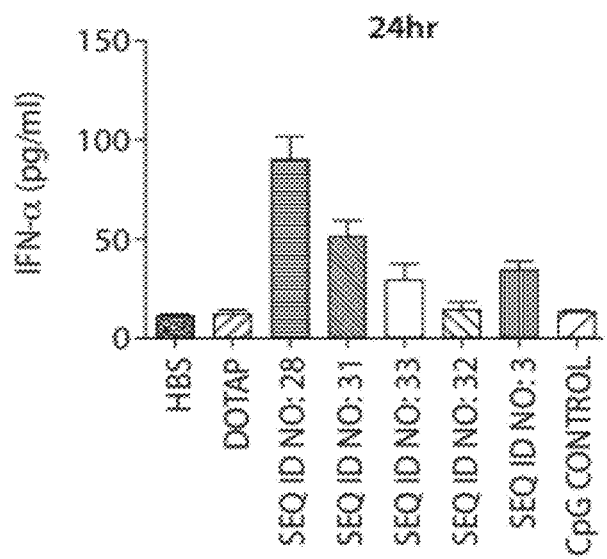
Figure 12D:
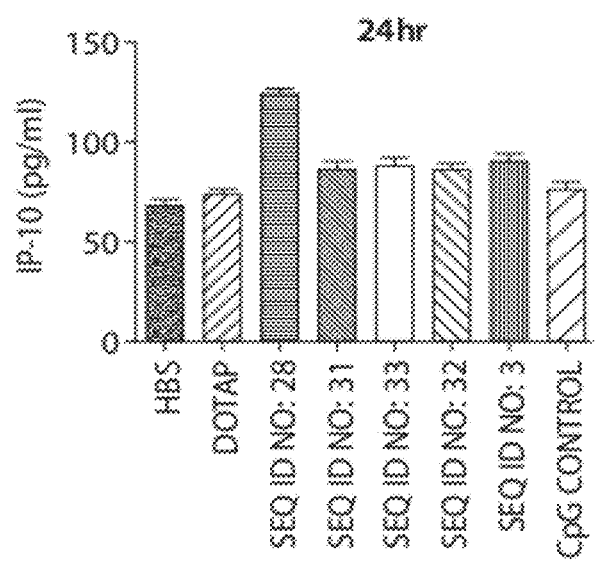
Figure 13A:
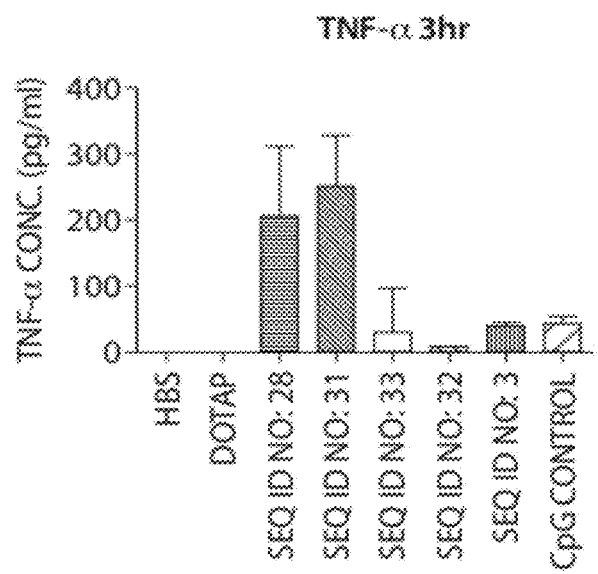
FIG. 13 is five graphs comparing in vivo cytokine induction by an ORN with the immunostimulatory UCA motif (SEQ ID NO:3). SEQ ID NO:3 did not induce substantial amounts of TNF-α, IL-2, IL-12, IL-6, or IL-10 (FIGS. 13A-E, respectively) at a 3 hour time point. SEQ ID NO:3 activity was compared to that of two ORN that induce both TLR7- and TLR8-associated cytokines (SEQ ID NO:30 and 33) and two ORN that induce mainly TLR8-associated cytokines (SEQ ID NO:31 and 32). The x-axes show the ORN used (including saline and DOTAP as negative controls) and the y-axes show cytokine concentration in pg/ml. HBS, buffered saline.
Figure 13B:
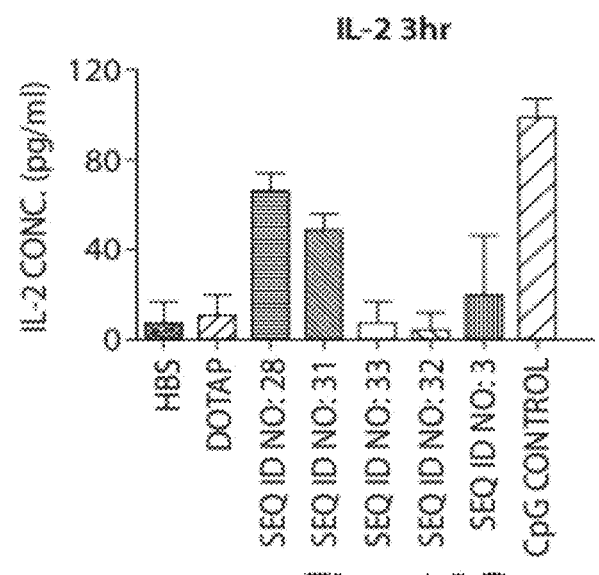
Figure 13C:
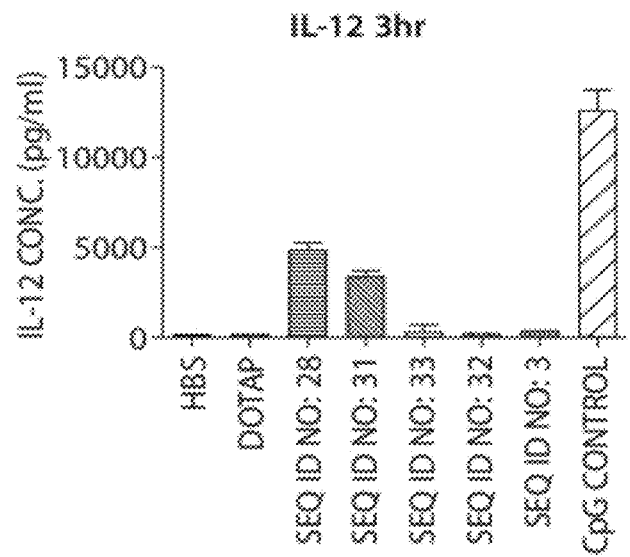
Figure 13D:
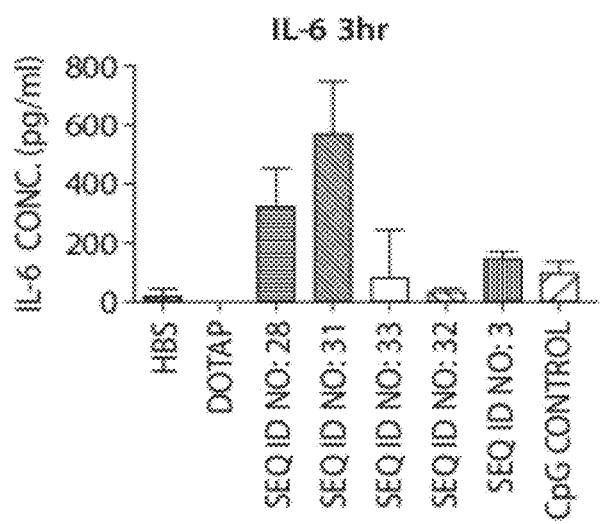
Figure 13E:
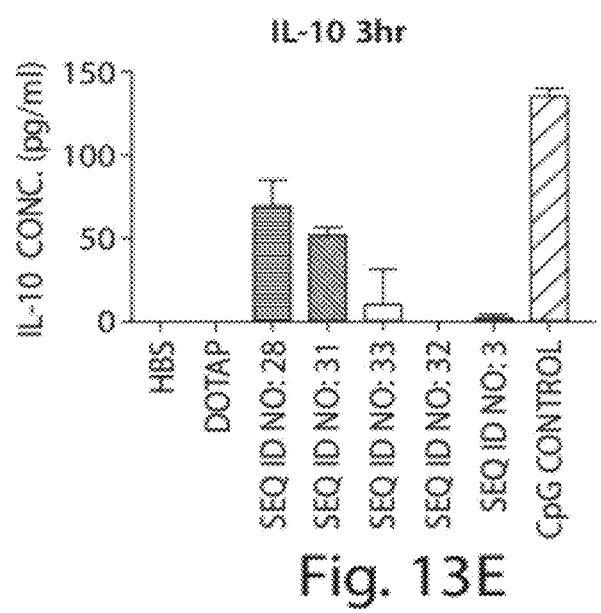

ORN with the UCA motif were tested for the induction of cytokines and chemokines in vivo. BALB/c mice were divided into two groups of five each and ORN, DOTAP, or buffered saline (HBS) were administered intravenously. The first group of animals was bled 3 hours after injection and serum levels of IP-10, IFN-α, TNF-α, IL-2, IL-12, IL-6, and IL-10 were determined using appropriate cytokine-specific ELISA. The second group of animals was bled 24 hours after injection and serum levels of IFN-α and IP-10 were determined. The ability of the UCA ORN SEQ ID NO:3 to induce cytokines and chemokines was compared to the ability of two ORN (GACACACACACACACACACACAUU; SEQ ID NO:30; and UUAUUAUUAUUAUUAUUAUU (phosphorothioate backbone); SEQ ID NO:33) that induce both TLR7- and TLR8-associated cytokines and two ORN (UUGUUG-UUGUUGUUGUUGUU; SEQ ID NO:31; and UUAUUA-UUAUUAUUAUUAUU (phosphodiester backbone); SEQ ID NO:32) that induce mainly TLR8-associated cytokines. CpG ODN 1826 (TCCATGACGTTCCTGACGTT; SEQ ID NO: 36) was also used as a control. SEQ ID NO:3 induced IFN-α (FIGS. 12A and C) and IP-10 (FIGS. 12B and D) at both a 3 hour and a 24 hour time point, but did not induce substantial amounts of TNF-α, IL-2, IL-12, IL-6, or IL-10 (FIGS. 13A-E, respectively) at a 3 hour time point. Thus, SEQ ID NO:3 induced only IFN-α and IFN-α-associated cytokines.

Figure 14A:
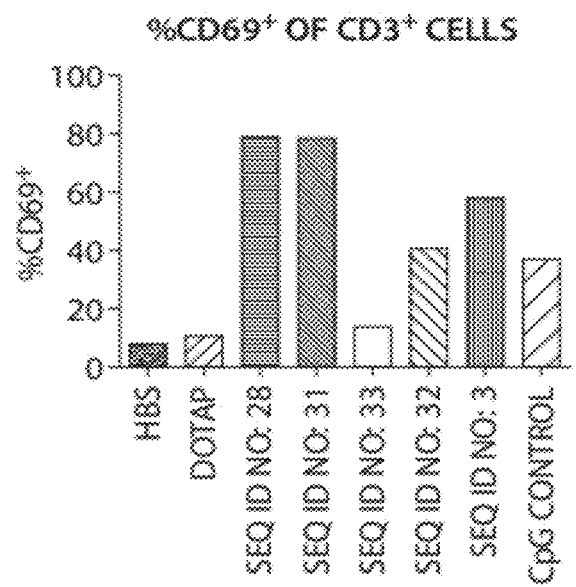
FIG. 14 is four bar graphs showing in vivo activation of spleen cells by an ORN with the immunostimulatory UCA motif (SEQ ID NO:3). SEQ ID NO:3 activated spleen CD3+ T cells (FIGS. 14A and B) and DX5+ B cells (FIGS. 14C and D). Cells were isolated from spleen and separated by FACS analysis. The x-axes show the ORN used (including saline and DOTAP as negative controls) and the y-axes show % CD69+ cells (A and C) or IL-12R+ cells (B and D). HBS, buffered saline.
Figure 14B:
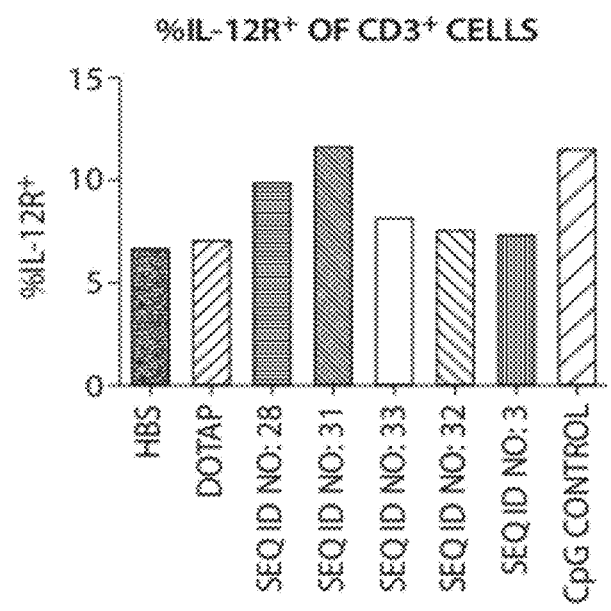
Figure 14C:
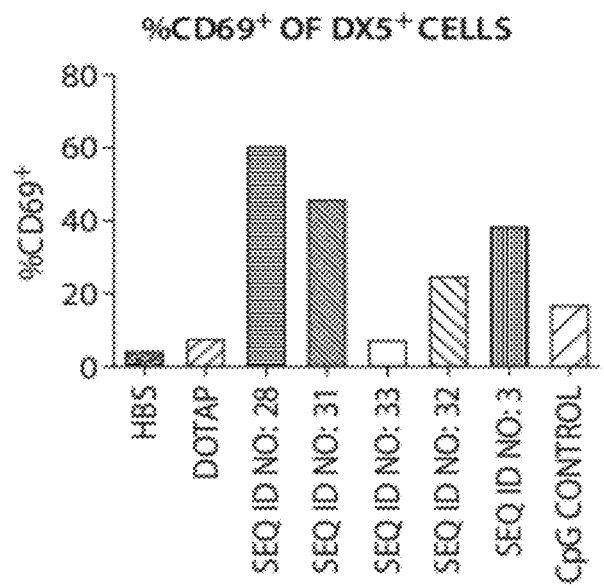
Figure 14D:
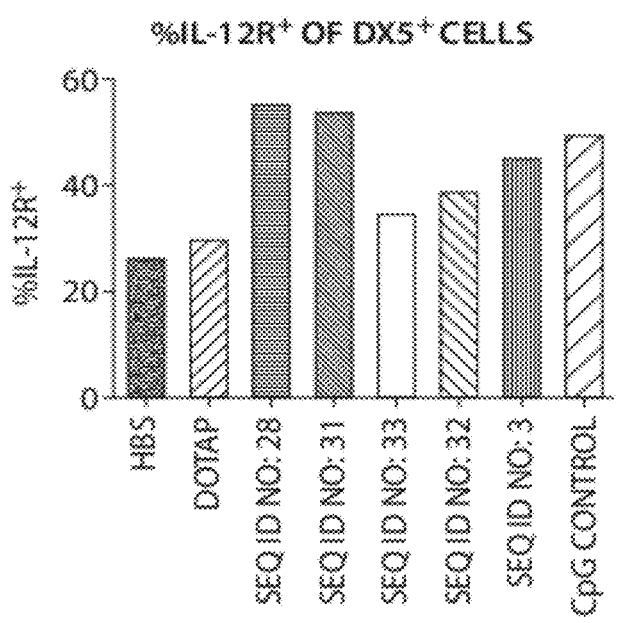

In addition, UCA ORN were shown to activate both B and T cells from spleen. SEQ ID NO:3 activated spleen CD3+ T cells (FIGS. 14A and B) and DX5+ B cells (FIGS. 14C and D).

Example 5

Presence of UCA Motif, not Just U, is Important for IFN-α Induction

In this experiment is was shown that the presence of one to three uridines is not sufficient for induction of IFN-α. Human PBMC from three healthy donors were incubated for 24 with varying amounts of ORN (SEQ ID NOs 26-30; Table 8) in the presence of DOTAP (starting concentration: 2 µM ORN plus 25 µg/ml DOTAP, 1:3 serial dilution in PBS)h. IFN-α was measured in supernatants with appropriate ELISA.

TABLE 8

| SEQ ID NO: 26 | rG-rA-rC-rA-rC-rA-rC-rA-rC-rA-rC-rA-rC-rA-rC-rA-rC-rA-rC-rA-rC-rU-rU-rU |
|---|---|
| SEQ ID NO: 27 | rG-rA-rC-rA-rC-rA-rC-rA-rC-rA-rC-rU-rC-rA-rC-rA-rC-rA-rC-rA-rC-rA-rC-rA |
| SEQ ID NO: 28 | rU*rU*rG*rU*rU*rG*rU*rU*rG*rU*rU*rG*rU*rU*rG*rU*rU*rG*rU*rU |
| SEQ ID NO: 29 | rG-rA-rC-rA-rC-rA-rC-rA-rC-rA-rC-rA-rC-rA-rC-rA-rC-rA-rC-rA-rC-rA-rC-rU |
| SEQ ID NO: 30 | rG-rA-rC-rA-rC-rA-rC-rA-rC-rA-rC-rA-rC-rA-rC-rA-rC-rA-rC-rA-rC-rA-rU-rU |

Figure 15:
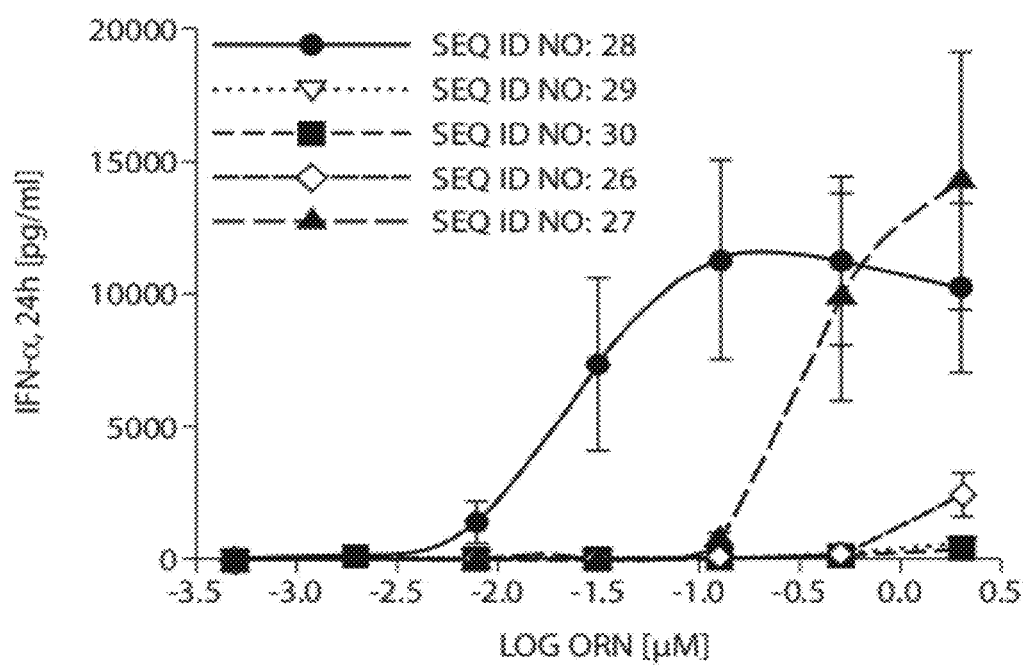
FIG. 15 is a graph depicting the induction of IFN-α by the indicated ORN including SEQ ID NO:27 with a single U in a UCA motif as compared to other ORN with up to three U's but no UCA motif. The y-axis is IFN-α concentration in pg/ml and the x-axis shows log ORN concentration in µM.
Figure 16A:
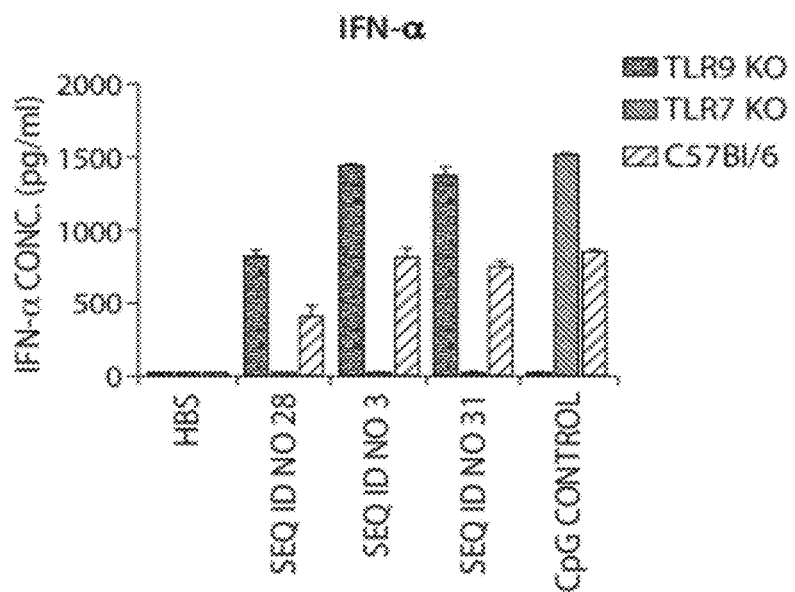
FIG. 16 is four bar graphs depicting the induction of IFN-α, IP-10, IL-12, and IL-6 in TLR9 knock-out (TLR9 KO), TLR7 knock-out (TLR7 KO), and control C57BL/6 mice in response to the indicated ORN or CpG ODN 1826 (SEQ ID NO:34). HBS, buffered saline.
Figure 16B:
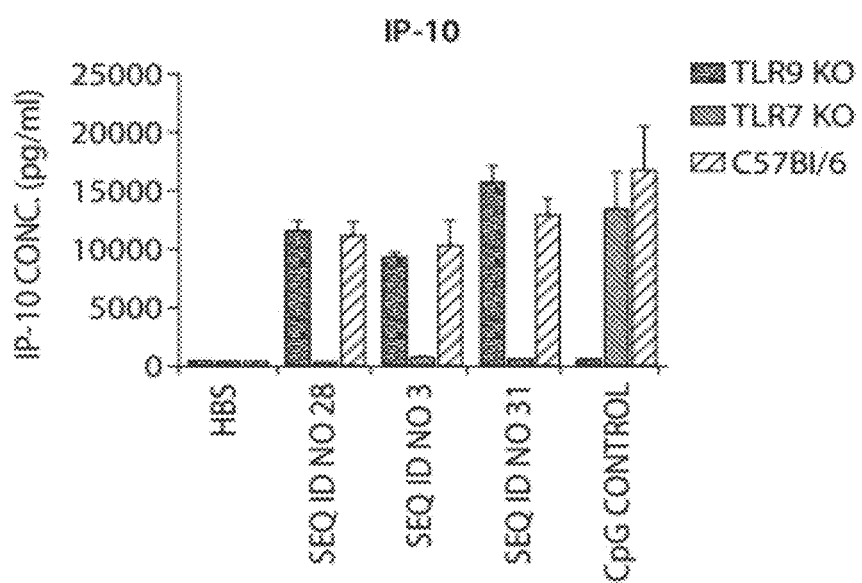
Figure 16C:
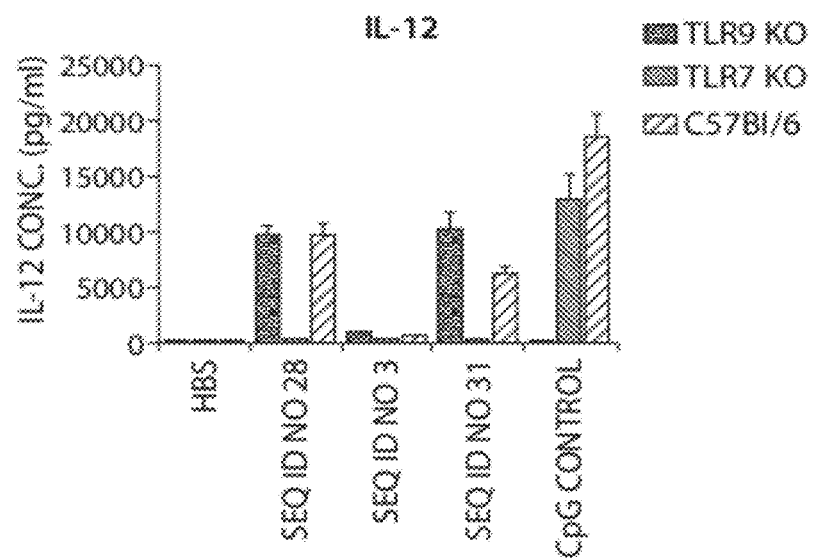
Figure 16D:
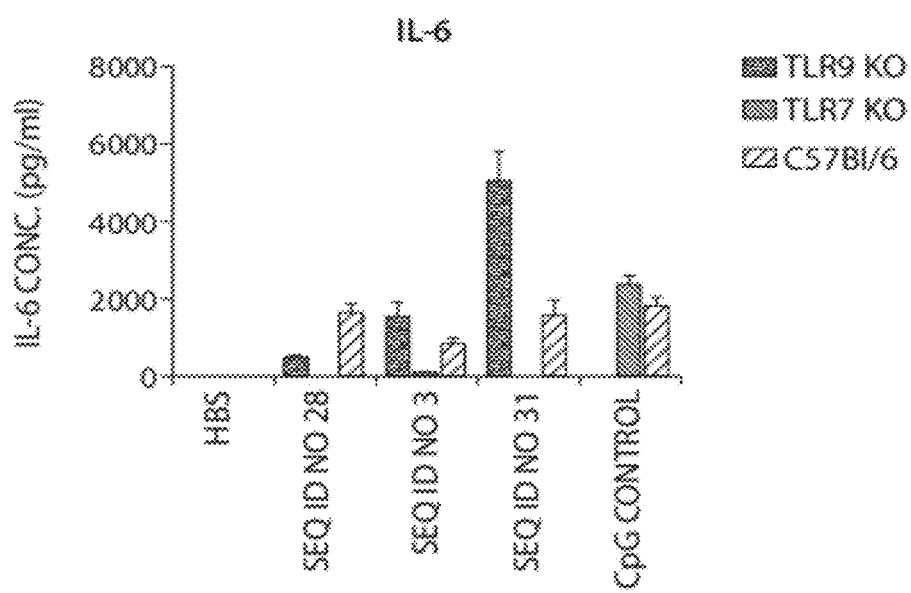

Results are shown in FIG. 15. SEQ ID NOs 26, 29, and 30, without the UCA motif, did not induce IFN-α despite the presence of up to three uridines in these ORN. In contrast, SEQ ID NO:27, containing only one U embedded within the UCA motif, did induce significant amounts of IFN-α.

Example 6

Cytokine Induction In Vivo is Strongly TLR-7-dependent

In this experiment it was shown that TLR7-deficient mice do not react to ORN of the invention. TLR9 knock-out (TLR9 KO) and TLR7 knock-out (TLR7 KO) mice backcrossed on C57BL/6 background, and C57BL/6 control mice (n=4 per group), were injected intravenously with 100 µg of selected ORN (SEQ ID NO:3, 28, or 31) or positive control CpG ODN 1826 (SEQ ID NO:36) 1:2 in DOTAP (Sigma) or buffered saline (HBS) as negative control. Three hours after injection, plasma was obtained and analyzed for IFN-α, IP-10, IL-12, and IL-6 using appropriate Luminex and ELISA.

Results are shown in FIG. 16. TLR7 KO mice demonstrated essentially no induction of IFN-α, IP-10, IL-12, or IL-6 in response to SEQ ID NO:3, 28, or 31 but robust induction of these same cytokines in response to CpG ODN. In contrast, TLR9 KO mice demonstrated varying degrees of induction of IFN-α, IP-10, IL-12, and IL-6 in response to SEQ ID NO:3, 28, or 31 no induction of these same cytokines in response to CpG ODN. Control C57BL/6 mice demonstrated varying degrees of induction of IFN-α, IP-10, IL-12, and IL-6 in response to SEQ ID NO:3, 28, or 31 and robust induction of these same cytokines in response to CpG ODN.

Example 7

Cytokine Induction In Vivo is Strongly MyD88-dependent

In this experiment it was shown that MyD88-deficient mice do not react to ORN of the invention. MyD88 knock-out (MyD88 KO) mice backcrossed on C57BL/6 background, and C57BL/6 control mice (n=4 per group), were injected intravenously with 100 µg of selected ORN (SEQ ID NO:3, 28, or 31) or positive control CpG ODN 1826 (SEQ ID NO:36) 1:2 in DOTAP (Sigma) or buffered saline (HBS) as negative control. Three hours after injection, plasma was obtained and analyzed for IFN-α and IP-10 using appropriate Luminex and ELISA.

Figure 17A:
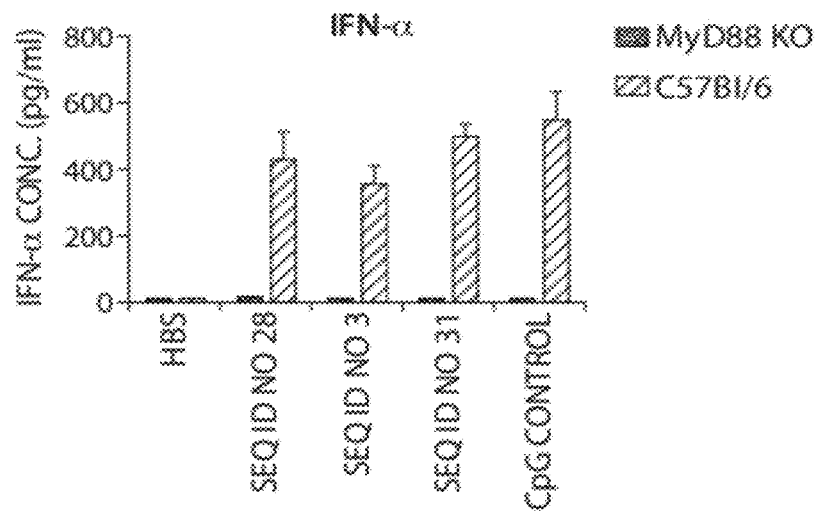
FIG. 17 is a pair of bar graphs depicting the induction of IFN-α and IP-10 in MyD88 knock-out (MyD88 KO) and control C57BL/6 mice. HBS, buffered saline.
Figure 17B:
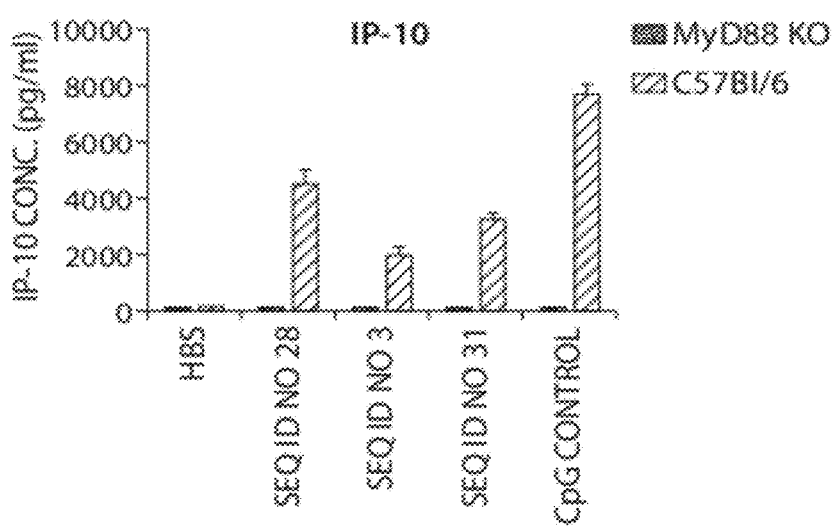

Results are shown in FIG. 17. MyD88 KO mice demonstrated essentially no induction of IFN-α or IP-10 in response to SEQ ID NO:3, 28, or 31 and similarly in response to CpG ODN. In contrast, control C57BL/6 mice demonstrated robust induction of IFN-α and IP-10 in response to SEQ ID NO:3, 28, and 31 as well as in response to CpG ODN.

In summary, a new backbone-specific motif has been defined that is responsible for the induction of IFN-α (most likely TLR7-mediated) and little activation of other (most likely TLR8-mediated) cytokines such IL-12, IFN-γ or TNF-α. The minimal motif determining these properties is rU-rC-rA. The backbone is phosphodiester. The optimal motif according to the data is rN-rC-rU-rC-rA-rN with N=C, A, G but not U (for minimal TLR8-mediated cytokine responses).

Having thus described several aspects of at least one embodiment of this invention, it is to be appreciated various alterations, modifications, and improvements to will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating an allergic condition, comprising administering to a subject having an allergic condition an effective amount of an RNA nucleotide polymer selected from:

A-A-A-C-G-C-U-C-A-G-C-C-A-A-A-G-C-A-G; (SEQ ID NO 3)

A-A-A-C-G-C-U-C-A-C-C-A-A-A-G-C-A-G; (SEQ ID NO 17)

A-A-A-C-A-C-U-C-A-G-C-C-A-A-A-G-C-A-G; (SEQ ID NO 22)
and

A-A-A-C-C-C-U-C-A-G-C-C-A-A-A-G-C-A-G; (SEQ ID NO 23)
and wherein the polymer comprises a phosphodiester backbone.

2. The method of claim 1, further comprising administering an allergen to the subject having an allergic condition.

3. The method of claim 2, wherein the polymer is conjugated to the allergen.

4. The method according to any one of the preceding claims, wherein the polymer is administered in association with a pharmaceutical composition.

5. The method according to claim 4 further comprising a delivery vehicle.

* * * * *